United States Patent
Pulé et al.

(10) Patent No.: US 12,269,860 B2
(45) Date of Patent: Apr. 8, 2025

(54) COMPOSITIONS AND METHODS COMPRISING ENGINEERED CHIMERIC ANTIGEN RECEPTOR AND MODULATOR OF CAR

(71) Applicant: AUTOLUS LIMITED, London (GB)

(72) Inventors: Martin Pulé, London (GB); Vijay Peddareddigari, London (GB); Christian Itin, London (GB)

(73) Assignee: AUTOLUS LIMITED, London (GB)

( * ) Notice: Subject to any disclaimer, the term of this patent is extended or adjusted under 35 U.S.C. 154(b) by 535 days.

(21) Appl. No.: 17/746,664

(22) Filed: May 17, 2022

(65) Prior Publication Data
US 2022/0364116 A1   Nov. 17, 2022

Related U.S. Application Data

(63) Continuation of application No. 17/436,673, filed as application No. PCT/GB2020/050535 on Mar. 6, 2020.

(30) Foreign Application Priority Data

Mar. 8, 2019 (GB) .................................... 1903237
Oct. 2, 2019 (GB) .................................... 1914216
Nov. 5, 2019 (GB) .................................... 1916077

(51) Int. Cl.
| | |
|---|---|
| *A61K 48/00* | (2006.01) |
| *A61K 39/00* | (2006.01) |
| *C07K 14/71* | (2006.01) |
| *C07K 14/715* | (2006.01) |
| *C07K 14/725* | (2006.01) |
| *C12N 15/86* | (2006.01) |

(52) U.S. Cl.
CPC ...... *C07K 14/7051* (2013.01); *A61K 39/4611* (2023.05); *A61K 39/4631* (2023.05); *A61K 39/464412* (2023.05); *A61K 39/464413* (2023.05); *A61K 39/464471* (2023.05); *A61K 39/464495* (2023.05); *A61K 48/005* (2013.01); *C07K 14/71* (2013.01); *C07K 14/715* (2013.01); *C12N 15/86* (2013.01); *A61K 2239/11* (2023.05); *A61K 2239/31* (2023.05); *A61K 2239/38* (2023.05); *A61K 2239/47* (2023.05); *C07K 2319/03* (2013.01); *C12N 2740/16043* (2013.01); *C12N 2800/40* (2013.01)

(58) Field of Classification Search
None
See application file for complete search history.

(56) References Cited

U.S. PATENT DOCUMENTS

| | | |
|---|---|---|
| 10,098,911 B2 | 10/2018 | Pule et al. |
| 10,478,457 B2 | 11/2019 | Pule et al. |
| 10,800,854 B2 | 10/2020 | Pule et al. |
| 10,800,855 B2 | 10/2020 | Pule et al. |
| 10,925,943 B2 | 2/2021 | Pule et al. |
| 11,103,532 B2 | 8/2021 | Pule et al. |
| 11,345,734 B2 | 5/2022 | Pule et al. |
| 11,479,613 B2 | 10/2022 | Pulé et al. |
| 11,701,386 B2 | 7/2023 | Pulé et al. |
| 11,959,084 B2 | 4/2024 | Cordoba et al. |
| 2015/0023937 A1 | 1/2015 | Vera Valdes et al. |
| 2015/0093401 A1 | 4/2015 | Pule et al. |
| 2017/0291953 A1 | 10/2017 | Tamada et al. |
| 2017/0354682 A1 | 12/2017 | Pulé et al. |
| 2018/0064785 A1 | 3/2018 | Averback |
| 2018/0244797 A1 | 8/2018 | Pulé et al. |
| 2019/0015451 A1 | 1/2019 | Pulé et al. |
| 2019/0016820 A1 | 1/2019 | Pulé et al. |
| 2019/0023761 A1 | 1/2019 | Pule et al. |
| 2020/0048359 A1 | 2/2020 | Albelda et al. |
| 2020/0048618 A1 | 2/2020 | Cordoba et al. |
| 2020/0181624 A1 | 6/2020 | Jensen et al. |
| 2020/0222461 A1 | 7/2020 | Pulé et al. |
| 2020/0297766 A1 | 9/2020 | Pule et al. |
| 2021/0040227 A1 | 2/2021 | Pule et al. |
| 2021/0040228 A1 | 2/2021 | Pule et al. |
| 2021/0095003 A1 | 4/2021 | Pule et al. |
| 2021/0113618 A1 | 4/2021 | Pule et al. |

(Continued)

FOREIGN PATENT DOCUMENTS

| | | |
|---|---|---|
| CN | 107109421 A | 8/2017 |
| CN | 107406517 A | 11/2017 |

(Continued)

OTHER PUBLICATIONS

Baldan et al., "A Dominant Negative SHP-2 Which Abrogates PD-1 Signalling Pathways and Restores Function of Cytotoxic CAR T Cells," Blood 130(1):3190 (2017).

(Continued)

*Primary Examiner* — Christopher M Babic
*Assistant Examiner* — Alyssa G Weston

(57) ABSTRACT

There is provided method for making a cell composition which comprises step of transducing a population of cells with a mixture of at least two viral vectors, wherein at least one vector comprises a nucleic acid sequence which encodes a chimeric antigen receptor (CAR); and wherein at least one vector comprises a nucleic acid encoding an activity modulator which modulates the activity of the CAR, of a cell expressing the CAR, or of a target cell. There is also provided a cell composition made by such a method and its use in the treatment of diseases such as cancer.

5 Claims, 25 Drawing Sheets

Specification includes a Sequence Listing.

(56) References Cited

U.S. PATENT DOCUMENTS

| | | |
|---|---|---|
| 2021/0308240 A1 | 10/2021 | Pule et al. |
| 2022/0106602 A1 | 4/2022 | Cordoba et al. |
| 2022/0267404 A1 | 8/2022 | Pule et al. |
| 2022/0372105 A1* | 11/2022 | Ostertag ............ C07K 14/7155 |
| 2023/0133682 A1 | 5/2023 | Pulé et al. |
| 2024/0075066 A1 | 3/2024 | Pulé et al. |
| 2024/0156926 A1 | 5/2024 | Pulé et al. |

FOREIGN PATENT DOCUMENTS

| | | |
|---|---|---|
| EP | 3205720 A1 | 8/2017 |
| WO | WO-2000/063372 A1 | 10/2000 |
| WO | WO-2013/123061 | 8/2013 |
| WO | WO-2013/153391 A1 | 10/2013 |
| WO | WO-2015/052538 A1 | 4/2015 |
| WO | WO-2015/075469 A1 | 5/2015 |
| WO | WO-2015/075470 A1 | 5/2015 |
| WO | WO-2015/132604 A1 | 9/2015 |
| WO | WO-2015/150771 A1 | 10/2015 |
| WO | WO-2016/030691 A1 | 3/2016 |
| WO | WO-2016/102965 A1 | 6/2016 |
| WO | WO-2016090337 A1 | 6/2016 |
| WO | WO-2016/124930 A1 | 8/2016 |
| WO | WO-2016/135470 A1 | 9/2016 |
| WO | WO-2016/139487 A1 | 9/2016 |
| WO | WO-2016/193696 A1 | 12/2016 |
| WO | WO-2017/029512 A1 | 2/2017 |
| WO | WO-2017/147383 A1 | 8/2017 |
| WO | WO-2017/181148 A2 | 10/2017 |
| WO | WO-2018/045325 A1 | 3/2018 |
| WO | WO-2018/096361 A1 | 5/2018 |
| WO | WO-2018/115865 A1 | 6/2018 |
| WO | WO-2018/160731 A1 | 9/2018 |
| WO | WO-2018/193231 A1 | 10/2018 |
| WO | WO-2019/025800 A1 | 2/2019 |
| WO | WO-2019/053420 A1 | 3/2019 |
| WO | WO-2019/092442 A1 | 5/2019 |
| WO | WO-2019/116046 A1 | 6/2019 |
| WO | WO-2019/162695 A1 | 8/2019 |
| WO | WO-2020/025953 A2 | 2/2020 |
| WO | WO-2020/074868 A1 | 4/2020 |
| WO | WO-2020/183131 A1 | 9/2020 |

OTHER PUBLICATIONS

Bedinger et al., "Development and characterization of human monoclonal antibodies that neutralize multiple TGF β isoforms," MABS 8(2):389-404 (2016).

Bejcek et al., "Development and Characterization of Three Recombinant Single Chain Antibody Fragments (scFvs) Directed against the CD19 Antigen," Cancer Res. 55:2346-2351 (1995).

Donnelly et al., "The 'cleavage' activities of foot-and-mouth disease virus 2A site-directed mutants and naturally occurring '2A-like' sequences," Journal of General Virology 82:1027-1041 (2001).

Grada et al., "TanCAR: A Novel Bispecific Chimeric Antigen Receptor for Cancer Immunotherapy," Molecular Therapy—Nucleic Acids 2, e105, 11 pages (2013).

Haso et al., "Anti-CD22-Chimeric Antigen Receptors Targeting B Cell Precursor Acute Lymphoblastic Leukemia," Blood 121(7):1165-1174 (2013).

Herbst et al., "B-Cell Depletion In Vitro and In Vivo with Afucosylated Anti-CD19 Antibody," J. Pharmacol. Exp. Ther. 335:213-222 (2010).

International Search Report and Written Opinion from International Application No. PCT/GB2020/050535 dated Apr. 17, 2020.

Junghans et al., "Phase I Trial of Anti-PSMA Designer CAR-T Cells in Prostate Cancer: Possible Role for Interacting Interleukin 2-T Cell Pharmacodynamics as a Determinant of Clinical Response," Prostate 76:1257-1270 (2016).

Kansas et al., "Transmembrane Signals Generated Through MHC Class II, CD19, CD20, CD39, and CD40 Antigens Induce LFA-1-Dependent and Independent Adhesion in Human B Cells Through a Tyrosine Kinase-Dependent Pathway," J. Immunol. 147:4094-4102 (1991).

Kim et al., "An engineered transforming growth factor β (TGF-β) monomer that functions as a dominant negative block TGF-β signaling," J. Biol. Chem. 292(17)7173-7188 (2017).

Kloss et al., "Dominant-Negative TGF-β Receptor Enhances PSMA-Targeted Human CAR T Cell Proliferation and Augments Prostate Cancer Eradication," Mol. Ther. 26(7):1855-1866 (2018).

Leen et al., "Reversal of Tumor Immune Inhibition Using a Chimeric Cytokine Receptor," Molecular Therapy 22(6):1211-1220 (2014).

Mauldin et al., "The tyrosine phosphatase SHP-1 dampens murine Th17 development," Blood 119(19):4419-4429 (2012).

Meeker et al., "A Unique Human B Lymphocyte Antigen Defined by a Monoclonal Antibody," Hybridoma 3:305-320 (1984).

Newick et al., "Chimeric antigen receptor T-cell therapy for solid tumors," Molecular Therapy—Oncolytics 3:16006, 7 pages (2016).

Nicholson et al., "Constructions and Characterisation of a Functional CD19 Specific Single Chain Fv Fragment for Immunotherapy of B Lineage Leukaemia and Lymphoma," Mol. Immunol. 34:1157-1165 (1997).

Pezzutto et al., "CD19 Monoclonal Antibody HD37 Inhibits Anti-Immunoglobulin-Induced B Cell Activation and Proliferation," J. Immunol. Baltim 138:2793-2799 (1987).

Roguska et al., "A comparison of two murine monoclonal antibodies humanized by CFR-grafting and variable domain resurfacing," Protein Eng. 9:895-904 (1996).

Yazawa et al., "Immunotherapy using unconjugated CD19 monoclonal antibodies in animal models for B lymphocyte malignancies and autoimmune disease," Proc. Natl. Acad. Sci. 102:15178-15183 (2005).

* cited by examiner

```
                       SEQUENCE LISTING

<160> NUMBER OF SEQ ID NOS: 81

<210> SEQ ID NO 1
<211> LENGTH: 7
<212> TYPE: PRT
<213> ORGANISM: Artificial Sequence
<220> FEATURE:
<223> OTHER INFORMATION: heavy chain variable region (VH)
      complementarity determining region (CDR) CDR1

<400> SEQUENCE: 1

Gly Tyr Ala Phe Ser Ser Ser
1               5

<210> SEQ ID NO 2
<211> LENGTH: 6
<212> TYPE: PRT
<213> ORGANISM: Artificial Sequence
<220> FEATURE:
<223> OTHER INFORMATION: VH CDR, CDR2

<400> SEQUENCE: 2

Tyr Pro Gly Asp Glu Asp
1               5

<210> SEQ ID NO 3
<211> LENGTH: 10
<212> TYPE: PRT
<213> ORGANISM: Artificial Sequence
<220> FEATURE:
<223> OTHER INFORMATION: VH CDR, CDR3

<400> SEQUENCE: 3

Ser Leu Leu Tyr Gly Asp Tyr Leu Asp Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: light chain variable region (VL) CDR, CDR1

<400> SEQUENCE: 4

Ser Ala Ser Ser Ser Val Ser Tyr Met His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: VL CDR, CDR2

<400> SEQUENCE: 5
```

```
Asp Thr Ser Lys Leu Ala Ser
1               5

<210> SEQ ID NO 6
<211> LENGTH: 9
<212> TYPE: PRT
<213> ORGANISM: Artificial Sequence
<220> FEATURE:
<223> OTHER INFORMATION: VL CDR, CDR3

<400> SEQUENCE: 6

Gln Gln Trp Asn Ile Asn Pro Leu Thr
1               5

<210> SEQ ID NO 7
<211> LENGTH: 119
<212> TYPE: PRT
<213> ORGANISM: Artificial Sequence
<220> FEATURE:
<223> OTHER INFORMATION: VH domain sequence

<400> SEQUENCE: 7

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
                20                  25                  30

Trp Met Asn Trp Val Lys Gln Arg Pro Gly Lys Gly Leu Glu Trp Ile
            35                  40                  45

Gly Arg Ile Tyr Pro Gly Asp Glu Asp Thr Asn Tyr Ser Gly Lys Phe
        50                  55                  60

Lys Asp Lys Ala Thr Leu Thr Ala Asp Lys Ser Ser Thr Thr Ala Tyr
65                  70                  75                  80

Met Gln Leu Ser Ser Leu Thr Ser Glu Asp Ser Ala Val Tyr Phe Cys
                85                  90                  95

Ala Arg Ser Leu Leu Tyr Gly Asp Tyr Leu Asp Tyr Trp Gly Gln Gly
            100                 105                 110

Thr Thr Leu Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: VL domain sequence

<400> SEQUENCE: 8

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Asp Arg Phe Ser Gly Ser
        50                  55                  60

Gly Ser Gly Thr Ser Tyr Phe Leu Thr Ile Asn Asn Met Glu Ala Glu
65                  70                  75                  80

Asp Ala Ala Thr Tyr Tyr Cys Gln Gln Trp Asn Ile Asn Pro Leu Thr
                85                  90                  95
```

```
Phe Gly Ala Gly Thr Lys Leu Glu Leu Lys Arg
            100                 105

<210> SEQ ID NO 9
<211> LENGTH: 20
<212> TYPE: PRT
<213> ORGANISM: Foot-and-mouth disease virus

<400> SEQUENCE: 9

Arg Ala Glu Gly Arg Gly Ser Leu Leu Thr Cys Gly Asp Val Glu Glu
1               5                   10                  15

Asn Pro Gly Pro
            20

<210> SEQ ID NO 10
<211> LENGTH: 5
<212> TYPE: PRT
<213> ORGANISM: Artificial Sequence
<220> FEATURE:
<223> OTHER INFORMATION: VH CDR, CDR1

<400> SEQUENCE: 10

Asn Phe Ala Met Ala
1               5

<210> SEQ ID NO 11
<211> LENGTH: 17
<212> TYPE: PRT
<213> ORGANISM: Artificial Sequence
<220> FEATURE:
<223> OTHER INFORMATION: VH CDR, CDR2

<400> SEQUENCE: 11

Ser Ile Ser Thr Gly Gly Gly Asn Thr Tyr Tyr Arg Asp Ser Val Lys
1               5                   10                  15

Gly

<210> SEQ ID NO 12
<211> LENGTH: 18
<212> TYPE: PRT
<213> ORGANISM: Artificial Sequence
<220> FEATURE:
<223> OTHER INFORMATION: VH CDR, CDR3

<400> SEQUENCE: 12

Gln Arg Asn Tyr Tyr Asp Gly Ser Tyr Asp Tyr Glu Gly Tyr Thr Met
1               5                   10                  15

Asp Ala

<210> SEQ ID NO 13
<211> LENGTH: 11
<212> TYPE: PRT
<213> ORGANISM: Artificial Sequence
<220> FEATURE:
<223> OTHER INFORMATION: VL CDR, CDR1

<400> SEQUENCE: 13

Arg Ser Ser Gln Asp Ile Gly Asn Tyr Leu Thr
1               5                   10

<210> SEQ ID NO 14
<211> LENGTH: 7
<212> TYPE: PRT
<213> ORGANISM: Artificial Sequence
<220> FEATURE:
```

<223> OTHER INFORMATION: VL CDR, CDR2

<400> SEQUENCE: 14

Gly Ala Ile Lys Leu Glu Asp
1               5

<210> SEQ ID NO 15
<211> LENGTH: 7
<212> TYPE: PRT
<213> ORGANISM: Artificial Sequence
<220> FEATURE:
<223> OTHER INFORMATION: VL CDR, CDR3

<400> SEQUENCE: 15

Leu Gln Ser Ile Gln Tyr Pro
1               5

<210> SEQ ID NO 16
<211> LENGTH: 127
<212> TYPE: PRT
<213> ORGANISM: Artificial Sequence
<220> FEATURE:
<223> OTHER INFORMATION: VH domain sequence

<400> SEQUENCE: 16

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Phe
            20                  25                  30

Ala Met Ala Trp Val Arg Gln Pro Thr Lys Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Asp Asp Ala Lys Asn Thr Gln Tyr
65                  70                  75                  80

Leu Gln Met Asp Ser Leu Arg Ser Glu Asp Thr Ala Thr Tyr Tyr Cys
                85                  90                  95

Ala Arg Gln Arg Asn Tyr Tyr Asp Gly Ser Tyr Asp Tyr Glu Gly Tyr
            100                 105                 110

Thr Met Asp Ala Trp Gly Gln Gly Thr Ser Val Thr Val Ser Ser
        115                 120                 125

<210> SEQ ID NO 17
<211> LENGTH: 107
<212> TYPE: PRT
<213> ORGANISM: Artificial Sequence
<220> FEATURE:
<223> OTHER INFORMATION: VL domain sequence

<400> SEQUENCE: 17

Asp Ile Gln Met Thr Gln Ser Pro Ser Leu Ser Ala Ser Leu Gly
1               5                   10                  15

Asp Arg Val Thr Ile Thr Cys Arg Ser Ser Gln Asp Ile Gly Asn Tyr
            20                  25                  30

Leu Thr Trp Phe Gln Gln Lys Val Gly Arg Ser Pro Arg Arg Met Ile
        35                  40                  45

Tyr Gly Ala Ile Lys Leu Glu Asp Gly Val Pro Ser Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Val Ala Asp Tyr Gln Cys Leu Gln Ser Ile Gln Tyr Pro Phe
            85                  90                  95

Thr Phe Gly Ser Gly Thr Lys Leu Glu Ile Lys
            100                 105

<210> SEQ ID NO 18
<211> LENGTH: 254
<212> TYPE: PRT
<213> ORGANISM: Artificial Sequence
<220> FEATURE:
<223> OTHER INFORMATION: tyrosine kinase domain of Fyn

<400> SEQUENCE: 18

Leu Gln Leu Ile Lys Arg Leu Gly Asn Gly Gln Phe Gly Glu Val Trp
1               5                   10                  15

Met Gly Thr Trp Asn Gly Asn Thr Lys Val Ala Ile Lys Thr Leu Lys
            20                  25                  30

Pro Gly Thr Met Ser Pro Glu Ser Phe Leu Glu Glu Ala Gln Ile Met
            35                  40                  45

Lys Lys Leu Lys His Asp Lys Leu Val Gln Leu Tyr Ala Val Val Ser
        50                  55                  60

Glu Glu Pro Ile Tyr Ile Val Thr Glu Tyr Met Asn Lys Gly Ser Leu
65                  70                  75                  80

Leu Asp Phe Leu Lys Asp Gly Glu Gly Arg Ala Leu Lys Leu Pro Asn
                85                  90                  95

Leu Val Asp Met Ala Ala Gln Val Ala Ala Gly Met Ala Tyr Ile Glu
            100                 105                 110

Arg Met Asn Tyr Ile His Arg Asp Leu Arg Ser Ala Asn Ile Leu Val
            115                 120                 125

Gly Asn Gly Leu Ile Cys Lys Ile Ala Asp Phe Gly Leu Ala Arg Leu
        130                 135                 140

Ile Glu Asp Asn Glu Tyr Thr Ala Arg Gln Gly Ala Lys Phe Pro Ile
145                 150                 155                 160

Lys Trp Thr Ala Pro Glu Arg Ala Leu Tyr Gly Arg Phe Thr Ile Lys
                165                 170                 175

Ser Asp Val Trp Ser Phe Gly Ile Leu Leu Thr Glu Leu Val Thr Lys
            180                 185                 190

Gly Arg Val Pro Tyr Pro Gly Met Asn Asn Arg Glu Val Leu Glu Gln
            195                 200                 205

Val Glu Arg Gly Tyr Arg Met Pro Cys Pro Gln Asp Cys Pro Ile Ser
        210                 215                 220

Leu His Glu Leu Met Ile His Cys Trp Lys Lys Asp Pro Glu Glu Arg
225                 230                 235                 240

Pro Thr Phe Glu Tyr Leu Gln Ser Phe Leu Glu Asp Tyr Phe
                245                 250

<210> SEQ ID NO 19
<211> LENGTH: 254
<212> TYPE: PRT
<213> ORGANISM: Artificial Sequence
<220> FEATURE:
<223> OTHER INFORMATION: tyrosine kinase domain of Src

<400> SEQUENCE: 19

Leu Arg Leu Glu Val Lys Leu Gly Gln Gly Cys Phe Gly Glu Val Trp
1               5                   10                  15

Met Gly Thr Trp Asn Gly Thr Thr Arg Val Ala Ile Lys Thr Leu Lys
            20                  25                  30

Pro Gly Thr Met Ser Pro Glu Ala Phe Leu Gln Ala Gln Val Met
            35                  40                  45

Lys Lys Leu Arg His Glu Lys Leu Val Gln Leu Tyr Ala Val Val Ser
 50                  55                  60

Glu Glu Pro Ile Tyr Ile Val Thr Glu Tyr Met Ser Lys Gly Ser Leu
 65                  70                  75                  80

Leu Asp Phe Leu Lys Gly Glu Thr Gly Lys Tyr Leu Arg Leu Pro Gln
                 85                  90                  95

Leu Val Asp Met Ala Ala Gln Ile Ala Ser Gly Met Ala Tyr Val Glu
                100                 105                 110

Arg Met Asn Tyr Val His Arg Asp Leu Arg Ala Ala Asn Ile Leu Val
            115                 120                 125

Gly Glu Asn Leu Val Cys Lys Val Ala Asp Phe Gly Leu Ala Arg Leu
130                 135                 140

Ile Glu Asp Asn Glu Tyr Thr Ala Arg Gln Gly Ala Lys Phe Pro Ile
145                 150                 155                 160

Lys Trp Thr Ala Pro Glu Ala Ala Leu Tyr Gly Arg Phe Thr Ile Lys
                165                 170                 175

Ser Asp Val Trp Ser Phe Gly Ile Leu Leu Thr Glu Leu Thr Thr Lys
            180                 185                 190

Gly Arg Val Pro Tyr Pro Gly Met Val Asn Arg Glu Val Leu Asp Gln
        195                 200                 205

Val Glu Arg Gly Tyr Arg Met Pro Cys Pro Pro Glu Cys Pro Glu Ser
210                 215                 220

Leu His Asp Leu Met Cys Gln Cys Trp Arg Lys Glu Pro Glu Glu Arg
225                 230                 235                 240

Pro Thr Phe Glu Tyr Leu Gln Ala Phe Leu Glu Asp Tyr Phe
                245                 250

<210> SEQ ID NO 20
<211> LENGTH: 254
<212> TYPE: PRT
<213> ORGANISM: Artificial Sequence
<220> FEATURE:
<223> OTHER INFORMATION: tyrosine kinase domain of Lck

<400> SEQUENCE: 20

Leu Lys Leu Val Glu Arg Leu Gly Ala Gly Gln Phe Gly Glu Val Trp
 1               5                  10                  15

Met Gly Tyr Tyr Asn Gly His Thr Lys Val Ala Val Lys Ser Leu Lys
                20                  25                  30

Gln Gly Ser Met Ser Pro Asp Ala Phe Leu Ala Glu Ala Asn Leu Met
            35                  40                  45

Lys Gln Leu Gln His Gln Arg Leu Val Arg Leu Tyr Ala Val Val Thr
 50                  55                  60

Gln Glu Pro Ile Tyr Ile Ile Thr Glu Tyr Met Glu Asn Gly Ser Leu
 65                  70                  75                  80

Val Asp Phe Leu Lys Thr Pro Ser Gly Ile Lys Leu Thr Ile Asn Lys
                 85                  90                  95

Leu Leu Asp Met Ala Ala Gln Ile Ala Glu Gly Met Ala Phe Ile Glu
                100                 105                 110

Glu Arg Asn Tyr Ile His Arg Asp Leu Arg Ala Ala Asn Ile Leu Val
            115                 120                 125

Ser Asp Thr Leu Ser Cys Lys Ile Ala Asp Phe Gly Leu Ala Arg Leu
130                 135                 140

```
Ile Glu Asp Asn Glu Tyr Thr Ala Arg Glu Gly Ala Lys Phe Pro Ile
145                 150                 155                 160

Lys Trp Thr Ala Pro Glu Ala Ile Asn Tyr Gly Thr Phe Thr Ile Lys
                165                 170                 175

Ser Asp Val Trp Ser Phe Gly Ile Leu Leu Thr Glu Ile Val Thr His
            180                 185                 190

Gly Arg Ile Pro Tyr Pro Gly Met Thr Asn Pro Glu Val Ile Gln Asn
        195                 200                 205

Leu Glu Arg Gly Tyr Arg Met Val Arg Pro Asp Asn Cys Pro Glu Glu
    210                 215                 220

Leu Tyr Gln Leu Met Arg Leu Cys Trp Lys Glu Arg Pro Glu Asp Arg
225                 230                 235                 240

Pro Thr Phe Asp Tyr Leu Arg Ser Val Leu Glu Asp Phe Phe
                245                 250

<210> SEQ ID NO 21
<211> LENGTH: 254
<212> TYPE: PRT
<213> ORGANISM: Artificial Sequence
<220> FEATURE:
<223> OTHER INFORMATION: tyrosine kinase domain of Lck_Y505F

<400> SEQUENCE: 21

Leu Lys Leu Val Glu Arg Leu Gly Ala Gly Gln Phe Gly Glu Val Trp
1               5                   10                  15

Met Gly Tyr Tyr Asn Gly His Thr Lys Val Ala Val Arg Ser Leu Lys
            20                  25                  30

Gln Gly Ser Met Ser Pro Asp Ala Phe Leu Ala Glu Ala Asn Leu Met
        35                  40                  45

Lys Gln Leu Gln His Gln Arg Leu Val Arg Leu Tyr Ala Val Val Thr
    50                  55                  60

Gln Glu Pro Ile Tyr Ile Ile Thr Glu Tyr Met Glu Asn Gly Ser Leu
65                  70                  75                  80

Val Asp Phe Leu Lys Thr Pro Ser Gly Ile Lys Leu Thr Ile Asn Lys
                85                  90                  95

Leu Leu Asp Met Ala Ala Gln Ile Ala Glu Gly Met Ala Phe Ile Glu
            100                 105                 110

Glu Arg Asn Tyr Ile His Arg Asp Leu Arg Ala Ala Asn Ile Leu Val
        115                 120                 125

Ser Asp Thr Leu Ser Cys Lys Ile Ala Asp Phe Gly Leu Ala Arg Leu
    130                 135                 140

Ile Glu Asp Asn Glu Tyr Thr Ala Arg Glu Gly Ala Lys Phe Pro Ile
145                 150                 155                 160

Lys Trp Thr Ala Pro Glu Ala Ile Asn Tyr Gly Thr Phe Thr Ile Lys
                165                 170                 175

Ser Asp Val Trp Ser Phe Gly Ile Leu Leu Thr Glu Ile Val Thr His
            180                 185                 190

Gly Arg Ile Pro Tyr Pro Gly Met Thr Asn Pro Glu Val Ile Gln Asn
        195                 200                 205

Leu Glu Arg Gly Tyr Arg Met Val Arg Pro Asp Asn Cys Pro Glu Glu
    210                 215                 220

Leu Tyr Gln Leu Met Arg Leu Cys Trp Lys Glu Arg Pro Glu Asp Arg
225                 230                 235                 240

Pro Thr Phe Asp Tyr Leu Arg Ser Val Leu Glu Asp Phe Phe
                245                 250
```

```
<210> SEQ ID NO 22
<211> LENGTH: 40
<212> TYPE: PRT
<213> ORGANISM: Artificial Sequence
<220> FEATURE:
<223> OTHER INFORMATION: cytoplasmic tail of CD4

<400> SEQUENCE: 22

Cys Val Arg Cys Arg His Arg Arg Gln Ala Glu Arg Met Ser Gln
1               5                   10                  15

Ile Lys Arg Leu Leu Ser Glu Lys Lys Thr Cys Gln Cys Pro His Arg
                20                  25                  30

Phe Gln Lys Thr Cys Ser Pro Ile
                35                  40

<210> SEQ ID NO 23
<211> LENGTH: 32
<212> TYPE: PRT
<213> ORGANISM: Artificial Sequence
<220> FEATURE:
<223> OTHER INFORMATION: cytoplasmic tail of CD8

<400> SEQUENCE: 23

Leu Tyr Cys Asn His Arg Asn Arg Arg Val Cys Lys Cys Pro Arg
1               5                   10                  15

Pro Val Val Lys Ser Gly Asp Lys Pro Ser Leu Ser Ala Arg Tyr Val
                20                  25                  30

<210> SEQ ID NO 24
<211> LENGTH: 214
<212> TYPE: PRT
<213> ORGANISM: Artificial Sequence
<220> FEATURE:
<223> OTHER INFORMATION: SHP-1 SH2 complete domain

<400> SEQUENCE: 24

Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
                20                  25                  30

Arg Lys Asn Gln Gly Asp Phe Ser Leu Ser Val Arg Val Gly Asp Gln
                35                  40                  45

Val Thr His Ile Arg Ile Gln Asn Ser Gly Asp Phe Tyr Asp Leu Tyr
            50                  55                  60

Gly Gly Glu Lys Phe Ala Thr Leu Thr Glu Leu Val Glu Tyr Tyr Thr
65                  70                  75                  80

Gln Gln Gln Gly Val Leu Gln Asp Arg Asp Gly Thr Ile Ile His Leu
                85                  90                  95

Lys Tyr Pro Leu Asn Cys Ser Asp Pro Thr Ser Glu Arg Trp Tyr His
                100                 105                 110

Gly His Met Ser Gly Gly Gln Ala Glu Thr Leu Leu Gln Ala Lys Gly
            115                 120                 125

Glu Pro Trp Thr Phe Leu Val Arg Glu Ser Leu Ser Gln Pro Gly Asp
            130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175
```

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
            195                 200                 205

Leu Arg Gln Pro Tyr Tyr
        210

<210> SEQ ID NO 25
<211> LENGTH: 97
<212> TYPE: PRT
<213> ORGANISM: Artificial Sequence
<220> FEATURE:
<223> OTHER INFORMATION: SHP-1 SH2 1

<400> SEQUENCE: 25

Trp Phe His Arg Asp Leu Ser Gly Leu Asp Ala Glu Thr Leu Leu Lys
1               5                   10                  15

Gly Arg Gly Val His Gly Ser Phe Leu Ala Arg Pro Ser Arg Lys Asn
            20                  25                  30

Gln Gly Asp Phe Ser Leu Ser Val Arg Val Gly Asp Gln Val Thr His
        35                  40                  45

Ile Arg Ile Gln Asn Ser Gly Asp Phe Tyr Asp Leu Tyr Gly Gly Glu
    50                  55                  60

Lys Phe Ala Thr Leu Thr Glu Leu Val Glu Tyr Tyr Thr Gln Gln Gln
65                  70                  75                  80

Gly Val Leu Gln Asp Arg Asp Gly Thr Ile Ile His Leu Lys Tyr Pro
                85                  90                  95

Leu

<210> SEQ ID NO 26
<211> LENGTH: 104
<212> TYPE: PRT
<213> ORGANISM: Artificial Sequence
<220> FEATURE:
<223> OTHER INFORMATION: SHP-1 SH2 2

<400> SEQUENCE: 26

Trp Tyr His Gly His Met Ser Gly Gly Gln Ala Glu Thr Leu Leu Gln
1               5                   10                  15

Ala Lys Gly Glu Pro Trp Thr Phe Leu Val Arg Glu Ser Leu Ser Gln
            20                  25                  30

Pro Gly Asp Phe Val Leu Ser Val Leu Ser Asp Gln Pro Lys Ala Gly
        35                  40                  45

Pro Gly Ser Pro Leu Arg Val Thr His Ile Lys Val Met Cys Glu Gly
    50                  55                  60

Gly Arg Tyr Thr Val Gly Gly Leu Glu Thr Phe Asp Ser Leu Thr Asp
65                  70                  75                  80

Leu Val Glu His Phe Lys Lys Thr Gly Ile Glu Glu Ala Ser Gly Ala
                85                  90                  95

Phe Val Tyr Leu Arg Gln Pro Tyr
            100

<210> SEQ ID NO 27
<211> LENGTH: 97
<212> TYPE: PRT
<213> ORGANISM: Artificial Sequence
<220> FEATURE:
<223> OTHER INFORMATION: SHP-2 first SH2 domain

<400> SEQUENCE: 27

Trp Phe His Pro Asn Ile Thr Gly Val Glu Ala Glu Asn Leu Leu Leu
1               5                   10                  15

Thr Arg Gly Val Asp Gly Ser Phe Leu Ala Arg Pro Ser Lys Ser Asn
                20                  25                  30

Pro Gly Asp Phe Thr Leu Ser Val Arg Arg Asn Gly Ala Val Thr His
            35                  40                  45

Ile Lys Ile Gln Asn Thr Gly Asp Tyr Tyr Asp Leu Tyr Gly Gly Glu
        50                  55                  60

Lys Phe Ala Thr Leu Ala Glu Leu Val Gln Tyr Tyr Met Glu His His
65                  70                  75                  80

Gly Gln Leu Lys Glu Lys Asn Gly Asp Val Ile Glu Leu Lys Tyr Pro
                85                  90                  95

Leu

<210> SEQ ID NO 28
<211> LENGTH: 105
<212> TYPE: PRT
<213> ORGANISM: Artificial Sequence
<220> FEATURE:
<223> OTHER INFORMATION: SHP-2 second SH2 domain

<400> SEQUENCE: 28

Trp Phe His Gly His Leu Ser Gly Lys Glu Ala Glu Lys Leu Leu Thr
1               5                   10                  15

Glu Lys Gly Lys His Gly Ser Phe Leu Val Arg Glu Ser Gln Ser His
                20                  25                  30

Pro Gly Asp Phe Val Leu Ser Val Arg Thr Gly Asp Asp Lys Gly Glu
            35                  40                  45

Ser Asn Asp Gly Lys Ser Lys Val Thr His Val Met Ile Arg Cys Gln
        50                  55                  60

Glu Leu Lys Tyr Asp Val Gly Gly Gly Glu Arg Phe Asp Ser Leu Thr
65                  70                  75                  80

Asp Leu Val Glu His Tyr Lys Lys Asn Pro Met Val Glu Thr Leu Gly
                85                  90                  95

Thr Val Leu Gln Leu Lys Gln Pro Leu
            100                 105

<210> SEQ ID NO 29
<211> LENGTH: 211
<212> TYPE: PRT
<213> ORGANISM: Artificial Sequence
<220> FEATURE:
<223> OTHER INFORMATION: SHP-2 both SH2 domains

<400> SEQUENCE: 29

Trp Phe His Pro Asn Ile Thr Gly Val Glu Ala Glu Asn Leu Leu Leu
1               5                   10                  15

Thr Arg Gly Val Asp Gly Ser Phe Leu Ala Arg Pro Ser Lys Ser Asn
                20                  25                  30

Pro Gly Asp Phe Thr Leu Ser Val Arg Arg Asn Gly Ala Val Thr His
            35                  40                  45

Ile Lys Ile Gln Asn Thr Gly Asp Tyr Tyr Asp Leu Tyr Gly Gly Glu
        50                  55                  60

Lys Phe Ala Thr Leu Ala Glu Leu Val Gln Tyr Tyr Met Glu His His
65                  70                  75                  80

Gly Gln Leu Lys Glu Lys Asn Gly Asp Val Ile Glu Leu Lys Tyr Pro
                85                  90                  95

```
Leu Asn Cys Ala Asp Pro Thr Ser Glu Arg Trp Phe His Gly His Leu
            100                 105                 110

Ser Gly Lys Glu Ala Glu Lys Leu Thr Glu Lys Gly Lys His Gly
        115                 120                 125

Ser Phe Leu Val Arg Glu Ser Gln Ser His Pro Gly Asp Phe Val Leu
        130                 135                 140

Ser Val Arg Thr Gly Asp Asp Lys Gly Glu Ser Asn Asp Gly Lys Ser
145                 150                 155                 160

Lys Val Thr His Val Met Ile Arg Cys Gln Glu Leu Lys Tyr Asp Val
                165                 170                 175

Gly Gly Gly Glu Arg Phe Asp Ser Leu Thr Asp Leu Val Glu His Tyr
                180                 185                 190

Lys Lys Asn Pro Met Val Glu Thr Leu Gly Thr Val Leu Gln Leu Lys
            195                 200                 205

Gln Pro Leu
    210

<210> SEQ ID NO 30
<211> LENGTH: 107
<212> TYPE: PRT
<213> ORGANISM: Artificial Sequence
<220> FEATURE:
<223> OTHER INFORMATION: Human Light Kappa Chain

<400> SEQUENCE: 30

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 31
<211> LENGTH: 19
<212> TYPE: PRT
<213> ORGANISM: Artificial Sequence
<220> FEATURE:
<223> OTHER INFORMATION: Human Hinge

<400> SEQUENCE: 31

Glu Pro Lys Ser Cys Asp Lys Thr His Thr Cys Pro Pro Cys Pro Lys
1               5                   10                  15

Asp Pro Lys

<210> SEQ ID NO 32
<211> LENGTH: 97
<212> TYPE: PRT
<213> ORGANISM: Artificial Sequence
<220> FEATURE:
<223> OTHER INFORMATION: Human CH1
```

```
<400> SEQUENCE: 32

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
                20                  25                  30

Pro Glu Pro Val Thr Val Ser Trp Asn Ser Gly Ala Leu Thr Ser Gly
            35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Arg
                85                  90                  95

Val

<210> SEQ ID NO 33
<211> LENGTH: 21
<212> TYPE: PRT
<213> ORGANISM: Artificial Sequence
<220> FEATURE:
<223> OTHER INFORMATION: Transmembrane domain from human IL2R common
      gamma chain

<400> SEQUENCE: 33

Val Val Ile Ser Val Gly Ser Met Gly Leu Ile Ile Ser Leu Leu Cys
1               5                   10                  15

Val Tyr Phe Trp Leu
            20

<210> SEQ ID NO 34
<211> LENGTH: 25
<212> TYPE: PRT
<213> ORGANISM: Artificial Sequence
<220> FEATURE:
<223> OTHER INFORMATION: Transmembrane domain from human IL-2R beta

<400> SEQUENCE: 34

Ile Pro Trp Leu Gly His Leu Leu Val Gly Leu Ser Gly Ala Phe Gly
1               5                   10                  15

Phe Ile Ile Leu Val Tyr Leu Leu Ile
            20                  25

<210> SEQ ID NO 35

<400> SEQUENCE: 35

000

<210> SEQ ID NO 36
<211> LENGTH: 25
<212> TYPE: PRT
<213> ORGANISM: Artificial Sequence
<220> FEATURE:
<223> OTHER INFORMATION: Transmembrane domain from human IL-7R alpha

<400> SEQUENCE: 36

Pro Ile Leu Leu Thr Ile Ser Ile Leu Ser Phe Phe Ser Val Ala Leu
1               5                   10                  15

Leu Val Ile Leu Ala Cys Val Leu Trp
            20                  25
```

-continued

```
<210> SEQ ID NO 37
<211> LENGTH: 26
<212> TYPE: PRT
<213> ORGANISM: Artificial Sequence
<220> FEATURE:
<223> OTHER INFORMATION: Transmembrane domain from Human GF-CSFR alpha

<400> SEQUENCE: 37

Asn Leu Gly Ser Val Tyr Ile Tyr Val Leu Leu Ile Val Gly Thr Leu
1               5                   10                  15

Val Cys Gly Ile Val Leu Gly Phe Leu Phe
            20                  25

<210> SEQ ID NO 38
<211> LENGTH: 17
<212> TYPE: PRT
<213> ORGANISM: Artificial Sequence
<220> FEATURE:
<223> OTHER INFORMATION: Transmembrane domain from Human GM-CSFR common
      beta chain

<400> SEQUENCE: 38

Val Leu Ala Leu Ile Val Ile Phe Leu Thr Ile Ala Val Leu Leu Ala
1               5                   10                  15

Leu

<210> SEQ ID NO 39
<211> LENGTH: 86
<212> TYPE: PRT
<213> ORGANISM: Artificial Sequence
<220> FEATURE:
<223> OTHER INFORMATION: Endodomain from human IL2R common gamma chain

<400> SEQUENCE: 39

Glu Arg Thr Met Pro Arg Ile Pro Thr Leu Lys Asn Leu Glu Asp Leu
1               5                   10                  15

Val Thr Glu Tyr His Gly Asn Phe Ser Ala Trp Ser Gly Val Ser Lys
            20                  25                  30

Gly Leu Ala Glu Ser Leu Gln Pro Asp Tyr Ser Glu Arg Leu Cys Leu
        35                  40                  45

Val Ser Glu Ile Pro Pro Lys Gly Gly Ala Leu Gly Glu Gly Pro Gly
    50                  55                  60

Ala Ser Pro Cys Asn Gln His Ser Pro Tyr Trp Ala Pro Pro Cys Tyr
65                  70                  75                  80

Thr Leu Lys Pro Glu Thr
                85

<210> SEQ ID NO 40
<211> LENGTH: 286
<212> TYPE: PRT
<213> ORGANISM: Artificial Sequence
<220> FEATURE:
<223> OTHER INFORMATION: Endodomain from human IL-2R beta

<400> SEQUENCE: 40

Asn Cys Arg Asn Thr Gly Pro Trp Leu Lys Lys Val Leu Lys Cys Asn
1               5                   10                  15

Thr Pro Asp Pro Ser Lys Phe Phe Ser Gln Leu Ser Ser Glu His Gly
            20                  25                  30

Gly Asp Val Gln Lys Trp Leu Ser Ser Pro Phe Pro Ser Ser Ser Phe
        35                  40                  45

Ser Pro Gly Gly Leu Ala Pro Glu Ile Ser Pro Leu Glu Val Leu Glu
```

```
             50                  55                  60
Arg Asp Lys Val Thr Gln Leu Leu Gln Gln Asp Lys Val Pro Glu
 65                  70                  75                  80

Pro Ala Ser Leu Ser Ser Asn His Ser Leu Thr Ser Cys Phe Thr Asn
                 85                  90                  95

Gln Gly Tyr Phe Phe His Leu Pro Asp Ala Leu Glu Ile Glu Ala
                100                 105                 110

Cys Gln Val Tyr Phe Thr Tyr Asp Pro Tyr Ser Glu Glu Asp Pro Asp
                115                 120                 125

Glu Gly Val Ala Gly Ala Pro Thr Gly Ser Ser Pro Gln Pro Leu Gln
130                 135                 140

Pro Leu Ser Gly Glu Asp Asp Ala Tyr Cys Thr Phe Pro Ser Arg Asp
145                 150                 155                 160

Asp Leu Leu Leu Phe Ser Pro Ser Leu Leu Gly Gly Pro Ser Pro Pro
                165                 170                 175

Ser Thr Ala Pro Gly Gly Ser Gly Ala Gly Glu Glu Arg Met Pro Pro
                180                 185                 190

Ser Leu Gln Glu Arg Val Pro Arg Asp Trp Asp Pro Gln Pro Leu Gly
                195                 200                 205

Pro Pro Thr Pro Gly Val Pro Asp Leu Val Asp Phe Gln Pro Pro Pro
210                 215                 220

Glu Leu Val Leu Arg Glu Ala Gly Glu Glu Val Pro Asp Ala Gly Pro
225                 230                 235                 240

Arg Glu Gly Val Ser Phe Pro Trp Ser Arg Pro Pro Gly Gln Gly Glu
                245                 250                 255

Phe Arg Ala Leu Asn Ala Arg Leu Pro Leu Asn Thr Asp Ala Tyr Leu
                260                 265                 270

Ser Leu Gln Glu Leu Gln Gly Gln Asp Pro Thr His Leu Val
                275                 280                 285

<210> SEQ ID NO 41
<211> LENGTH: 196
<212> TYPE: PRT
<213> ORGANISM: Artificial Sequence
<220> FEATURE:
<223> OTHER INFORMATION: Endodomain from human IL-7R alpha

<400> SEQUENCE: 41

Lys Lys Arg Ile Lys Pro Ile Val Trp Pro Ser Leu Pro Asp His Lys
 1               5                  10                  15

Lys Thr Leu Glu His Leu Cys Lys Lys Pro Arg Lys Asn Leu Asn Val
                20                  25                  30

Ser Phe Asn Pro Glu Ser Phe Leu Asp Cys Gln Ile His Arg Val Asp
                35                  40                  45

Asp Ile Gln Ala Arg Asp Glu Val Glu Gly Phe Leu Gln Asp Thr Phe
 50                  55                  60

Pro Gln Gln Leu Glu Glu Ser Glu Lys Gln Arg Leu Gly Gly Asp Val
 65                  70                  75                  80

Gln Ser Pro Asn Cys Pro Ser Glu Asp Val Val Ile Thr Pro Glu Ser
                85                  90                  95

Phe Gly Arg Asp Ser Ser Leu Thr Cys Leu Ala Gly Asn Val Ser Ala
                100                 105                 110

Cys Asp Ala Pro Ile Leu Ser Ser Ser Arg Ser Leu Asp Cys Arg Glu
                115                 120                 125

Ser Gly Lys Asn Gly Pro His Val Tyr Gln Asp Leu Leu Leu Ser Leu
```

```
                130                 135                 140
Gly Thr Thr Asn Ser Thr Leu Pro Pro Phe Ser Leu Gln Ser Gly
145                 150                 155                 160

Ile Leu Thr Leu Asn Pro Val Ala Gln Gly Gln Pro Ile Leu Thr Ser
                165                 170                 175

Leu Gly Ser Asn Gln Glu Glu Ala Tyr Val Thr Met Ser Ser Phe Tyr
            180                 185                 190

Gln Asn Glu Gln
        195

<210> SEQ ID NO 42
<211> LENGTH: 54
<212> TYPE: PRT
<213> ORGANISM: Artificial Sequence
<220> FEATURE:
<223> OTHER INFORMATION: Endodomain Derived from Human GM-CSFR alpha

<400> SEQUENCE: 42

Lys Arg Phe Leu Arg Ile Gln Arg Leu Phe Pro Pro Val Pro Gln Ile
1               5                   10                  15

Lys Asp Lys Leu Asn Asp Asn His Glu Val Glu Asp Glu Ile Ile Trp
            20                  25                  30

Glu Glu Phe Thr Pro Glu Glu Gly Lys Gly Tyr Arg Glu Glu Val Leu
        35                  40                  45

Thr Val Lys Glu Ile Thr
    50

<210> SEQ ID NO 43
<211> LENGTH: 437
<212> TYPE: PRT
<213> ORGANISM: Artificial Sequence
<220> FEATURE:
<223> OTHER INFORMATION: Endodomain from GM-CSFR common beta chain

<400> SEQUENCE: 43

Arg Phe Cys Gly Ile Tyr Gly Tyr Arg Leu Arg Arg Lys Trp Glu Glu
1               5                   10                  15

Lys Ile Pro Asn Pro Ser Lys Ser His Leu Phe Gln Asn Gly Ser Ala
            20                  25                  30

Glu Leu Trp Pro Pro Gly Ser Met Ser Ala Phe Thr Ser Gly Ser Pro
        35                  40                  45

Pro His Gln Gly Pro Trp Gly Ser Arg Phe Pro Glu Leu Glu Gly Val
    50                  55                  60

Phe Pro Val Gly Phe Gly Asp Ser Glu Val Ser Pro Leu Thr Ile Glu
65                  70                  75                  80

Asp Pro Lys His Val Cys Asp Pro Pro Ser Gly Pro Asp Thr Thr Pro
                85                  90                  95

Ala Ala Ser Asp Leu Pro Thr Glu Gln Pro Pro Ser Pro Gln Pro Gly
            100                 105                 110

Pro Pro Ala Ala Ser His Thr Pro Glu Lys Gln Ala Ser Ser Phe Asp
        115                 120                 125

Phe Asn Gly Pro Tyr Leu Gly Pro Pro His Ser Arg Ser Leu Pro Asp
    130                 135                 140

Ile Leu Gly Gln Pro Glu Pro Pro Gln Glu Gly Gly Ser Gln Lys Ser
145                 150                 155                 160

Pro Pro Pro Gly Ser Leu Glu Tyr Leu Cys Leu Pro Ala Gly Gly Gln
                165                 170                 175
```

Val Gln Leu Val Pro Leu Ala Gln Ala Met Gly Pro Gly Gln Ala Val
            180                 185                 190

Glu Val Glu Arg Arg Pro Ser Gln Gly Ala Ala Gly Ser Pro Ser Leu
        195                 200                 205

Glu Ser Gly Gly Pro Ala Pro Ala Leu Gly Pro Arg Val Gly
    210                 215                 220

Gly Gln Asp Gln Lys Asp Ser Pro Val Ala Ile Pro Met Ser Ser Gly
225                 230                 235                 240

Asp Thr Glu Asp Pro Gly Val Ala Ser Gly Tyr Val Ser Ala Asp
                245                 250                 255

Leu Val Phe Thr Pro Asn Ser Gly Ala Ser Ser Val Ser Leu Val Pro
            260                 265                 270

Ser Leu Gly Leu Pro Ser Asp Gln Thr Pro Ser Leu Cys Pro Gly Leu
        275                 280                 285

Ala Ser Gly Pro Pro Gly Ala Pro Gly Pro Val Lys Ser Gly Phe Glu
        290                 295                 300

Gly Tyr Val Glu Leu Pro Pro Ile Glu Gly Arg Ser Pro Arg Ser Pro
305                 310                 315                 320

Arg Asn Asn Pro Val Pro Pro Glu Ala Lys Ser Pro Val Leu Asn Pro
                325                 330                 335

Gly Glu Arg Pro Ala Asp Val Ser Pro Thr Ser Pro Gln Pro Glu Gly
            340                 345                 350

Leu Leu Val Leu Gln Gln Val Gly Asp Tyr Cys Phe Leu Pro Gly Leu
        355                 360                 365

Gly Pro Gly Pro Leu Ser Leu Arg Ser Lys Pro Ser Ser Pro Gly Pro
370                 375                 380

Gly Pro Glu Ile Lys Asn Leu Asp Gln Ala Phe Gln Val Lys Lys Pro
385                 390                 395                 400

Pro Gly Gln Ala Val Pro Gln Val Pro Val Ile Gln Leu Phe Lys Ala
                405                 410                 415

Leu Lys Gln Gln Asp Tyr Leu Ser Leu Pro Pro Trp Glu Val Asn Lys
            420                 425                 430

Pro Gly Glu Val Cys
        435

<210> SEQ ID NO 44
<211> LENGTH: 112
<212> TYPE: PRT
<213> ORGANISM: Artificial Sequence
<220> FEATURE:
<223> OTHER INFORMATION: mature protein of wild-type TGFbeta2

<400> SEQUENCE: 44

Ala Leu Asp Ala Ala Tyr Cys Phe Arg Asn Val Gln Asp Asn Cys Cys
1               5                   10                  15

Leu Arg Pro Leu Tyr Ile Asp Phe Lys Arg Asp Leu Gly Trp Lys Trp
            20                  25                  30

Ile His Glu Pro Lys Gly Tyr Asn Ala Asn Phe Cys Ala Gly Ala Cys
        35                  40                  45

Pro Tyr Leu Trp Ser Ser Asp Thr Gln His Ser Arg Val Leu Ser Leu
    50                  55                  60

Tyr Asn Thr Ile Asn Pro Glu Ala Ser Ala Ser Pro Cys Cys Val Ser
65                  70                  75                  80

Gln Asp Leu Glu Pro Leu Thr Ile Leu Tyr Tyr Ile Gly Lys Thr Pro
                85                  90                  95

```
Lys Ile Glu Gln Leu Ser Asn Met Ile Val Lys Ser Cys Lys Cys Ser
            100                 105                 110
```

<210> SEQ ID NO 45
<211> LENGTH: 394
<212> TYPE: PRT
<213> ORGANISM: Artificial Sequence
<220> FEATURE:
<223> OTHER INFORMATION: TGFbeta monomer sequence

<400> SEQUENCE: 45

```
Met His Tyr Cys Val Leu Ser Ala Phe Leu Ile Leu His Leu Val Thr
1               5                   10                  15

Val Ala Leu Ser Leu Ser Thr Cys Ser Thr Leu Asp Met Asp Gln Phe
            20                  25                  30

Met Arg Lys Arg Ile Glu Ala Ile Arg Gly Gln Ile Leu Ser Lys Leu
        35                  40                  45

Lys Leu Thr Ser Pro Pro Glu Asp Tyr Pro Glu Pro Glu Glu Val Pro
50                  55                  60

Pro Glu Val Ile Ser Ile Tyr Asn Ser Thr Arg Asp Leu Leu Gln Glu
65                  70                  75                  80

Lys Ala Ser Arg Arg Ala Ala Ala Cys Glu Arg Glu Arg Ser Asp Glu
                85                  90                  95

Glu Tyr Tyr Ala Lys Glu Val Tyr Lys Ile Asp Met Pro Pro Phe Phe
            100                 105                 110

Pro Ser Glu Asn Ala Ile Pro Pro Thr Phe Tyr Arg Pro Tyr Phe Arg
        115                 120                 125

Ile Val Arg Phe Asp Val Ser Ala Met Glu Lys Asn Ala Ser Asn Leu
130                 135                 140

Val Lys Ala Glu Phe Arg Val Phe Arg Leu Gln Asn Pro Lys Ala Arg
145                 150                 155                 160

Val Pro Glu Gln Arg Ile Glu Leu Tyr Gln Ile Leu Lys Ser Lys Asp
                165                 170                 175

Leu Thr Ser Pro Thr Gln Arg Tyr Ile Asp Ser Lys Val Val Lys Thr
            180                 185                 190

Arg Ala Glu Gly Glu Trp Leu Ser Phe Asp Val Thr Asp Ala Val His
        195                 200                 205

Glu Trp Leu His His Lys Asp Arg Asn Leu Gly Phe Lys Ile Ser Leu
210                 215                 220

His Cys Pro Cys Cys Thr Phe Val Pro Ser Asn Asn Tyr Ile Ile Pro
225                 230                 235                 240

Asn Lys Ser Glu Glu Leu Glu Ala Arg Phe Ala Gly Ile Asp Gly Thr
                245                 250                 255

Ser Thr Tyr Thr Ser Gly Asp Gln Lys Thr Ile Lys Ser Thr Arg Lys
            260                 265                 270

Lys Asn Ser Gly Lys Thr Pro His Leu Leu Leu Met Leu Leu Pro Ser
        275                 280                 285

Tyr Arg Leu Glu Ser Gln Gln Thr Asn Arg Arg Lys Lys Arg Ala Leu
290                 295                 300

Asp Ala Ala Tyr Cys Phe Arg Asn Val Gln Asp Asn Cys Cys Leu Arg
305                 310                 315                 320

Pro Leu Tyr Ile Asp Phe Arg Lys Asp Leu Gly Trp Lys Trp Ile His
                325                 330                 335

Glu Pro Lys Gly Tyr Asn Ala Asn Phe Cys Ala Gly Ala Cys Pro Tyr
            340                 345                 350
```

```
Arg Ala Ser Lys Ser Pro Ser Cys Val Ser Gln Asp Leu Glu Pro Leu
        355                 360                 365

Thr Ile Val Tyr Tyr Val Gly Arg Lys Pro Lys Val Glu Gln Leu Ser
    370                 375                 380

Asn Met Ile Val Lys Ser Cys Lys Cys Ser
385                 390

<210> SEQ ID NO 46
<211> LENGTH: 177
<212> TYPE: PRT
<213> ORGANISM: Artificial Sequence
<220> FEATURE:
<223> OTHER INFORMATION: dominant-negative TGFbeta RII (dnTGFbeta RII)

<400> SEQUENCE: 46

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Leu Leu Leu Val Ile Phe Gln
    130                 135                 140

Val Thr Gly Ile Ser Leu Leu Pro Pro Leu Gly Val Ala Ile Ser Val
145                 150                 155                 160

Ile Ile Ile Phe Tyr Cys Tyr Arg Val Asn Arg Gln Gln Lys Leu Ser
                165                 170                 175

Ser

<210> SEQ ID NO 47
<211> LENGTH: 194
<212> TYPE: PRT
<213> ORGANISM: Artificial Sequence
<220> FEATURE:
<223> OTHER INFORMATION: MH2 domain of SMAD2

<400> SEQUENCE: 47

Trp Cys Ser Ile Ala Tyr Tyr Glu Leu Asn Gln Arg Val Gly Glu Thr
1               5                   10                  15

Phe His Ala Ser Gln Pro Ser Leu Thr Val Asp Gly Phe Thr Asp Pro
            20                  25                  30

Ser Asn Ser Glu Arg Phe Cys Leu Gly Leu Leu Ser Asn Val Asn Arg
        35                  40                  45

Asn Ala Thr Val Glu Met Thr Arg Arg His Ile Gly Arg Gly Val Arg
    50                  55                  60

Leu Tyr Tyr Ile Gly Gly Glu Val Phe Ala Glu Cys Leu Ser Asp Ser
65                  70                  75                  80
```

```
Ala Ile Phe Val Gln Ser Pro Asn Cys Asn Gln Arg Tyr Gly Trp His
                85                  90                  95

Pro Ala Thr Val Cys Lys Ile Pro Pro Gly Cys Asn Leu Lys Ile Phe
            100                 105                 110

Asn Asn Gln Glu Phe Ala Ala Leu Leu Ala Gln Ser Val Asn Gln Gly
        115                 120                 125

Phe Glu Ala Val Tyr Gln Leu Thr Arg Met Cys Thr Ile Arg Met Ser
130                 135                 140

Phe Val Lys Gly Trp Gly Ala Glu Tyr Arg Arg Gln Thr Val Thr Ser
145                 150                 155                 160

Thr Pro Cys Trp Ile Glu Leu His Leu Asn Gly Pro Leu Gln Trp Leu
                165                 170                 175

Asp Lys Val Leu Thr Gln Met Gly Ser Pro Ser Val Arg Cys Ser Ser
            180                 185                 190

Met Ser

<210> SEQ ID NO 48
<211> LENGTH: 194
<212> TYPE: PRT
<213> ORGANISM: Artificial Sequence
<220> FEATURE:
<223> OTHER INFORMATION: MH2 domain of SMAD3

<400> SEQUENCE: 48

Trp Cys Ser Ile Ser Tyr Tyr Glu Leu Asn Gln Arg Val Gly Glu Thr
1               5                   10                  15

Phe His Ala Ser Gln Pro Ser Met Thr Val Asp Gly Phe Thr Asp Pro
            20                  25                  30

Ser Asn Ser Glu Arg Phe Cys Leu Gly Leu Leu Ser Asn Val Asn Arg
        35                  40                  45

Asn Ala Ala Val Glu Leu Thr Arg Arg His Ile Gly Arg Gly Val Arg
    50                  55                  60

Leu Tyr Tyr Ile Gly Gly Glu Val Phe Ala Glu Cys Leu Ser Asp Ser
65                  70                  75                  80

Ala Ile Phe Val Gln Ser Pro Asn Cys Asn Gln Arg Tyr Gly Trp His
                85                  90                  95

Pro Ala Thr Val Cys Lys Ile Pro Pro Gly Cys Asn Leu Lys Ile Phe
            100                 105                 110

Asn Asn Gln Glu Phe Ala Ala Leu Leu Ala Gln Ser Val Asn Gln Gly
        115                 120                 125

Phe Glu Ala Val Tyr Gln Leu Thr Arg Met Cys Thr Ile Arg Met Ser
130                 135                 140

Phe Val Lys Gly Trp Gly Ala Glu Tyr Arg Arg Gln Thr Val Thr Ser
145                 150                 155                 160

Thr Pro Cys Trp Ile Glu Leu His Leu Asn Gly Pro Leu Gln Trp Leu
                165                 170                 175

Asp Lys Val Leu Thr Gln Met Gly Ser Pro Ser Ile Arg Cys Ser Ser
            180                 185                 190

Val Ser

<210> SEQ ID NO 49
<211> LENGTH: 230
<212> TYPE: PRT
<213> ORGANISM: Artificial Sequence
<220> FEATURE:
<223> OTHER INFORMATION: MH2 domain of SMAD4
```

```
<400> SEQUENCE: 49

Trp Cys Ser Ile Ala Tyr Phe Glu Met Asp Val Gln Val Gly Glu Thr
1               5                   10                  15

Phe Lys Val Pro Ser Ser Cys Pro Ile Val Thr Val Asp Gly Tyr Val
            20                  25                  30

Asp Pro Ser Gly Gly Asp Arg Phe Cys Leu Gly Gln Leu Ser Asn Val
        35                  40                  45

His Arg Thr Glu Ala Ile Glu Arg Ala Arg Leu His Ile Gly Lys Gly
    50                  55                  60

Val Gln Leu Glu Cys Lys Gly Glu Gly Asp Val Trp Val Arg Cys Leu
65                  70                  75                  80

Ser Asp His Ala Val Phe Val Gln Ser Tyr Tyr Leu Asp Arg Glu Ala
                85                  90                  95

Gly Arg Ala Pro Gly Asp Ala Val His Lys Ile Tyr Pro Ser Ala Tyr
            100                 105                 110

Ile Lys Val Phe Asp Leu Arg Gln Cys His Arg Gln Met Gln Gln Gln
        115                 120                 125

Ala Ala Thr Ala Gln Ala Ala Ala Ala Gln Ala Ala Ala Val Ala
    130                 135                 140

Gly Asn Ile Pro Gly Pro Gly Ser Val Gly Gly Ile Ala Pro Ala Ile
145                 150                 155                 160

Ser Leu Ser Ala Ala Ala Gly Ile Gly Val Asp Asp Leu Arg Arg Leu
                165                 170                 175

Cys Ile Leu Arg Met Ser Phe Val Lys Gly Trp Gly Pro Asp Tyr Pro
            180                 185                 190

Arg Gln Ser Ile Lys Glu Thr Pro Cys Trp Ile Glu Ile His Leu His
        195                 200                 205

Arg Ala Leu Gln Leu Leu Asp Glu Val Leu His Thr Met Pro Ile Ala
    210                 215                 220

Asp Pro Gln Pro Leu Asp
225                 230

<210> SEQ ID NO 50
<211> LENGTH: 380
<212> TYPE: PRT
<213> ORGANISM: Artificial Sequence
<220> FEATURE:
<223> OTHER INFORMATION: chimeric dnSMAD comprising a dnSMAD2
      polypeptide and a dnSMAD3 polypeptide

<400> SEQUENCE: 50

Trp Cys Ser Ile Ala Tyr Tyr Glu Leu Asn Gln Arg Val Gly Glu Thr
1               5                   10                  15

Phe His Ala Ser Gln Pro Ser Leu Thr Val Asp Gly Phe Thr Asp Pro
            20                  25                  30

Ser Asn Ser Glu Arg Phe Cys Leu Gly Leu Leu Ser Asn Val Asn Arg
        35                  40                  45

Asn Ala Thr Val Glu Met Thr Arg Arg His Ile Gly Arg Gly Val Arg
    50                  55                  60

Leu Tyr Tyr Ile Gly Gly Glu Val Phe Ala Glu Cys Leu Ser Asp Ser
65                  70                  75                  80

Ala Ile Phe Val Gln Ser Pro Asn Cys Asn Gln Arg Tyr Gly Trp His
                85                  90                  95

Pro Ala Thr Val Cys Lys Ile Pro Pro Gly Cys Asn Leu Lys Ile Phe
            100                 105                 110
```

```
Asn Asn Gln Glu Phe Ala Ala Leu Leu Ala Gln Ser Val Asn Gln Gly
            115                 120                 125

Phe Glu Ala Val Tyr Gln Leu Thr Arg Met Cys Thr Ile Arg Met Ser
    130                 135                 140

Phe Val Lys Gly Trp Gly Ala Glu Tyr Arg Arg Gln Thr Val Thr Ser
145                 150                 155                 160

Thr Pro Cys Trp Ile Glu Leu His Leu Asn Gly Pro Leu Gln Trp Leu
                165                 170                 175

Asp Lys Val Leu Thr Gln Met Leu Glu Tyr Ser Gly Gly Ser Gly
            180                 185                 190

Gly Gly Ser Leu Glu Trp Cys Ser Ile Ser Tyr Tyr Glu Leu Asn Gln
            195                 200                 205

Arg Val Gly Glu Thr Phe His Ala Ser Gln Pro Ser Met Thr Val Asp
            210                 215                 220

Gly Phe Thr Asp Pro Ser Asn Ser Glu Arg Phe Cys Leu Gly Leu Leu
225                 230                 235                 240

Ser Asn Val Asn Arg Asn Ala Ala Val Glu Leu Thr Arg Arg His Ile
                245                 250                 255

Gly Arg Gly Val Arg Leu Tyr Tyr Ile Gly Gly Glu Val Phe Ala Glu
            260                 265                 270

Cys Leu Ser Asp Ser Ala Ile Phe Val Gln Ser Pro Asn Cys Asn Gln
            275                 280                 285

Arg Tyr Gly Trp His Pro Ala Thr Val Cys Lys Ile Pro Pro Gly Cys
            290                 295                 300

Asn Leu Lys Ile Phe Asn Asn Gln Glu Phe Ala Ala Leu Leu Ala Gln
305                 310                 315                 320

Ser Val Asn Gln Gly Phe Glu Ala Val Tyr Gln Leu Thr Arg Met Cys
                325                 330                 335

Thr Ile Arg Met Ser Phe Val Lys Gly Trp Gly Ala Glu Tyr Arg Arg
            340                 345                 350

Gln Thr Val Thr Ser Thr Pro Cys Trp Ile Glu Leu His Leu Asn Gly
            355                 360                 365

Pro Leu Gln Trp Leu Asp Lys Val Leu Thr Gln Met
            370                 375                 380

<210> SEQ ID NO 51
<211> LENGTH: 271
<212> TYPE: PRT
<213> ORGANISM: Artificial Sequence
<220> FEATURE:
<223> OTHER INFORMATION: chimeric TNF receptor HVEM-41BB

<400> SEQUENCE: 51

Met Glu Pro Pro Gly Asp Trp Gly Pro Pro Trp Arg Ser Thr Pro
1               5                   10                  15

Arg Thr Asp Val Leu Arg Leu Val Leu Tyr Leu Thr Phe Leu Gly Ala
            20                  25                  30

Pro Cys Tyr Ala Pro Ala Leu Pro Ser Cys Lys Glu Asp Glu Tyr Pro
        35                  40                  45

Val Gly Ser Glu Cys Cys Pro Lys Cys Ser Pro Gly Tyr Arg Val Lys
    50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95
```

```
Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Ile Ile Ser Phe Phe Leu
        195                 200                 205

Ala Leu Thr Ser Thr Ala Leu Leu Phe Leu Leu Phe Phe Leu Thr Leu
    210                 215                 220

Arg Phe Ser Val Val Lys Arg Gly Arg Lys Lys Leu Leu Tyr Ile Phe
225                 230                 235                 240

Lys Gln Pro Phe Met Arg Pro Val Gln Thr Thr Gln Glu Glu Asp Gly
                245                 250                 255

Cys Ser Cys Arg Phe Pro Glu Glu Glu Glu Gly Gly Cys Glu Leu
            260                 265                 270

<210> SEQ ID NO 52
<211> LENGTH: 260
<212> TYPE: PRT
<213> ORGANISM: Artificial Sequence
<220> FEATURE:
<223> OTHER INFORMATION: chimeric TNF receptor CD27-41BB

<400> SEQUENCE: 52

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190
```

```
Ile Ser Phe Phe Leu Ala Leu Thr Ser Thr Ala Leu Leu Phe Leu Leu
        195                 200                 205

Phe Phe Leu Thr Leu Arg Phe Ser Val Val Lys Arg Gly Arg Lys Lys
210                 215                 220

Leu Leu Tyr Ile Phe Lys Gln Pro Phe Met Arg Pro Val Gln Thr Thr
225                 230                 235                 240

Gln Glu Glu Asp Gly Cys Ser Cys Arg Phe Pro Glu Glu Glu Glu Gly
                245                 250                 255

Gly Cys Glu Leu
        260

<210> SEQ ID NO 53
<211> LENGTH: 281
<212> TYPE: PRT
<213> ORGANISM: Artificial Sequence
<220> FEATURE:
<223> OTHER INFORMATION: chimeric TNF receptor RANK-41BB

<400> SEQUENCE: 53

Met Ala Pro Arg Ala Arg Arg Arg Arg Pro Leu Phe Ala Leu Leu Leu
1               5                   10                  15

Leu Cys Ala Leu Leu Ala Arg Leu Gln Val Ala Leu Gln Ile Ala Pro
            20                  25                  30

Pro Cys Thr Ser Glu Lys His Tyr Glu His Leu Gly Arg Cys Cys Asn
        35                  40                  45

Lys Cys Glu Pro Gly Lys Tyr Met Ser Ser Lys Cys Thr Thr Thr Ser
    50                  55                  60

Asp Ser Val Cys Leu Pro Cys Gly Pro Asp Glu Tyr Leu Asp Ser Trp
65                  70                  75                  80

Asn Glu Glu Asp Lys Cys Leu Leu His Lys Val Cys Asp Thr Gly Lys
                85                  90                  95

Ala Leu Val Ala Val Val Ala Gly Asn Ser Thr Thr Pro Arg Arg Cys
            100                 105                 110

Ala Cys Thr Ala Gly Tyr His Trp Ser Gln Asp Cys Glu Cys Cys Arg
        115                 120                 125

Arg Asn Thr Glu Cys Ala Pro Gly Leu Gly Ala Gln His Pro Leu Gln
    130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
                165                 170                 175

Phe Leu Gly Lys Arg Val Glu His His Gly Thr Glu Lys Ser Asp Ala
            180                 185                 190

Val Cys Ser Ser Ser Leu Pro Ala Arg Lys Pro Pro Asn Glu Pro His
        195                 200                 205

Val Tyr Leu Pro Ile Ile Ser Phe Phe Leu Ala Leu Thr Ser Thr Ala
    210                 215                 220

Leu Leu Phe Leu Leu Phe Phe Leu Thr Leu Arg Phe Ser Val Val Lys
225                 230                 235                 240

Arg Gly Arg Lys Lys Leu Leu Tyr Ile Phe Lys Gln Pro Phe Met Arg
                245                 250                 255

Pro Val Gln Thr Thr Gln Glu Glu Asp Gly Cys Ser Cys Arg Phe Pro
            260                 265                 270

Glu Glu Glu Glu Gly Gly Cys Glu Leu
        275                 280
```

<210> SEQ ID NO 54
<211> LENGTH: 149
<212> TYPE: PRT
<213> ORGANISM: Artificial Sequence
<220> FEATURE:
<223> OTHER INFORMATION: chimeric TNF receptor Fn14-41BB

<400> SEQUENCE: 54

```
Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
                20                  25                  30

Thr Ala Pro Cys Ser Arg Gly Ser Ser Trp Ser Ala Asp Leu Asp Lys
            35                  40                  45

Cys Met Asp Cys Ala Ser Cys Arg Ala Arg Pro His Ser Asp Phe Cys
    50                  55                  60

Leu Gly Cys Ala Ala Ala Pro Pro Ala Pro Phe Arg Leu Leu Trp Pro
65                  70                  75                  80

Ile Ile Ser Phe Phe Leu Ala Leu Thr Ser Thr Ala Leu Leu Phe Leu
                85                  90                  95

Leu Phe Phe Leu Thr Leu Arg Phe Ser Val Val Lys Arg Gly Arg Lys
                100                 105                 110

Lys Leu Leu Tyr Ile Phe Lys Gln Pro Phe Met Arg Pro Val Gln Thr
            115                 120                 125

Thr Gln Glu Glu Asp Gly Cys Ser Cys Arg Phe Pro Glu Glu Glu Glu
        130                 135                 140

Gly Gly Cys Glu Leu
145
```

<210> SEQ ID NO 55
<211> LENGTH: 261
<212> TYPE: PRT
<213> ORGANISM: Artificial Sequence
<220> FEATURE:
<223> OTHER INFORMATION: TNF receptor ligand CD40L

<400> SEQUENCE: 55

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
                100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160
```

```
Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 56
<211> LENGTH: 183
<212> TYPE: PRT
<213> ORGANISM: Artificial Sequence
<220> FEATURE:
<223> OTHER INFORMATION: TNF receptor ligand OX40L

<400> SEQUENCE: 56

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 57
<211> LENGTH: 254
<212> TYPE: PRT
<213> ORGANISM: Artificial Sequence
<220> FEATURE:
<223> OTHER INFORMATION: TNF receptor ligand 41BBL

<400> SEQUENCE: 57

Met Glu Tyr Ala Ser Asp Ala Ser Leu Asp Pro Glu Ala Pro Trp Pro
```

```
            1               5                  10                 15
        Pro Ala Pro Arg Ala Arg Ala Cys Arg Val Leu Pro Trp Ala Leu Val
                        20                 25                 30

Ala Gly Leu Leu Leu Leu Leu Leu Ala Ala Cys Ala Val Phe
                        35                 40                 45

Leu Ala Cys Pro Trp Ala Val Ser Gly Ala Arg Ala Ser Pro Gly Ser
        50                         55                 60

Ala Ala Ser Pro Arg Leu Arg Glu Gly Pro Glu Leu Ser Pro Asp Asp
        65                 70                 75                     80

Pro Ala Gly Leu Leu Asp Leu Arg Gln Gly Met Phe Ala Gln Leu Val
                                85                 90                 95

Ala Gln Asn Val Leu Leu Ile Asp Gly Pro Leu Ser Trp Tyr Ser Asp
                        100                105                110

Pro Gly Leu Ala Gly Val Ser Leu Thr Gly Gly Leu Ser Tyr Lys Glu
                        115                120                125

Asp Thr Lys Glu Leu Val Val Ala Lys Ala Gly Val Tyr Tyr Val Phe
                    130                135                140

Phe Gln Leu Glu Leu Arg Arg Val Val Ala Gly Glu Gly Ser Gly Ser
        145                150                155                160

Val Ser Leu Ala Leu His Leu Gln Pro Leu Arg Ser Ala Ala Gly Ala
                        165                170                175

Ala Ala Leu Ala Leu Thr Val Asp Leu Pro Pro Ala Ser Ser Glu Ala
                        180                185                190

Arg Asn Ser Ala Phe Gly Phe Gln Gly Arg Leu Leu His Leu Ser Ala
                        195                200                205

Gly Gln Arg Leu Gly Val His Leu His Thr Glu Ala Arg Ala Arg His
                        210                215                220

Ala Trp Gln Leu Thr Gln Gly Ala Thr Val Leu Gly Leu Phe Arg Val
        225                230                235                240

Thr Pro Glu Ile Pro Ala Gly Leu Pro Ser Pro Arg Ser Glu
                        245                250
```

<210> SEQ ID NO 58
<211> LENGTH: 4
<212> TYPE: PRT
<213> ORGANISM: Artificial Sequence
<220> FEATURE:
<223> OTHER INFORMATION: basic amino acid furin target sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa may be Arg or Lys

<400> SEQUENCE: 58

Arg Xaa Xaa Arg
1

<210> SEQ ID NO 59
<211> LENGTH: 7
<212> TYPE: PRT
<213> ORGANISM: Artificial Sequence
<220> FEATURE:
<223> OTHER INFORMATION: consensus Tobacco Etch Virus (TEV) cleavage
       site

<400> SEQUENCE: 59

```
Glu Asn Leu Tyr Phe Gln Ser
1               5

<210> SEQ ID NO 60
<211> LENGTH: 4
<212> TYPE: PRT
<213> ORGANISM: Artificial Sequence
<220> FEATURE:
<223> OTHER INFORMATION: ITAM (immunoreceptor tyrosine-based activation
      motif)
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa may be Leu or Ile

<400> SEQUENCE: 60

Tyr Xaa Xaa Xaa
1

<210> SEQ ID NO 61
<211> LENGTH: 7
<212> TYPE: DNA
<213> ORGANISM: Artificial Sequence
<220> FEATURE:
<223> OTHER INFORMATION: frame-slip motif (FSM)

<400> SEQUENCE: 61 uuuuuuu                                                                  7

<210> SEQ ID NO 62
<211> LENGTH: 9
<212> TYPE: DNA
<213> ORGANISM: Artificial Sequence
<220> FEATURE:
<223> OTHER INFORMATION: frame-slip motif (FSM) comprising a stop codon

<400> SEQUENCE: 62 uuuuuuuga                                                                9

<210> SEQ ID NO 63
<211> LENGTH: 9
<212> TYPE: DNA
<213> ORGANISM: Artificial Sequence
<220> FEATURE:
<223> OTHER INFORMATION: FSM comprising a stop codon

<400> SEQUENCE: 63 uuuuuuuag                                                                9

<210> SEQ ID NO 64
<211> LENGTH: 9
<212> TYPE: DNA
<213> ORGANISM: Artificial Sequence
<220> FEATURE:
<223> OTHER INFORMATION: FSM comprising a stop codon

<400> SEQUENCE: 64 uuuuuuuaa                                                                9

<210> SEQ ID NO 65
<211> LENGTH: 7
<212> TYPE: DNA
<213> ORGANISM: Artificial Sequence
<220> FEATURE:
```

```
<223> OTHER INFORMATION: translational readthrough motif (TRM)
      comprising a stop codon

<400> SEQUENCE: 65 ugacuag                                                                    7

<210> SEQ ID NO 66
<211> LENGTH: 7
<212> TYPE: DNA
<213> ORGANISM: Artificial Sequence
<220> FEATURE:
<223> OTHER INFORMATION: TRM comprising a stop codon

<400> SEQUENCE: 66 uagcuag                                                                    7

<210> SEQ ID NO 67
<211> LENGTH: 7
<212> TYPE: DNA
<213> ORGANISM: Artificial Sequence
<220> FEATURE:
<223> OTHER INFORMATION: TRM comprising a stop codon

<400> SEQUENCE: 67 uaacuag                                                                    7

<210> SEQ ID NO 68
<211> LENGTH: 9
<212> TYPE: DNA
<213> ORGANISM: Artificial Sequence
<220> FEATURE:
<223> OTHER INFORMATION: TRM comprising a stop codon

<400> SEQUENCE: 68 ugacaauua                                                                  9

<210> SEQ ID NO 69
<211> LENGTH: 9
<212> TYPE: DNA
<213> ORGANISM: Artificial Sequence
<220> FEATURE:
<223> OTHER INFORMATION: TRM comprising a stop codon

<400> SEQUENCE: 69 uagcaauua                                                                  9

<210> SEQ ID NO 70
<211> LENGTH: 9
<212> TYPE: DNA
<213> ORGANISM: Artificial Sequence
<220> FEATURE:
<223> OTHER INFORMATION: TRM comprising a stop codon

<400> SEQUENCE: 70 uaacaauua                                                                  9

<210> SEQ ID NO 71
<211> LENGTH: 5
<212> TYPE: PRT
<213> ORGANISM: Artificial Sequence
<220> FEATURE:
<223> OTHER INFORMATION: VH CDR, CDR1

<400> SEQUENCE: 71

Ser Tyr Asn Ile His
1               5
```

<210> SEQ ID NO 72
<211> LENGTH: 16
<212> TYPE: PRT
<213> ORGANISM: Artificial Sequence
<220> FEATURE:
<223> OTHER INFORMATION: VH CDR, CDR2

<400> SEQUENCE: 72

Val Ile Trp Ala Gly Gly Ser Thr Asn Tyr Asn Ser Ala Leu Met Ser
1               5                   10                  15

<210> SEQ ID NO 73
<211> LENGTH: 10
<212> TYPE: PRT
<213> ORGANISM: Artificial Sequence
<220> FEATURE:
<223> OTHER INFORMATION: VH CDR, CDR3

<400> SEQUENCE: 73

Arg Ser Asp Asp Tyr Ser Trp Phe Ala Tyr
1               5                   10

<210> SEQ ID NO 74
<211> LENGTH: 12
<212> TYPE: PRT
<213> ORGANISM: Artificial Sequence
<220> FEATURE:
<223> OTHER INFORMATION: VL CDR, CDR1

<400> SEQUENCE: 74

Arg Ala Ser Ser Ser Val Ser Ser Ser Tyr Leu His
1               5                   10

<210> SEQ ID NO 75
<211> LENGTH: 7
<212> TYPE: PRT
<213> ORGANISM: Artificial Sequence
<220> FEATURE:
<223> OTHER INFORMATION: VL CDR, CDR2

<400> SEQUENCE: 75

Ser Thr Ser Asn Leu Ala Ser
1               5

<210> SEQ ID NO 76
<211> LENGTH: 9
<212> TYPE: PRT
<213> ORGANISM: Artificial Sequence
<220> FEATURE:
<223> OTHER INFORMATION: VL CDR, CDR3

<400> SEQUENCE: 76

Gln Gln Tyr Ser Gly Tyr Pro Ile Thr
1               5

<210> SEQ ID NO 77
<211> LENGTH: 118
<212> TYPE: PRT
<213> ORGANISM: Artificial Sequence
<220> FEATURE:
<223> OTHER INFORMATION: humanised KM666 VH sequence

<400> SEQUENCE: 77

Gln Val Gln Leu Gln Glu Ser Gly Pro Gly Leu Val Lys Pro Ser Gln
1               5                   10                  15

```
Thr Leu Ser Ile Thr Cys Thr Val Ser Gly Phe Ser Leu Ala Ser Tyr
            20                  25                  30

Asn Ile His Trp Val Arg Gln Pro Pro Gly Lys Gly Leu Glu Trp Leu
            35                  40                  45

Gly Val Ile Trp Ala Gly Gly Ser Thr Asn Tyr Asn Ser Ala Leu Met
 50                  55                  60

Ser Arg Leu Thr Ile Ser Lys Asp Asn Ser Lys Asn Gln Val Phe Leu
 65                  70                  75                  80

Lys Met Ser Ser Leu Thr Ala Ala Asp Thr Ala Val Tyr Tyr Cys Ala
            85                  90                  95

Lys Arg Ser Asp Asp Tyr Ser Trp Phe Ala Tyr Trp Gly Gln Gly Thr
            100                 105                 110

Leu Val Thr Val Ser Ser
            115

<210> SEQ ID NO 78
<211> LENGTH: 108
<212> TYPE: PRT
<213> ORGANISM: Artificial Sequence
<220> FEATURE:
<223> OTHER INFORMATION: humanised KM666 VL sequence

<400> SEQUENCE: 78

Glu Asn Gln Met Thr Gln Ser Pro Ser Ser Leu Ser Ala Ser Val Gly
 1               5                   10                  15

Asp Arg Val Thr Met Thr Cys Arg Ala Ser Ser Ser Val Ser Ser Ser
            20                  25                  30

Tyr Leu His Trp Tyr Gln Gln Lys Ser Gly Lys Ala Pro Lys Val Trp
            35                  40                  45

Ile Tyr Ser Thr Ser Asn Leu Ala Ser Gly Val Pro Ser Arg Phe Ser
 50                  55                  60

Gly Ser Gly Ser Gly Thr Asp Tyr Thr Leu Thr Ile Ser Ser Leu Gln
 65                  70                  75                  80

Pro Glu Asp Phe Ala Thr Tyr Tyr Cys Gln Gln Tyr Ser Gly Tyr Pro
            85                  90                  95

Ile Thr Phe Gly Gln Gly Thr Lys Val Glu Ile Lys
            100                 105

<210> SEQ ID NO 79
<211> LENGTH: 136
<212> TYPE: PRT
<213> ORGANISM: Artificial Sequence
<220> FEATURE:
<223> OTHER INFORMATION: sort/suicide gene RQR8

<400> SEQUENCE: 79

Cys Pro Tyr Ser Asn Pro Ser Leu Cys Ser Gly Gly Gly Gly Ser Glu
 1               5                   10                  15

Leu Pro Thr Gln Gly Thr Phe Ser Asn Val Ser Thr Asn Val Ser Pro
            20                  25                  30

Ala Lys Pro Thr Thr Thr Ala Cys Pro Tyr Ser Asn Pro Ser Leu Cys
            35                  40                  45

Ser Gly Gly Gly Ser Pro Ala Pro Arg Pro Thr Pro Ala Pro
 50                  55                  60

Thr Ile Ala Ser Gln Pro Leu Ser Leu Arg Pro Glu Ala Cys Arg Pro
 65                  70                  75                  80

Ala Ala Gly Gly Ala Val His Thr Arg Gly Leu Asp Phe Ala Cys Asp
            85                  90                  95
```

Ile Tyr Ile Trp Ala Pro Leu Ala Gly Thr Cys Gly Val Leu Leu Leu
                100                 105                 110

Ser Leu Val Ile Thr Leu Tyr Cys Asn His Arg Asn Arg Arg Val
        115                 120                 125

Cys Lys Cys Pro Arg Pro Val Val
    130                 135

<210> SEQ ID NO 80
<211> LENGTH: 517
<212> TYPE: PRT
<213> ORGANISM: Artificial Sequence
<220> FEATURE:
<223> OTHER INFORMATION: suicide gene Rapcasp9

<400> SEQUENCE: 80

Met Ala Ser Arg Ile Leu Trp His Glu Met Trp His Glu Gly Leu Glu
1               5                   10                  15

Glu Ala Ser Arg Leu Tyr Phe Gly Glu Arg Asn Val Lys Gly Met Phe
            20                  25                  30

Glu Val Leu Glu Pro Leu His Ala Met Met Glu Arg Gly Pro Gln Thr
        35                  40                  45

Leu Lys Glu Thr Ser Phe Asn Gln Ala Tyr Gly Arg Asp Leu Met Glu
    50                  55                  60

Ala Gln Glu Trp Cys Arg Lys Tyr Met Lys Ser Gly Asn Val Lys Asp
65                  70                  75                  80

Leu Leu Gln Ala Trp Asp Leu Tyr Tyr His Val Phe Arg Arg Ile Ser
                85                  90                  95

Lys Leu Glu Tyr Ser Gly Gly Gly Ser Leu Glu Gly Val Gln Val Glu
            100                 105                 110

Thr Ile Ser Pro Gly Asp Gly Arg Thr Phe Pro Lys Arg Gly Gln Thr
        115                 120                 125

Cys Val Val His Tyr Thr Gly Met Leu Glu Asp Gly Lys Lys Phe Asp
    130                 135                 140

Ser Ser Arg Asp Arg Asn Lys Pro Phe Lys Phe Met Leu Gly Lys Gln
145                 150                 155                 160

Glu Val Ile Arg Gly Trp Glu Glu Gly Val Ala Gln Met Ser Val Gly
                165                 170                 175

Gln Arg Ala Lys Leu Thr Ile Ser Pro Asp Tyr Ala Tyr Gly Ala Thr
            180                 185                 190

Gly His Pro Gly Ile Ile Pro Pro His Ala Thr Leu Val Phe Asp Val
        195                 200                 205

Glu Leu Leu Lys Leu Glu Ser Gly Gly Gly Ser Gly Gly Gly Gly
    210                 215                 220

Ser Gly Gly Gly Gly Ser Gly Val Asp Gly Phe Gly Asp Val Gly Ala
225                 230                 235                 240

Leu Glu Ser Leu Arg Gly Asn Ala Asp Leu Ala Tyr Ile Leu Ser Met
                245                 250                 255

Glu Pro Cys Gly His Cys Leu Ile Ile Asn Asn Val Asn Phe Cys Arg
            260                 265                 270

Glu Ser Gly Leu Arg Thr Arg Thr Gly Ser Asn Ile Asp Cys Glu Lys
        275                 280                 285

Leu Arg Arg Arg Phe Ser Ser Leu His Phe Met Val Glu Val Lys Gly
    290                 295                 300

Asp Leu Thr Ala Lys Lys Met Val Leu Ala Leu Leu Glu Leu Ala Gln
305                 310                 315                 320

```
Gln Asp His Gly Ala Leu Asp Cys Cys Val Val Ile Leu Ser His
                325                 330                 335

Gly Cys Gln Ala Ser His Leu Gln Phe Pro Gly Ala Val Tyr Gly Thr
            340                 345                 350

Asp Gly Cys Pro Val Ser Val Glu Lys Ile Val Asn Ile Phe Asn Gly
            355                 360                 365

Thr Ser Cys Pro Ser Leu Gly Gly Lys Pro Lys Leu Phe Phe Ile Gln
370                 375                 380

Ala Cys Gly Gly Glu Gln Lys Asp His Gly Phe Glu Val Ala Ser Thr
385                 390                 395                 400

Ser Pro Glu Asp Glu Ser Pro Gly Ser Asn Pro Glu Pro Asp Ala Thr
                405                 410                 415

Pro Phe Gln Glu Gly Leu Arg Thr Phe Asp Gln Leu Asp Ala Ile Ser
                420                 425                 430

Ser Leu Pro Thr Pro Ser Asp Ile Phe Val Ser Tyr Ser Thr Phe Pro
            435                 440                 445

Gly Phe Val Ser Trp Arg Asp Pro Lys Ser Gly Ser Trp Tyr Val Glu
            450                 455                 460

Thr Leu Asp Asp Ile Phe Glu Gln Trp Ala His Ser Glu Asp Leu Gln
465                 470                 475                 480

Ser Leu Leu Arg Val Ala Asn Ala Val Ser Val Lys Gly Ile Tyr
                485                 490                 495

Lys Gln Met Pro Gly Cys Phe Asn Phe Leu Arg Lys Lys Leu Phe Phe
                500                 505                 510

Lys Thr Ser Ala Ser
            515

<210> SEQ ID NO 81
<211> LENGTH: 520
<212> TYPE: PRT
<213> ORGANISM: Artificial Sequence
<220> FEATURE:
<223> OTHER INFORMATION: a flexi-IL-12 sequence

<400> SEQUENCE: 81

Met Trp Ile Trp Glu Leu Lys Lys Asp Val Tyr Val Val Glu Leu Asp
1               5                   10                  15

Trp Tyr Pro Asp Ala Pro Gly Glu Met Val Val Leu Thr Cys Asp Thr
            20                  25                  30

Pro Glu Glu Asp Gly Ile Thr Trp Thr Leu Asp Gln Ser Ser Glu Val
        35                  40                  45

Leu Gly Ser Gly Lys Thr Leu Thr Ile Gln Val Lys Glu Phe Gly Asp
    50                  55                  60

Ala Gly Gln Tyr Thr Cys His Lys Gly Gly Glu Val Leu Ser His Ser
65                  70                  75                  80

Leu Leu Leu Leu His Lys Lys Glu Asp Gly Ile Trp Ser Thr Asp Ile
                85                  90                  95

Leu Lys Asp Gln Lys Glu Pro Lys Asn Lys Thr Phe Leu Arg Cys Glu
            100                 105                 110

Ala Lys Asn Tyr Ser Gly Arg Phe Thr Cys Trp Trp Leu Thr Thr Ile
        115                 120                 125

Ser Thr Asp Leu Thr Phe Ser Val Lys Ser Ser Arg Gly Ser Ser Asp
    130                 135                 140

Pro Gln Gly Val Thr Cys Gly Ala Ala Thr Leu Ser Ala Glu Arg Val
145                 150                 155                 160
```

```
Arg Gly Asp Asn Lys Glu Tyr Glu Tyr Ser Val Glu Cys Gln Glu Asp
                165                 170                 175

Ser Ala Cys Pro Ala Ala Glu Glu Ser Leu Pro Ile Glu Val Met Val
            180                 185                 190

Asp Ala Val His Lys Leu Lys Tyr Glu Asn Tyr Thr Ser Ser Phe Phe
            195                 200                 205

Ile Arg Asp Ile Ile Lys Pro Asp Pro Lys Asn Leu Gln Leu Lys
210                 215                 220

Pro Leu Lys Asn Ser Arg Gln Val Glu Val Ser Trp Glu Tyr Pro Asp
225                 230                 235                 240

Thr Trp Ser Thr Pro His Ser Tyr Phe Ser Leu Thr Phe Cys Val Gln
            245                 250                 255

Val Gln Gly Lys Ser Lys Arg Glu Lys Lys Asp Arg Val Phe Thr Asp
            260                 265                 270

Lys Thr Ser Ala Thr Val Ile Cys Arg Lys Asn Ala Ser Ile Ser Val
            275                 280                 285

Arg Ala Gln Asp Arg Tyr Tyr Ser Ser Ser Trp Ser Glu Trp Ala Ser
            290                 295                 300

Val Pro Cys Ser Gly Gly Gly Gly Ser Gly Gly Gly Gly Ser Gly Gly
305                 310                 315                 320

Gly Gly Ser Arg Asn Leu Pro Leu Ala Thr Pro Asp Pro Gly Met Phe
                325                 330                 335

Pro Cys Leu His His Ser Gln Asn Leu Leu Arg Ala Val Ser Asn Met
                340                 345                 350

Leu Gln Lys Ala Arg Gln Thr Leu Glu Phe Tyr Pro Cys Thr Ser Glu
                355                 360                 365

Glu Ile Asp His Glu Asp Ile Thr Lys Asp Lys Thr Ser Thr Val Glu
                370                 375                 380

Ala Cys Leu Pro Leu Glu Leu Thr Lys Asn Glu Ser Cys Leu Asn Ser
385                 390                 395                 400

Arg Glu Thr Ser Phe Ile Thr Asn Gly Ser Cys Leu Ala Ser Arg Lys
                405                 410                 415

Thr Ser Phe Met Met Ala Leu Cys Leu Ser Ser Ile Tyr Glu Asp Ser
                420                 425                 430

Lys Met Tyr Gln Val Glu Phe Lys Thr Met Asn Ala Lys Leu Leu Met
                435                 440                 445

Asp Pro Lys Arg Gln Ile Phe Leu Asp Gln Asn Met Leu Ala Val Ile
            450                 455                 460

Asp Glu Leu Met Gln Ala Leu Asn Phe Asn Ser Glu Thr Val Pro Gln
465                 470                 475                 480

Lys Ser Ser Leu Glu Glu Pro Asp Phe Tyr Lys Thr Lys Ile Lys Leu
                485                 490                 495

Cys Ile Leu Leu His Ala Phe Arg Ile Arg Ala Val Thr Ile Asp Arg
                500                 505                 510

Val Met Ser Tyr Leu Asn Ala Ser
            515                 520
```

COMPOSITIONS AND METHODS COMPRISING ENGINEERED CHIMERIC ANTIGEN RECEPTOR AND MODULATOR OF CAR

CROSS-REFERENCE TO RELATED APPLICATIONS

This is a continuation of U.S. application Ser. No. 17/436,673 filed Jul. 28, 2021, which is the U.S. National Phase of International Application No. PCT/GB2020/050535 filed Mar. 6, 2020, which claims priority to Great Britain Application No. 1903237.4 filed Mar. 8, 2019, Great Britain Application No. 1914216.5 filed Oct. 2, 2019 and Great Britain Application No. 1916077.9 filed Nov. 5, 2019.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "56191A_SeqListing.xml", which was created on May 16, 2022 and is 85,805 bytes in size. The subject matter of the Sequence Listing is incorporated herein in its entirety by reference.

FIELD OF THE INVENTION

The present invention relates viral vector compositions, their use to transduce cells and cell compositions made by such methods.

BACKGROUND TO THE INVENTION

Tumour heterogeneity describes the observation that different tumour cells can show distinct morphological and phenotypic profiles, including cellular morphology, gene expression, metabolism, motility, proliferation, and metastatic potential.

Heterogeneity occurs between patients, between tumours (inter-tumour heterogeneity) and within tumours (intra-tumour heterogeneity). Multiple types of heterogeneity have been observed between tumour cells, stemming from both genetic and non-genetic variability.

Heterogeneity between tumour cells can be further increased due to heterogeneity in the tumour microenvironment. Regional differences in the tumour (e.g. availability of oxygen) impose different selective pressures on tumour cells, leading to a wider spectrum of dominant subclones in different spatial regions of the tumour. The influence of microenvironment on clonal dominance is also a likely reason for the heterogeneity between primary and metastatic tumours seen in many patients, as well as the inter-tumour heterogeneity observed between patients with the same tumour type.

The heterogeneity of cancer cells introduces significant challenges in designing effective treatment strategies.

For example, heterogeneic tumours may exhibit different sensitivities to cytotoxic drugs among different clonal populations. This is attributed to clonal interactions that may inhibit or alter therapeutic efficacy.

Drug administration in heterogeneic tumours will seldom kill all tumour cells. The initial heterogeneic tumour population may bottleneck, such that few drug resistant cells (if any) will survive. This allows resistant tumour populations to replicate and grow a new tumour through the branching evolution mechanism (see above). The resulting repopulated tumour is heterogeneic and resistant to the initial drug therapy used. The repopulated tumour may also return in a more aggressive manner.

Chimeric Antigen Receptors (CARs)

Chimeric antigen receptors are proteins which graft the specificity of, for example, a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals (see FIG. 1A).

The most common form of these molecules are fusions of single-chain variable fragments (scFv) derived from monoclonal antibodies which recognize a target antigen, fused via a spacer and a trans-membrane domain to a signalling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

Successful CAR treatment depends on expression of the target antigen by tumour cells. In heterogenic tumours, in particular solid cancers, antigen expression is heterogeneous, and it may not be possible to find a single target antigen expressed by all cancer cells.

Moreover, emerging data from CAR T-cell trials in B-cell malignancies demonstrate that a common mechanism of resistance to this class of therapeutics is the emergence of tumours with loss or downregulation of the target antigen. Antigen loss or antigen-low escape is likely to emerge as an even greater barrier to success in solid tumours, which manifest greater heterogeneity in target antigen expression. Potential approaches to overcome this challenge include engineering CAR T cells to achieve multi-specificity and to respond to lower levels of target antigen and more efficient induction of natural antitumor immune responses as a result of CAR-induced inflammation.

Clinical studies of CAR T-cells have established that CAR T-cell engraftment, expansion and persistence are a prerequisite for clinical activity, particularly sustained responses. A key reason for poor persistence of CAR-T cells in vivo, particularly CAR-T cells for the treatment of solid cancers, is that the cells struggle to overcome the hostile microenvironment of the tumour. In particular, CAR T-cells may fail to engraft and expand within a solid cancer tumour bed.

CAR T-cell persistence and activity can be enhanced by administration of cytokines, or by engineering the CAR T-cell to secrete or express cytokine, toxins or other factors. However, these approaches have limitations: systemic administration of cytokines can be toxic; constitutive production of cytokines may lead to uncontrolled proliferation and transformation.

There is thus a need for alternative CAR treatment approaches which address the problems commonly encountered with CAR-T cell therapy, particularly bearing in mind the heterogeneity between patients, and between tumour cells and tumour cell sites within the same patient.

DESCRIPTION OF THE FIGURES

FIG. 12B Ventral images of mice obtained on days −1, 2, 7, 10 and 14 following administration of CAR-T cells expressing GD2 CAR alone (GD2 CAR); untransduced T cells (NT) or buffer alone (PBS) FIG. 12C Graph showing fluorescent signal over time for mice receiving cells transduced with the dual vector composition described in Example 3 and Illustrated in FIG. 7 (GD2 CAR+IL7 CCR/GD2 CAR+dSHP2+dTGFbRII); untransduced T cells (NT) or buffer alone (PBS). FIG. 12D Ventral images of mice obtained on days −1, 2, 7, 10 and 14 following administration of cells transduced with the dual vector composition described in Example 3 and Illustrated in FIG. 7 (GD2 CAR+IL7 CCR/GD2 CAR+dSHP2+dTGFbRII); untransduced T cells (NT) or buffer alone (PBS).

Vector A expresses truncated SHP2 (dSHP2); the safety switch RQR8; an anti-PSMA CAR based on a novel humanized binder 7A12 (7A12-28z); and dominant negative TGFβRII (dnTBRII).

Vector B expresses a constitutively active IL-7 receptor (CCR_IL7).

Vector C expresses the RapaCasp9 suicide gene (RapaCasp9); CD19 (dCD19) and an IL-12 module (flexiIL-12). "2A" is an co-expression sequence based on the FMDV 2A peptide.

Figure 13A:
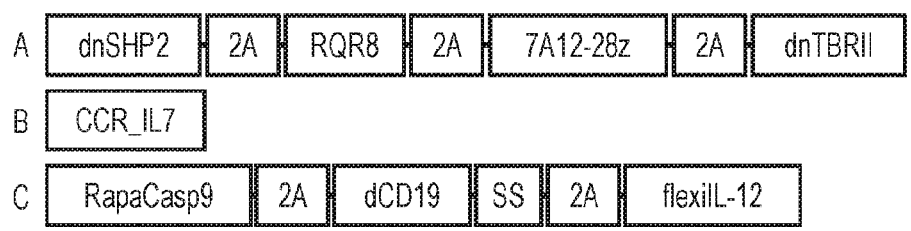
FIGS. 13A-13B—FIG. 13A Schematic diagram illustrating the molecules expressed by the vectors used in the triple vector composition "AUTO7" described in Example 6.
Figure 13B:
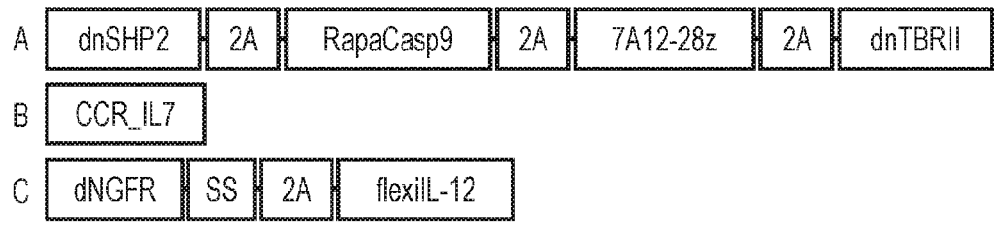

FIG. 13B An alternative arrangement for the triple vector composition. Components are as indicated for FIG. 13A above. dNGFR is truncated Nerve Growth Factor Receptor which is used as a marker protein.

Figure 14:
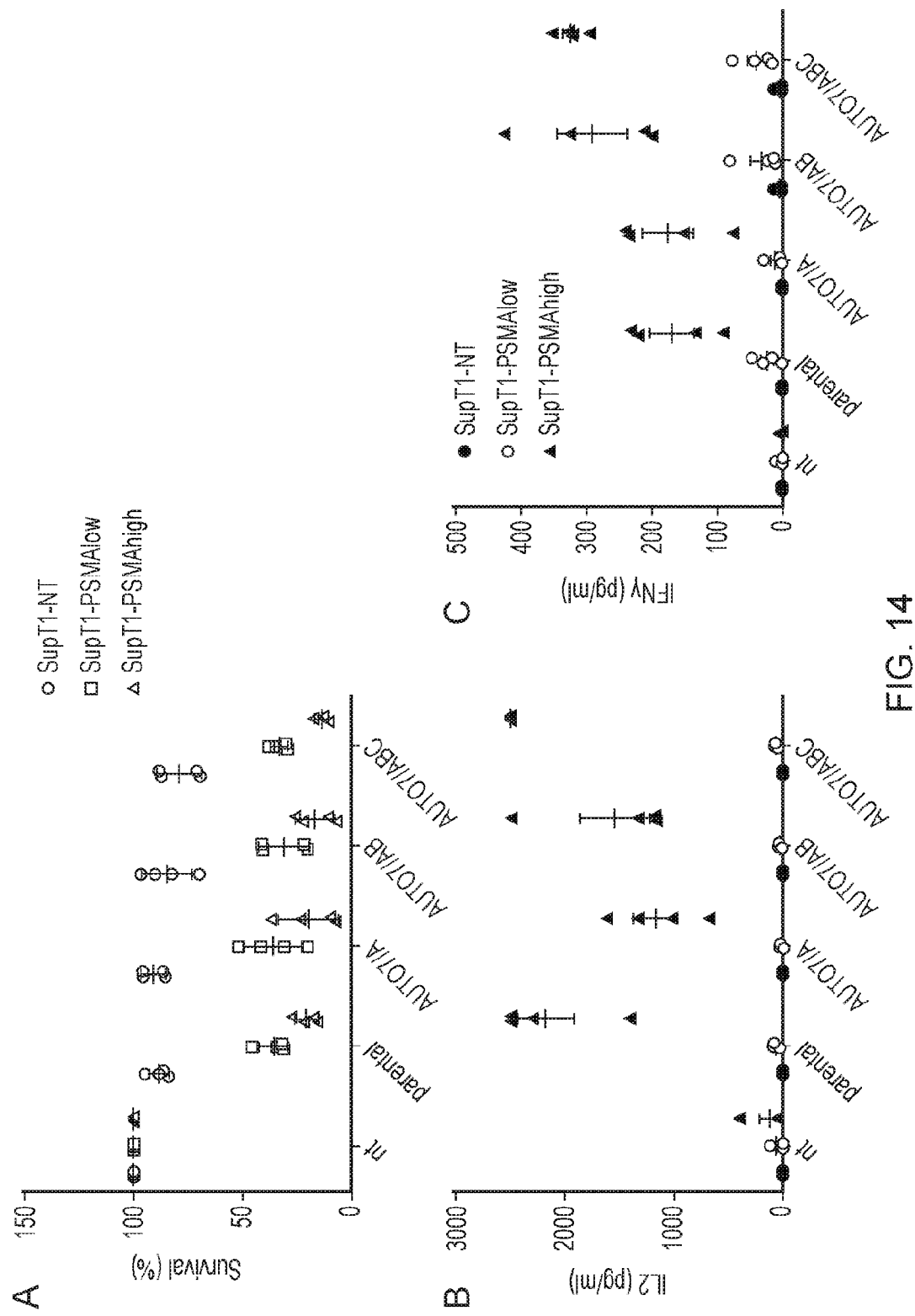

FIG. 14—Results of a FACS-based killing (FBK) assay investigating the capacity of single, double and triple transduced T cells to kill PSMA-expressing target cells. A: FBK after 24 h of incubation using cytofluorimetry analysis to show survival of target cells. B: Secretion of IL-2 and IFNγ by CAR T-cells measured by collecting supernatant at 24 hr from the co-cultures described and detecting by ELISA.

AUTO7 was investigated as product of a single transduction using the vector A. ("AUTO7/A"), or double transduction using vectors A and B ("AUTO7/AB"), or triple transduction using vectors A, B and C ("AUTO7/ABC"). AUTO7 was tested against a second generation CAR developed using the same anti PSMA binder 7A12 ("Parental")

SupT1 target cells were engineered to express human PSMA antigen at different levels (SupT1-PSMAhigh, SupT1-PSMAlow) were used as target cells. Non-engineered SupT1 cells (SupT1-NT) were used as a negative control. CAR T-cells were co-cultured with target cells at 1:2 effector to target ratios.

Figure 15A:
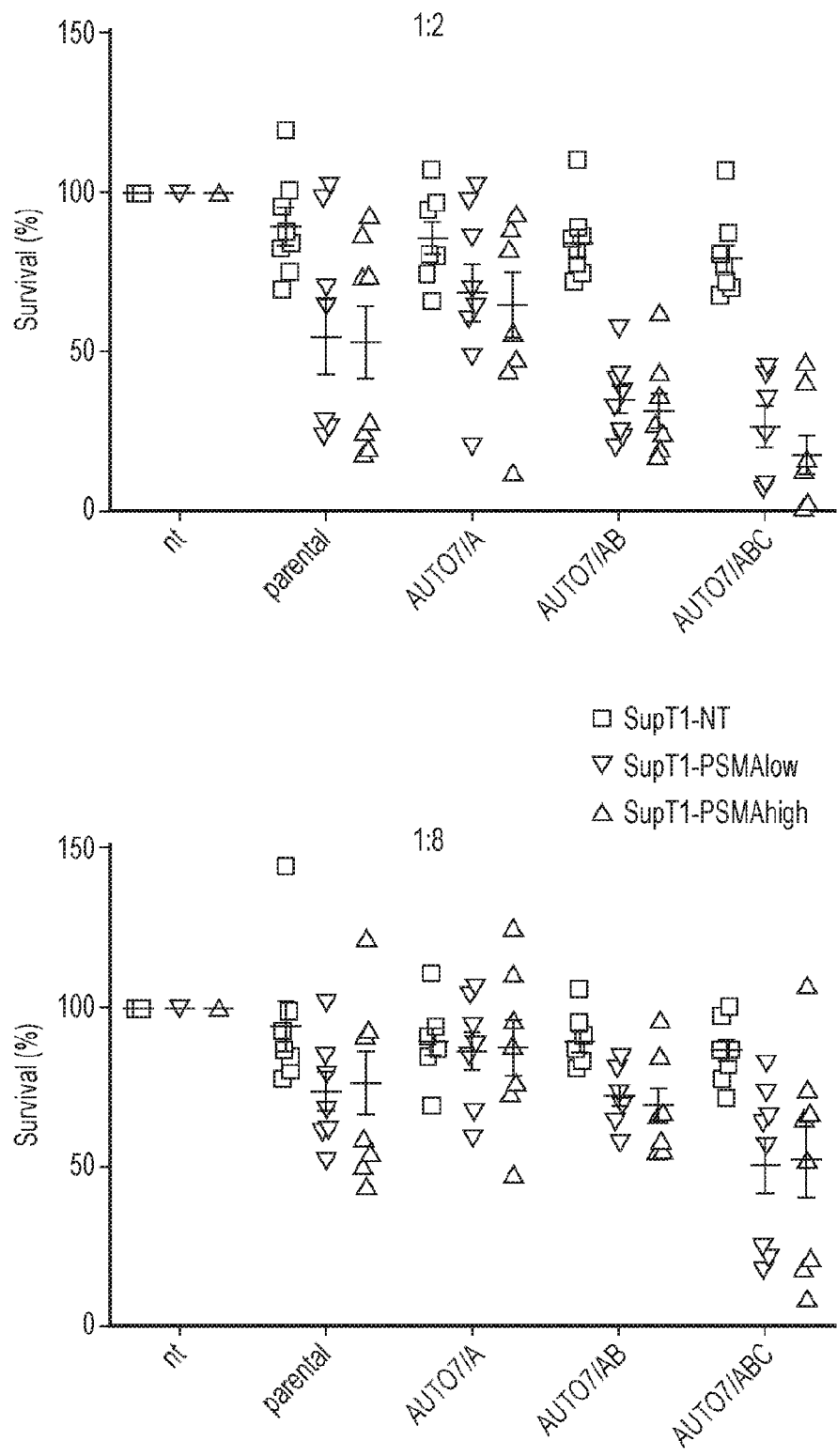
Figure 15B:
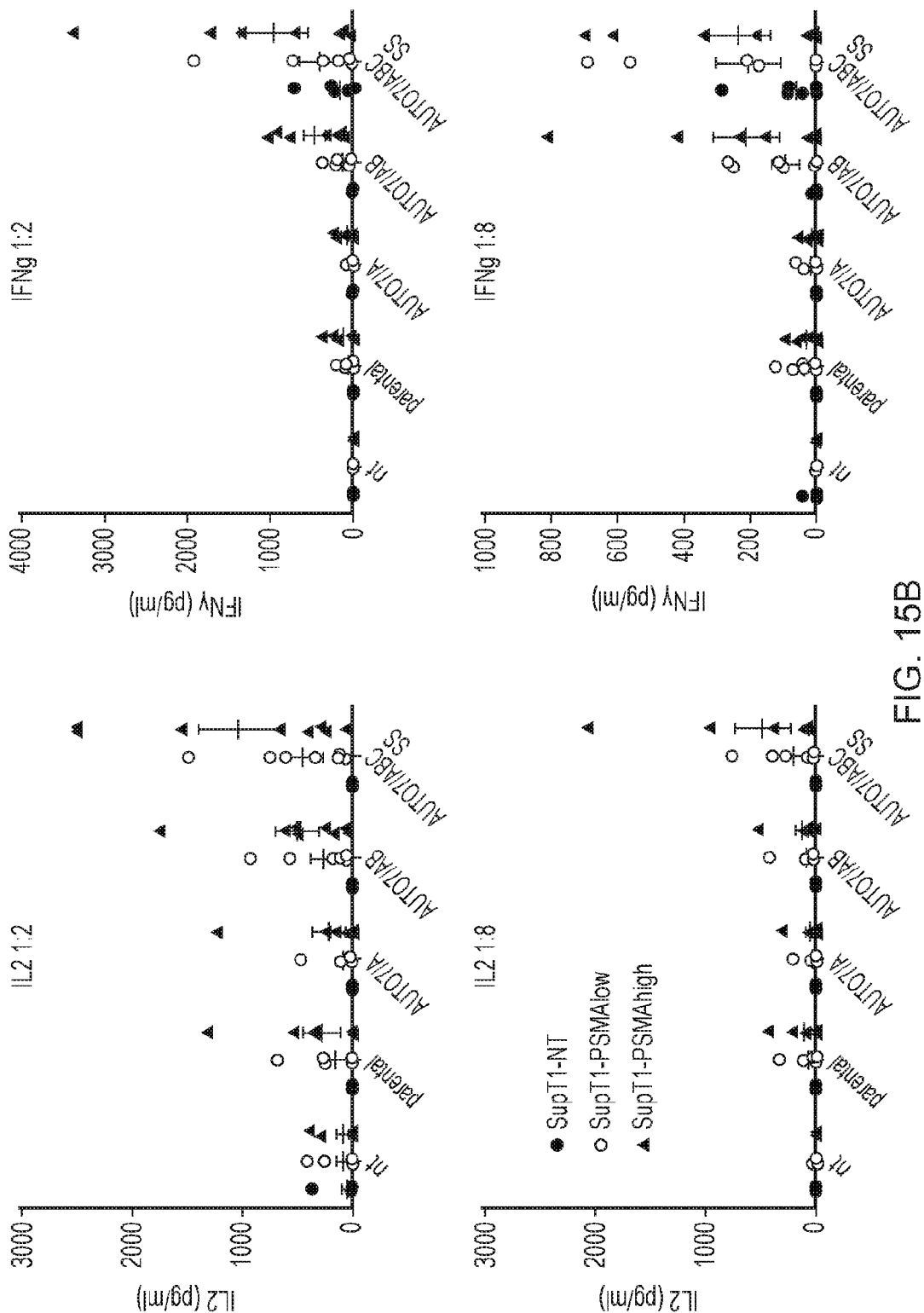

FIGS. 15A-15B—Results of a FACS-based killing (FBK) assay investigating the capacity of single, double and triple transduced T cells to kill PSMA-expressing target cells following culture in cytokine-free complete cell culture media. After 7 days culture in "starvation conditions" CAR T-cells were co-cultured with SupT1-PSMAhigh and SupT1-PSMAlow targets cells (or SupT1-NT cells as negative control). at 1:2 and 1:8 effector to target ratios. FIG. 15A: FBK after 24 h of incubation using cytofluorimetry analysis to show survival of target cells. FIG. 15B: Secretion of IL-2 and IFNγ by CAR T-cells measured by collecting supernatant at 24 hr from the co-cultures described and detecting by ELISA.

Figure 16:
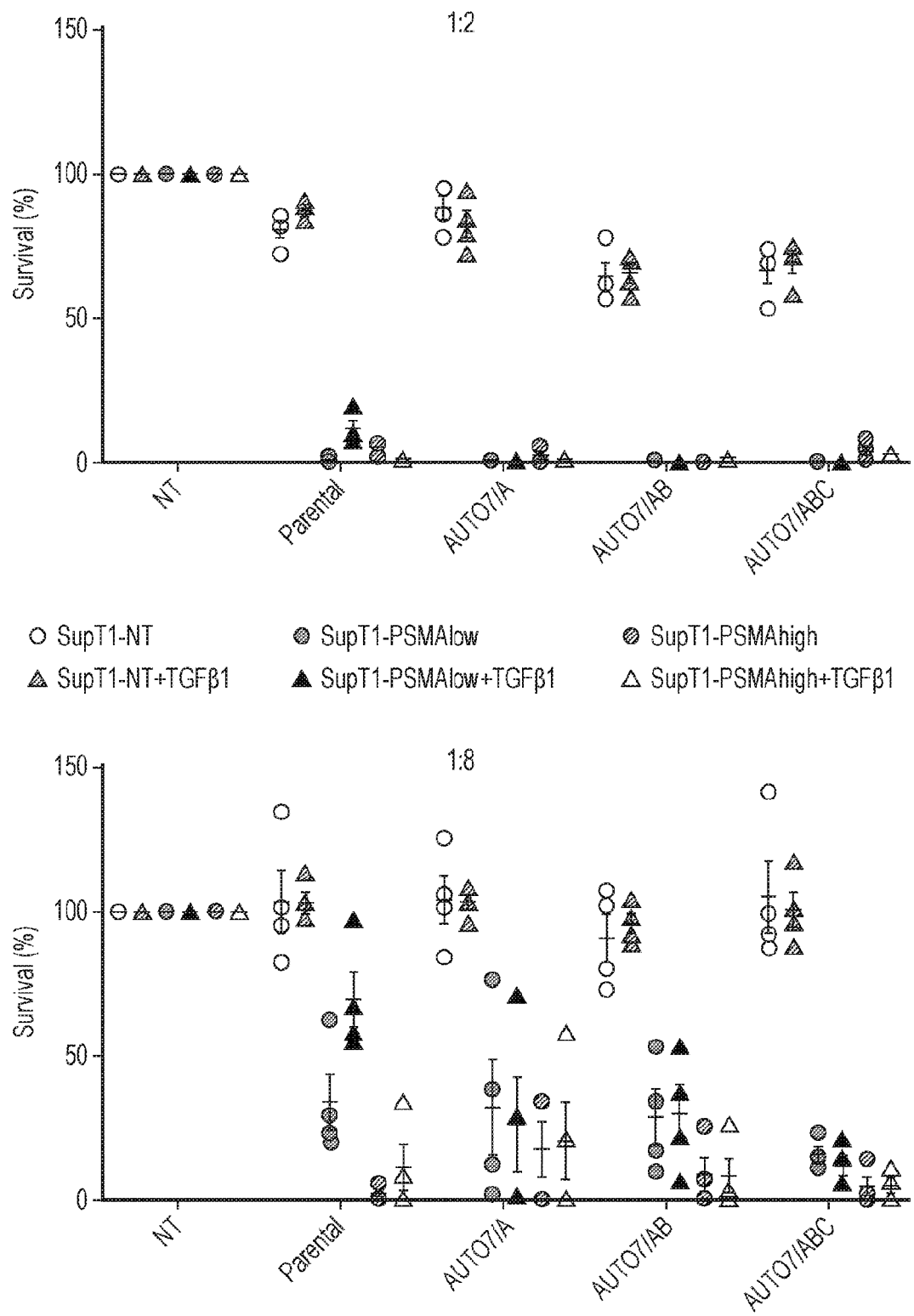

FIG. 16—Results of a FACS-based killing (FBK) assay investigating the capacity of single, double and triple transduced T cells to kill PSMA-expressing target cells in the presence or absence of TGFβ. CAR T-cells were co-cultured with SupT1-PSMAhigh and SupT1-PSMAlow targets for 7 days at ratio 1:2 and 1:8 (E:T) either in the presence or absence of 10 ng/ml TGFβ1 (SupT1-NT were used as control). Target cell killing was quantified by FACS and normalised to targets alone.

Figure 17:
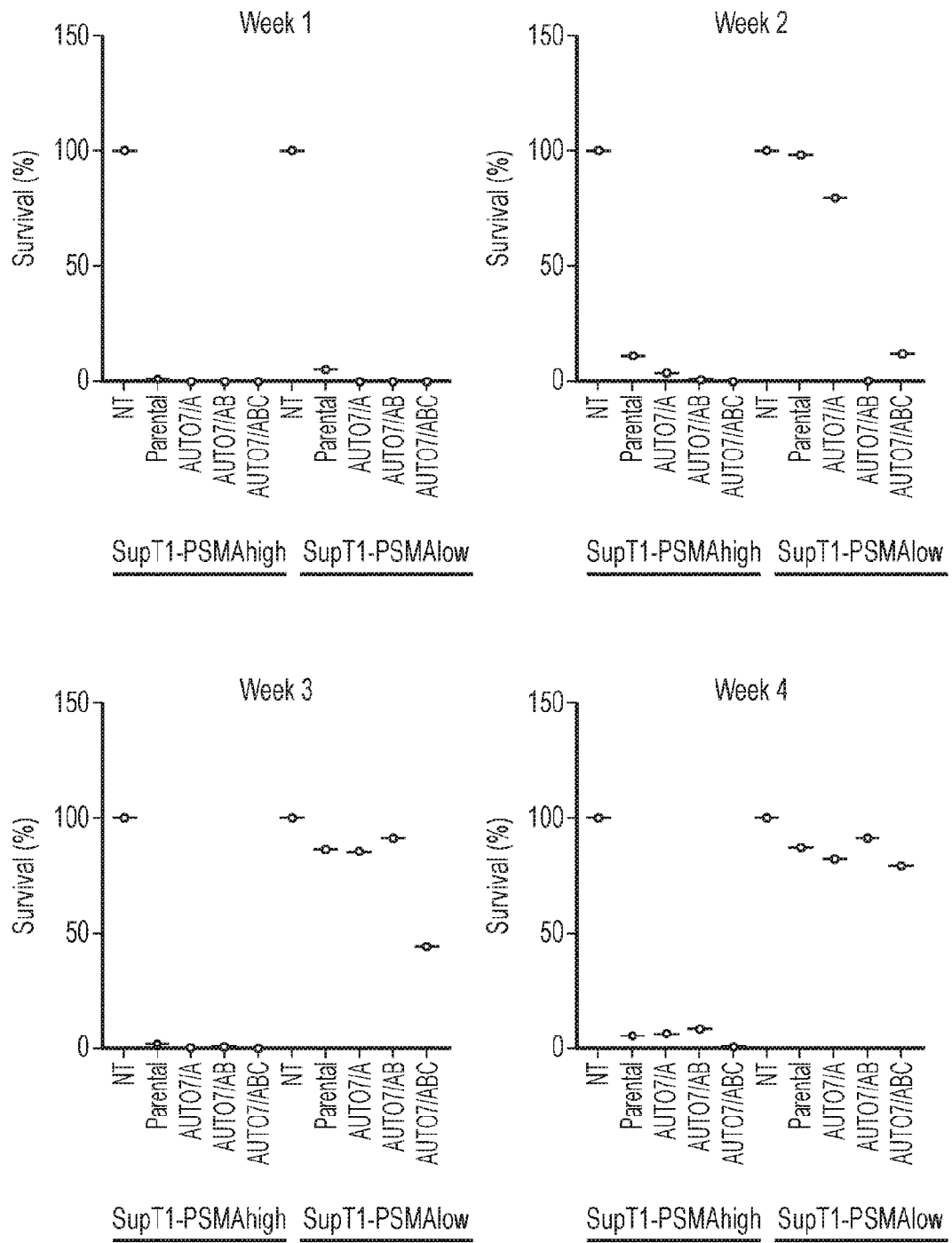

FIG. 17—Results of a FACS-based killing (FBK) assay investigating the capacity of single, double and triple transduced T cells to kill PSMA-expressing target cells following repeated restimulation with target cells. Transduced T-cells were co-cultured with SupT1-PSMAhigh or SupT1-PSMAlow target cells at 1:1 ratio (E:T). Every 7 days CAR T-cells were re-stimulated with $5 \times 10^4$ SupT1 cells. Target cell killing was quantified by FACS before each new re-stimulation.

Figure 18A:
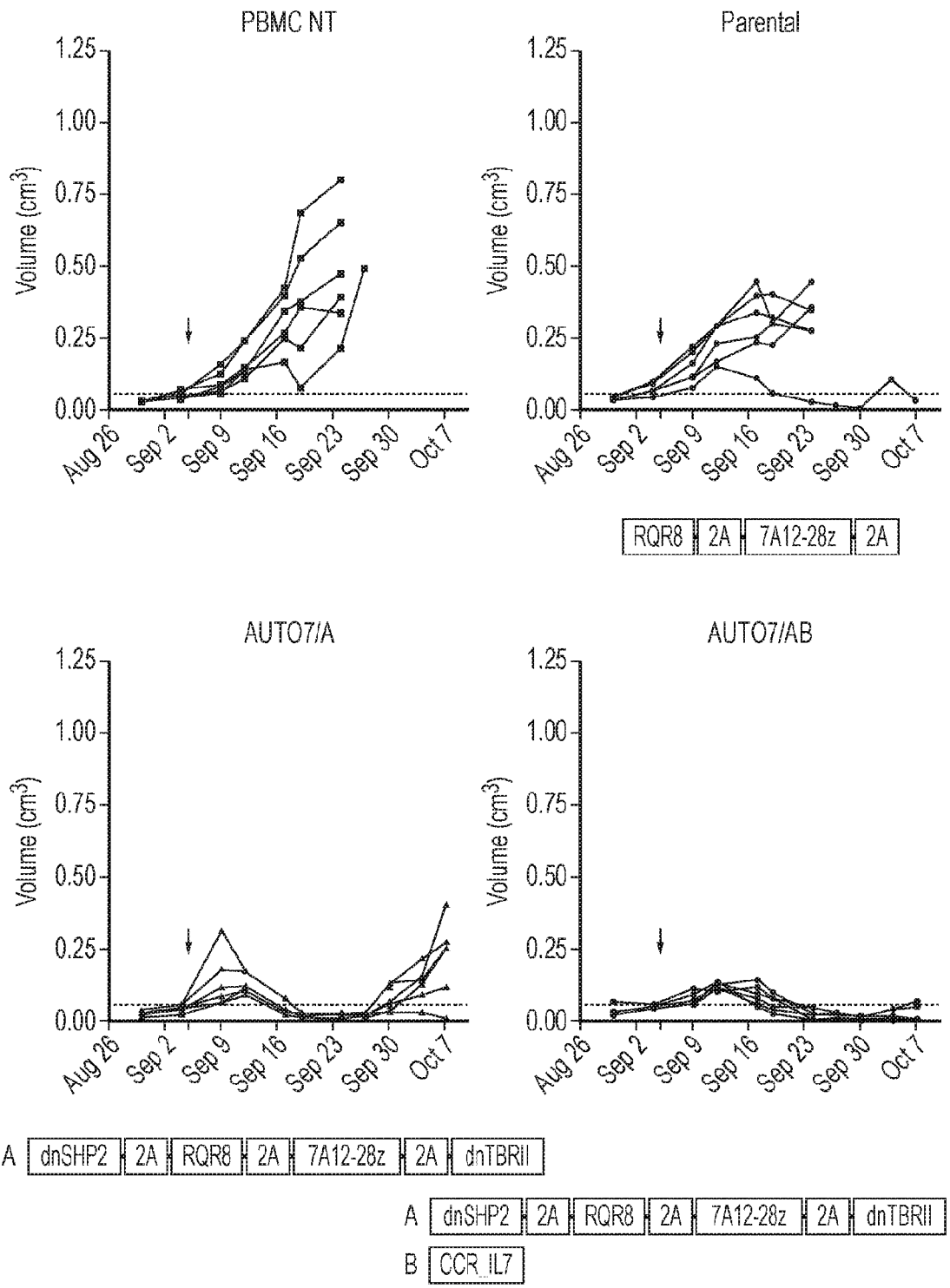
Figure 18A:
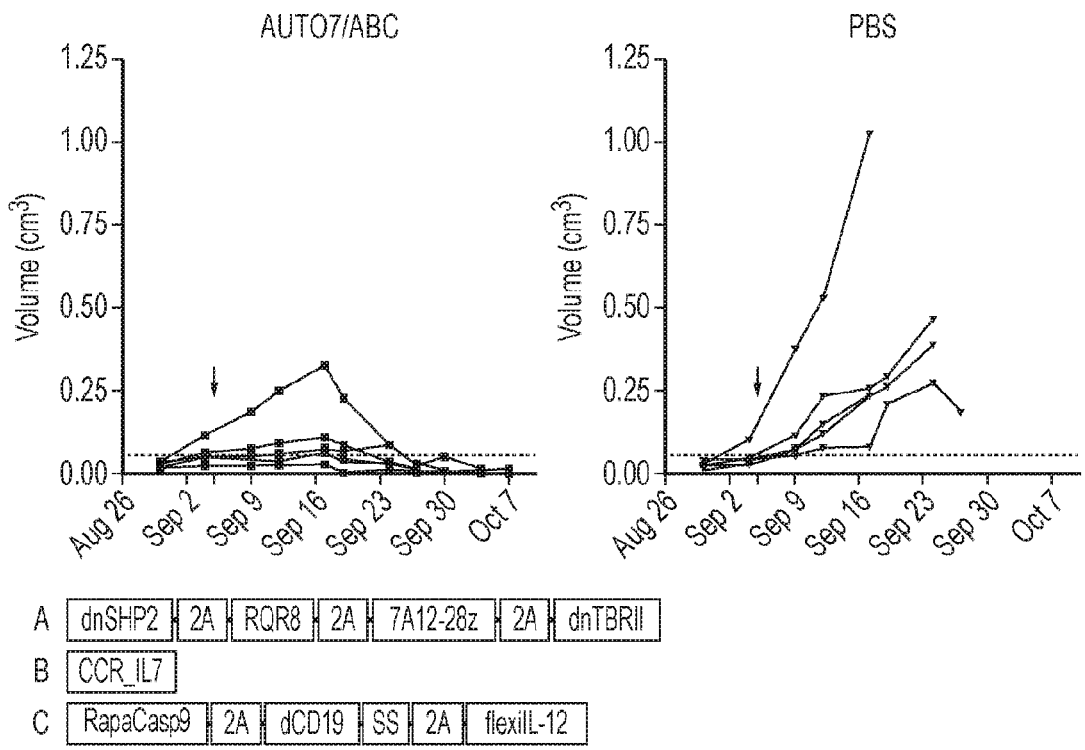
Figure 18B:
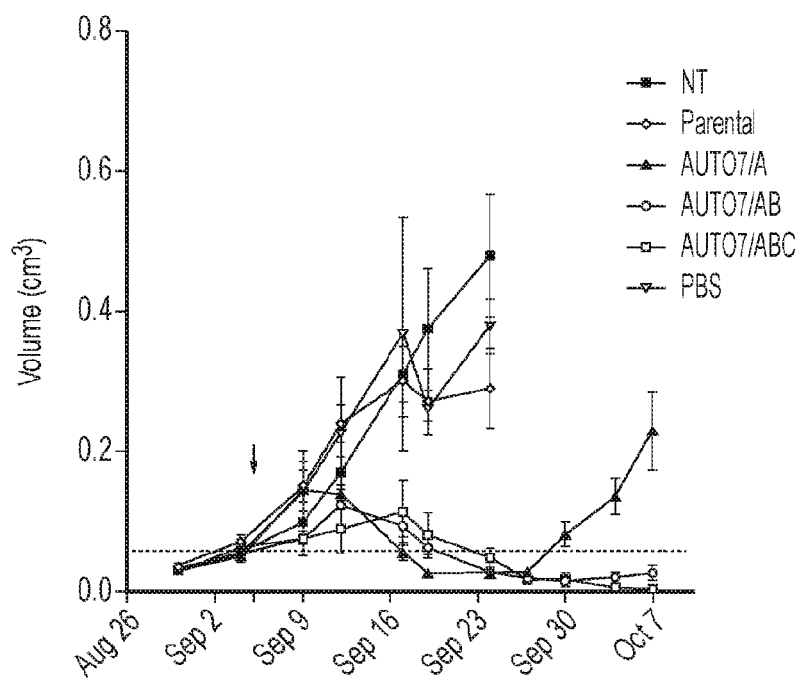

FIGS. 18A-18B—In vivo assay investigating the anti-tumour activity of T cells transduced with the triple vector composition by intravenous administration in a prostate cancer xenograft model in NSG mice. $5 \times 10^6$ PSMA positive PC3 human cell lines were injected in the flank of female NSG mice. Xenografts were left to establish for 3 weeks until stable engraftment was detectable by palpation and caliper measurement. CAR T-cells were administered i.v. at a dose of $1 \times 10^6$ CAR T-cells/mouse. Caliper measurement was taken 2/3 times a week. FIG. 18A: Data for mice receiving cells made by single transduction using the vector A. ("AUTO7/A"), double transduction using vectors A and B ("AUTO7/AB"), triple transduction using vectors A, B and C ("AUTO7/ABC"); or a second generation CAR developed using the same anti PSMA binder 7A12 ("Parental"); FIG. 18B: Summary of data shown in FIG. 18A.

SUMMARY OF ASPECTS OF THE INVENTION

The present inventors have developed a combinatorial approach to address the issue of tumour cell and microenvironment heterogeneity to CAR therapies.

Figure 5:
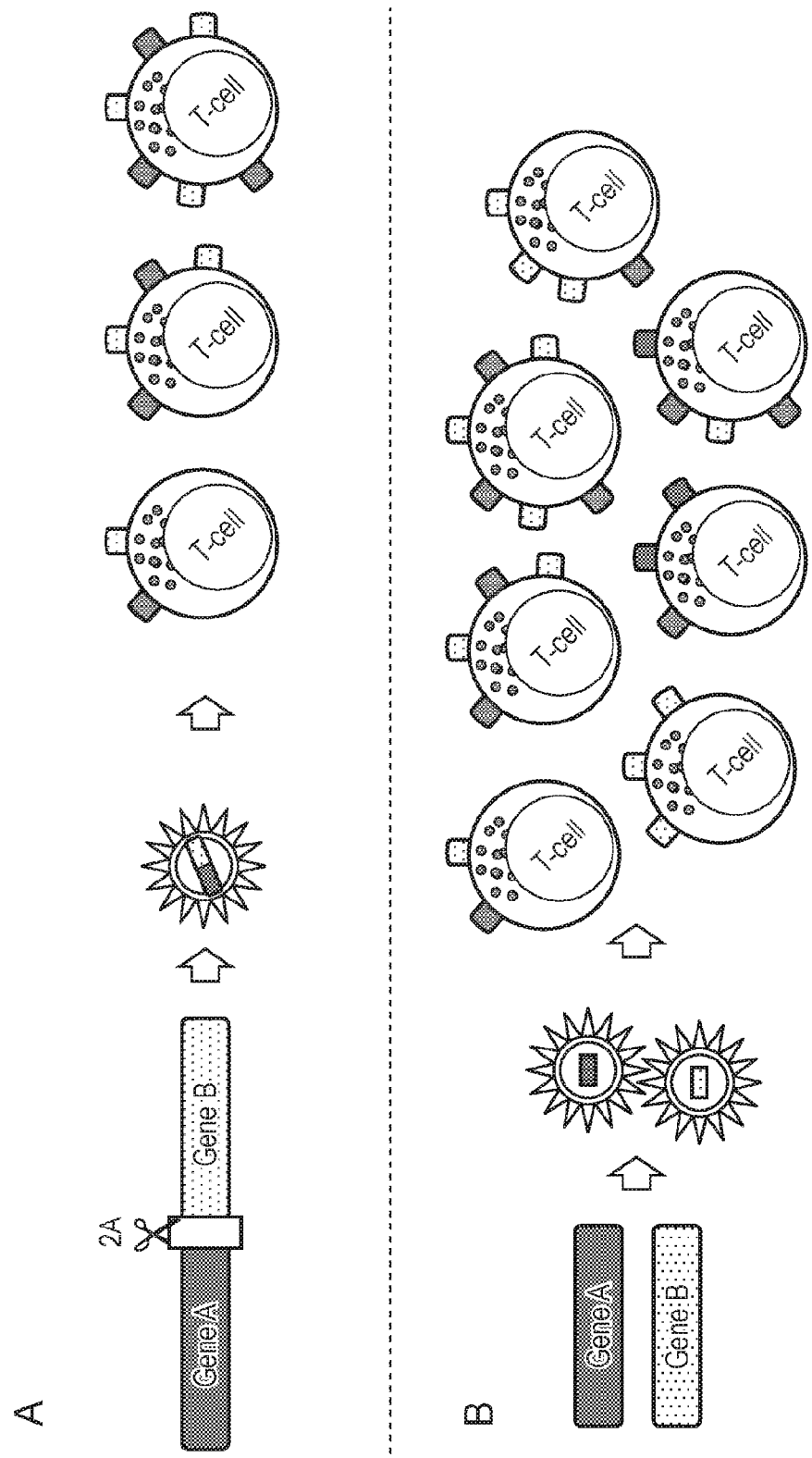

When cells are transduced with multiple vectors simultaneously, the resulting product will be a mixture of cells which are singly and combinatorially transduced. For example, if cells are transduced with two vectors, one comprising transgene A and one comprising transgene B, the transduced cells will be a mixture of cells expressing A alone; B alone; and cell expressing both A and B (FIG. 5B). For cells transduced with three vectors each comprising a transgene, the resulting transduced cells will be a mixture of: A alone; B alone; C alone; A and B; A and C; B and C; and cells expressing A, B and C.

The present invention involves using such a mixture as a therapeutic CAR-T-cell product. The use of a combinatorial product gives in-built flexibility which enhances the product's capacity to adapt to differences in target cells and in tumour microenvironment.

For example, the vectors may encode a combination of different CARs, which may vary in e.g. their antigen binding domains and/or costimulatory domain(s). Alternatively or in addition, one or more of the vectors may encode an activity modulator which modulates the activity of the CAR, of a cell expressing the CAR, or of a target cell. When the combinatorial CAR T-cell composition is administered in vivo, the cells will migrate to different tumour sites within the body. Whichever sub-population of CAR-T cells expressing a particular combination of CAR(s) and activity modulator(s) is best equipped to survive, persist and kill target cells at that location will have a selective advantage over the other sub-populations in the product and will win out. In this way the CAR-T cell product can adapt to tumour heterogeneity between patients and between sites in the same patient.

The method can also be used to establish which combination of vectors is optimal for generating CAR-T cells for the treatment a particular disease or disease subtype by analysing a patient to see which subpopulation of CAR-T cells in the patient shows the best persistence and/or activity.

Thus, in a first aspect, the present invention provides a method for making a cell composition which comprises step of transducing a population of cells with a mixture of at least two viral vectors, wherein at least one vector comprises a nucleic acid sequence which encodes a chimeric antigen receptor (CAR).

The method of the invention may equally be applied to cells expressing engineered T-cell receptors. Any and all of the aspects and embodiments described below are also applicable to engineered TCR-expressing cells.

The mixture may comprise two, three, four, five or more viral vectors.

Two or more viral vectors in the mixture may each comprise a CAR-encoding nucleic acid sequence. The first CAR and second CAR may have different antigen-binding domains and/or different spacers and/or different endodomains.

The CAR encoding nucleic acid of one or more viral vector(s) may encode two or more CARs. For example, the nucleic acid may encode a CAR logic gate, such as an OR gate.

The present invention provides method for making a cell composition which comprises step of transducing a population of cells with a mixture of at least two viral vectors, wherein at least one vector comprises a nucleic acid sequence which encodes a chimeric antigen receptor (CAR); and wherein at least one vector comprises a nucleic acid encoding an activity modulator which modulates the activity of the CAR, of a cell expressing the CAR, or of a target cell.

The technology of the invention, insofar as it relates to the expression of activity modulator(s) applies equally to cells for adoptive cell therapy which do not express as CAR or engineered TCR, such as tumour infiltrating lymphocytes (TILs). Any and all of the aspects and embodiments described below insofar as they relate to the expression of activity modulator(s), are also applicable generally to therapeutic T cells such as TILs.

One or more viral vectors in the mixture may comprise a nucleic acid sequence encoding both a CAR and an activity modulator, so that a cell transduced with this vector co-expresses the CAR and the activity modulator.

An activity modulator which modulates the activity of the CAR may affect the balance between phosphorylation and dephosphorylation at the CAR-expressing cell:target cell synapse. For example, the activity modulator may comprise a kinase domain capable of phosphorylating Immunoreceptor tyrosine-based activation motifs (ITAMs) in the CAR endodomain.

Alternatively the activity modulator may be capable of recruiting a kinase to be brought into proximity with the CAR, where it can phosphorylate ITAMs in the CAR endodomain.

An activity modulator which modulates the activity of CAR-expressing cell may be an intracellular molecule or may be expressed at the cell surface.

In vivo, membrane-bound immunoinhibitory receptors such as CTLA4, PD-1, LAG-3, 2B4 or BTLA1 inhibit T cell activation. The activity modulator may block or affect this inhibitory pathway.

The activity modulator may be an agent, such as an antibody, which binds to an inhibitory immunoreceptor or binds to a ligand for an inhibitory immunoreceptor.

An activity modulator which blocks or reduces the inhibition mediated by inhibitory immunoreceptors such as CTLA4, PD-1, LAG-3, 2B4 or BTLA1 may tip the balance of phosphorylation:dephosporylation at the T-cell:target cell synapse in favour of phosphorylation of ITAMs, leading to T-cell activation. For example, the activity modulator may block or reduce the phosphorylation of ITIMs in the endodomain of inhibitory receptor(s) or may block or reduce the dephosphorylation of ITAMs in the CAR signalling domain by proteins such as SHP-1 and SHP-2.

The activity modulator may be a dominant negative SHP-1 or SHP-2.

For example, the activity modulator may be a truncated protein which comprises an SH2 domain from a protein which binds a phosphorylated immunoreceptor tyrosine-based inhibition motif (ITIM), such as SHP-1 or SHP-2, but lacks a phosphatase domain.

The activity modulator may be a cytokine or chemokine such as IL12, flexiIL-12, GM-CSF, IL7, ID 5, IL21, IL2 or CCL19.

Alternatively the activity modulator may have an effect of a cytokine/chemokine signalling pathway in the CAR-expressing cell.

For example, the activity modulator may be a chimeric cytokine receptor which comprises a cytokine receptor endodomain. The exodomain may be derived from a different cytokine-receptor, or may not be from a cytokine receptor. The exodomain may bind a ligand, for example a tumour antigen or secreted factor. Presence of the ligand may cause two chains of a cytokine receptor endodomain to associate, leading to cytokine signalling.

The activity modulator may be a constitutively active chimeric cytokine receptor. The activity modulator may comprise two chains which dimerise, either spontaneously or in the presence of an agent (a chemical inducer of dimerization or CID) bringing together two cytokine receptor endodomains.

The activity modulator may affect the JAK/STAT cytokine signalling pathway. The activity modulator may comprise an inducible or constitutively active Signal Transducer and Activator of Transcription (STAT) or Janus kinase (JAK).

The activity modulator may be or comprise an adhesion molecule or a transcription factor. The transcription factor may prevent or reduce differentiation and/or exhaustion of the CAR-expressing cell.

The activity modulator of the present invention may modulate TGFβ signalling.

For example, the activity modulator may block or reduce TGFβ binding to TGFβ receptor; it may compete with TGFβ or TGFβR for binding to TGFβ R or TGFβ; alternatively it may modulate the downstream TGFβ signalling for example via SMADs. The activity modulator may be a dominant negative TGFβ receptor.

The activity modulator of the present invention may provide co-stimulatory signal to the T-cell.

For example, the activity modulatory may be a TNF receptor, a chimeric TNF receptor or a TNF receptor ligand.

The activity modulator may modulate the activity of the target cell, for example, a tumour cell.

The agent may be a toxin, a pro-drug or a pro-drug activating compound.

The activity modulator may be an enzyme which is capable of synthesising a small molecule when expressed or expressed in combination in a cell. The expression of such an enzyme or combination of enzymes in a CAR-expressing cell can confer on that cell the capacity to synthesise a small molecule, such as a small molecule which is toxic to a tumour cell.

Alternatively, the activity modulator may be an enzyme which is secreted by the CAR-expressing cell. The activity modulator be one or more enzymes which, when secreted or expressed at the cell surface, causes depletion of a molecule extracellular to the engineered cell which is:
  (i) required by a tumour cell for survival, proliferation, metastasis or chemoresistance, and/or
  (ii) detrimental to the survival, proliferation or activity of the engineered cell.

The enzyme(s) may cause the depletion of for example an amino acid or amino acid metabolite, a nucleobase (such as a nucleoside or nucleotide) or a lipid.

In the method of the invention, the mixture of viral vectors may comprise at least one vector which comprises a nucleic acid sequence which encodes a dominant negative SHP-1 or SHP-2; and at least one vector which comprises a nucleic acid sequence which encodes a dominant negative transforming growth factor (TGF)β receptor.

The mixture of viral vectors may comprise two, three, four, five or six viral vectors, at least one of which comprises a nucleic acid sequence encoding a CAR; and at least one of which comprises a nucleic acid sequence encoding an activity modulator.

The method may involve the following steps:
  (i) transducing a population of cells with a mixture of at least two viral vectors; and
  (ii) selecting CAR-expressing cells from the transduced cell population from step (i).

Alternatively, where each of the viral vectors in the mixture comprises a nucleic acid sequence encoding a CAR, it may not be necessary to select or purify CAR-expressing cells from the transduced cell population.

In a second aspect, the present invention provides a viral vector composition. The viral vector composition may comprise a mixture of two of more vectors. The vector composition may be suitable for use in the method of the first aspect of the invention.

The viral vector composition may comprise a first vector and a second vector, both of which comprise a nucleic acid sequence encoding a chimeric antigen receptor (CAR).

The CAR expressed by the first vector may be the same as the CAR expressed by the second vector. For example, the CAR expressed by the first vector may have the same antigen-binding domain as the CAR expressed by the second vector.

The first vector and/or second vector may also express an activity modulator which modulates the activity of the CAR, of a cell expressing the CAR, or of a target cell. Where the first vector and second vector both express an activity modulator, the first vector and second vector may express a different activity modulator or a different combination of activity modulators.

For example, the first vector and second vector may express one or more activity modulator(s) selected from: a dominant negative SHP-1 or SHP-2; a dominant negative transforming growth factor (TGF)β receptor; and a constitutively active chimeric cytokine receptor.

In one arrangement, the first vector may comprise a nucleic acid sequence encoding a dominant negative SHP-1 or SHP-2 and a nucleic acid sequence encoding a dominant negative transforming growth factor (TGF)β receptor; and the second vector may comprise a nucleic acid sequence encoding a constitutively active chimeric cytokine receptor.

Where the first and second vectors encode the same CAR, the CAR may have an antigen-binding domain which binds disialoganglioside (GD2).

The first vector and/or the second vector may comprise a nucleic acid sequence encoding a suicide gene.

The present invention also provides a cell composition made by a method according of the invention or made by transducing a cell with a vector composition of the invention ex vivo.

In a third aspect, the present invention provides a cell composition made by a method according to the first aspect of the invention or made by transducing a population of cells with a viral vector composition of the second aspect of the invention.

In a fourth aspect, there is provided a method for treating a disease in a subject which comprises the step of administering a cell composition according to the third aspect of the invention to the subject.

In a fifth aspect there is provided a cell composition according to the third aspect of the invention for use in treating and/or preventing a disease.

In a sixth aspect, there is provided the use of a cell composition according to third aspect of the invention in the manufacture of a medicament for treating and/or preventing a disease.

In a seventh aspect, there is provided a method for determining the optimal combination of components for a CAR-expressing cell to treat a disease, which comprises the following steps:
 (i) administering a cell composition according to the second aspect of the invention to a subject having the disease;
 (ii) monitoring the patient or samples from the patient to determine which sub-population of cells in the cell composition show the greatest level of engraftment and/or proliferation; and
 (iii) analysing the phenotype/genotype of the cells in the sub-population to ascertain the CAR(s) and/or activity modulator(s) expressed by those cells.

Further Aspects

The present invention also provides additional aspects which are summarised in the following numbered paragraphs:

1. A nucleic acid construct which comprises a nucleic acid sequence encoding a dominant negative SHP-2 and a nucleic acid sequence encoding a dominant negative TGFβ receptor.

2. A nucleic acid construct according to paragraph 1, which has the structure:
 dnSHP-coexpr-dnTGFβR, or
 dnTGFβR-coexpr-dnSHP
 in which:
 dnSHP is a nucleic acid sequence encoding dominant negative SHP-2
 "coexpr" is a nucleic acid sequences enabling coexpression of the two polypeptides as separate entities
 "dnTGFβR" is a nucleic acid sequence encoding a dominant negative TGFβ receptor.

3. A nucleic acid construct according to paragraph 1 which also comprises a nucleic acid sequence encoding a CAR.

4. A nucleic acid construct according to paragraph 3, which has the structure:
 CAR-coexpr1-dnSHP-coexpr2-dnTGFβR
 CAR-coexpr1-dnTGFβR-coexpr2-dnSHP
 dnTGFβR-coexpr1-CAR-coexpr2-dnSHP
 dnTGFβR-coexpr1-dnSHP-coexpr2-CAR
 dnSHP-coexpr1-dnTGFβR-coexpr2-CAR or
 dnSHP-coexpr1-CAR-coexpr2-dnTGFβR
 in which:
 dnSHP is a nucleic acid sequence encoding dominant negative SHP-2
 "coexpr1" and "coexpr2" which may be the same or different, are nucleic acid sequences enabling coexpression of the three polypeptides as separate entities
 "dnTGFβR" is a nucleic acid sequence encoding a dominant negative TGFβ receptor; and
 "CAR" is a nucleic acid sequence encoding a chimeric antigen receptor.

5. A nucleic acid construct according to paragraph 4, which has the structure: dnSHP-coexpr1-CAR-coexpr2-dnTGFβR 6. A nucleic acid construct according to any of paragraphs 3 to 5, wherein the CAR binds one of the following target antigens: CD19, CD22, BCMA, PSMA, CD79, GD2 or FCRL5.

7. A nucleic acid construct according to paragraph 3, which comprises a bicistronic nucleic acid sequence encoding two CARs.

8. A nucleic acid construct according to paragraph 7, which has the structure:
 dnSHP-coexpr1-CAR1-coexpr2-CAR2-coexpr3-dnTGFβR
 in which:
 "dnSHP" is a nucleic acid sequence encoding dominant negative SHP-2
 "coexpr1", "coexpr2" and "coexpr3" which may be the same or different, are nucleic acid sequences enabling coexpression of the four polypeptides as separate entities;
 "CAR1" is a nucleic acid sequence encoding a first chimeric antigen receptor;
 "CAR2" is a nucleic acid sequence encoding a second chimeric antigen receptor; and
 "dnTGFβR" is a nucleic acid sequence encoding a dominant negative TGFβ receptor.

9. A nucleic acid construct according to paragraph 7 or 8, wherein one CAR binds CD19 and the other CAR binds CD22.

10. A nucleic acid construct according to paragraph 6, wherein the CAR binds CD19 and has an antigen-binding domain which comprises
 a) a heavy chain variable region (VH) having complementarity determining regions (CDRs) with the following sequences:

```
                                    (SEQ ID No. 1)
        CDR1 - GYAFSSS;

(SEQ ID No. 2)
        CDR2 - YPGDED (SEQ ID No. 3)
        CDR3 - SLLYGDYLDY;
``` and b) a light chain variable region (VL) having CDRs with the following sequences:

```
                                        (SEQ ID No. 4)
CDR1 - SASSSVSYMH;

(SEQ ID No. 5)
CDR2 - DTSKLAS (SEQ ID No. 6)
CDR3 - QQWNINPLT.
```

11. A nucleic acid construct according to paragraph 10, wherein the antigen binding domain comprises a VH domain having the sequence shown as SEQ ID No. 7 and a VL domain having the sequence shown as SEQ ID No 8.

12. A nucleic acid construct according to any preceding paragraph which also comprises a nucleic acid sequence encoding a suicide gene.

13. A vector comprising a nucleic acid construct according to any preceding paragraph.

14. A kit of vectors comprising a first vector according to paragraph 13 and a second vector comprising a nucleic acid sequence which encodes a chimeric antigen receptor (CAR) or activity modulator.

15. A kit of vectors comprising a first vector which comprises a nucleic acid sequence encoding a dominant negative SHP-2 and a second vector which comprises a nucleic acid sequence encoding a dominant negative TGFβ receptor.

16. A kit of vectors according to paragraph 15, in which the first vector comprises a nucleic acid sequence encoding a first CAR and the second vector comprises a nucleic acid sequence encoding a second CAR.

17. A kit of vectors according to paragraph 16, wherein the first and second CARs have the same target antigen.

18. A kit of vectors according to paragraph 16, wherein the first and second CARs are the same.

19. A kit of vectors comprising a first vector according to paragraph 12, and a second vector encoding a chimeric cytokine receptor (CCR).

20. A kit of vectors according to paragraph 19, in which the first vector comprises a nucleic acid sequence encoding a first CAR and the second vector comprises a nucleic acid sequence encoding a second CAR.

21. A kit of vectors according to paragraph 20, wherein the first and second CARs have the same target antigen.

22. A kit of vectors according to paragraph 20, wherein the first and second CARs are the same.

23. A kit of vectors according to any of paragraphs 14 to 22, in which the first vector comprises a nucleic acid sequence encoding a first suicide gene and the second vector comprises a nucleic acid sequence encoding a second suicide gene.

24. A kit of vectors according to paragraph 23, wherein the first and second suicide genes are triggered by the same molecule.

25. A kit of vectors according to paragraph 23, wherein the first and second suicide genes are triggered by the different molecules.

26. A kit of vectors according to any of paragraphs 23 to 25, in which the vectors have the following structure:
Vector 1: CAR1-coexpr1-SG1-coepr2-dSHP2-coexpr3-dnTGFβR
Vector 2: CAR2-coexpr4-SG2-coepr5-CCR in which:
"CAR1" is a nucleic acid sequence encoding a first chimeric antigen receptor;
"coexpr1", "coexpr2", "coexpr3", "coexpr4", "co-expr5" which may be the same or different, are nucleic acid sequences enabling coexpression of the seven polypeptides as separate entities;
"SG1" is a nucleic acid sequence encoding a first suicide gene;
"dnSHP" is a nucleic acid sequence encoding dominant negative SHP-2;
"dnTGFβR" is nucleic acid sequence encoding a dominant negative TGFβ receptor;
"CAR2" is a nucleic acid sequence encoding a second chimeric antigen receptor which may or may not be the same as CAR1;
"SG2" is a nucleic acid sequence encoding a first suicide gene which may or may not be the same as SG1; and
"CCR" is a nucleic acid sequence encoding a chimeric cytokine receptor.

27. A kit of vectors according to any of paragraphs 14 to 26, which also comprises a third vector comprising a nucleic acid sequence encoding a cytokine.

28. A kit of vectors according to paragraph 27, wherein the cytokine is IL-12 or Flexi-IL12

29. A kit of vectors according to paragraph 28, in which the vectors have the following structure:
Vector 1: dnSHP2-coexpr1-SG1-coepr2-CAR-coexpr3-dnTGFβR
Vector 2: CCR
Vector 3: SG2-coexpr4-flexiIL12 in which:
"dnSHP" is a nucleic acid sequence encoding dominant negative SHP-2;
"coexpr1", "coexpr2", "coexpr3" and "coexpr4", which may be the same or different, are nucleic acid sequences enabling coexpression of the six polypeptides on Vectors 1 and 3 as separate entities;
"SG1" is a nucleic acid sequence encoding a first suicide gene;
"CAR" is a nucleic acid sequence encoding a chimeric antigen receptor;
"dnTGFβR" is nucleic acid sequence encoding a dominant negative TGFβ receptor;
"CCR" is a nucleic acid sequence encoding a chimeric cytokine receptor;
"SG2" is a nucleic acid sequence encoding a first suicide gene which may or may not be the same as SG1; and
"flexiIL12" is a nucleic acid sequence encoding flexi-IL-12.

30. A vector composition comprising a mixture of: a vector according to paragraph 13 and at least one other viral vector; first and second vectors as defined in any of paragraphs 14 to 26; or first, second and third vectors as defined in any of paragraphs 27 to 29.

31. A method for making a cell composition which comprises step of transducing a population of cells with a vector according to paragraph 13, a kit of vectors according to any of paragraphs 14 to 29, or a vector composition according to paragraph 30.

32. A cell which co-expresses dominant negative SHP-2 and dominant negative TGFβ receptor.

33. A cell according to paragraph 32, which also expresses one or more chimeric antigen receptor(s) (CAR(s)).

34. A cell according to paragraph 33, wherein the CAR(s) is/are as defined in any of paragraphs 6 to 11.

35. A cell composition made by a method according to paragraph 31 or comprising a plurality of cells according to any of paragraphs 32 to 34.

36. A method for treating and/or preventing a disease, which comprises the step of administering a cell composition according to paragraph 35 to a subject.

37. A method according to paragraph 36, wherein the disease is a cancer.

38. A cell composition according to paragraph 35 for use in treating and/or preventing a disease.

39. The use of a cell according to any of paragraphs 32 to 34 in the manufacture of a medicament for treating and/or preventing a disease.

40. A nucleic acid construct which comprises a nucleic acid sequence encoding a dominant negative TGFβ receptor; a nucleic acid sequence encoding a IL7; and a nucleic acid sequence encoding CCL19

41. A nucleic acid construct according to paragraph 40, which has the structure:
dnTGFβR-coexpr1-IL7-coexpr2-CCL19;
dnTGFβR-coexpr1-CCL19-coexpr2-IL7;
IL7-coexpr1-CCL19-coexpr2-dnTGFβR;
IL7-coexpr1-dnTGFβR-CCL19-coexpr2;
CCL19-coexpr1-1L7-coexpr2-dnTGFβR; or
CCL19-coexpr1-dnTGFβR-coexpr2-IL7
in which:
"dnTGFβR" is a nucleic acid sequence encoding a dominant negative TGFβ receptor;
"IL7" is a nucleic acid sequence encoding IL7
"CCL19" is a nucleic acid sequence encoding CCL19
"coexpr1" and "coexpr2", which may be the same or different, are nucleic acid sequences enabling coexpression of the three polypeptides as separate entities.

42. A nucleic acid construct according to paragraph 40 which also comprises a nucleic acid sequence encoding a CAR.

43. A nucleic acid construct according to paragraph 3, which has the structure:
CAR-coexpr1-dnTGFβR-coexpr2-IL7-coexpr3-CCL19;
in which:
dnTGFβR" is a nucleic acid sequence encoding a dominant negative TGFβ receptor;
"IL7" is a nucleic acid sequence encoding IL7
"CCL19" is a nucleic acid sequence encoding CCL19
"CAR" is a nucleic acid sequence encoding a chimeric antigen receptor
"coexpr1", "coexpr2" and "coexpr3", which may be the same or different, are nucleic acid sequences enabling coexpression of the four polypeptides as separate entities.

44. A nucleic acid construct according to any of paragraphs 3 to 5, wherein the CAR binds GD2.

45. A vector comprising a nucleic acid construct according to any of paragraphs 40 to 44.

46. A kit of vectors comprising a first vector which comprises a nucleic acid sequence encoding IL7 and a nucleic acid sequence encoding CCL19; and a second vector which comprises a nucleic acid sequence encoding a dominant negative TGFβ receptor.

47. A kit of vectors according to paragraph 46, in which both vectors also comprise a nucleic acid sequence encoding a chimeric antigen receptor (CAR).

48. A kit of vectors according to paragraph 47, wherein the CAR encoded by the first vector is the same as the CAR encoded by the second vector.

49. A kit of vectors according to paragraph 48, wherein the CAR binds GD2.

50. A method for making a cell composition which comprises step of transducing a population of cells with a vector according to paragraph 45 or a kit of vectors according to any of paragraphs 46 to 49.

51. A cell which co-expresses dominant negative TGFβ receptor, IL7 and CCL19.

52. A cell according to paragraph 51, which also expresses one or more chimeric antigen receptor(s) (CAR(s)).

53. A cell composition made by a method according to paragraph 46 or comprising a plurality of cells according to paragraph 51 or 52.

54. A method for treating and/or preventing a disease, which comprises the step of administering a cell composition according to paragraph 49 to a subject.

55. A method according to paragraph 54, wherein the disease is a cancer.

56. A cell composition according to paragraph 53 for use in treating and/or preventing a disease.

57. The use of a cell according to paragraph 51 or 52 in the manufacture of a medicament for treating and/or preventing a disease.

In the above paragraphs and the below claims, polypeptide-encoding elements of a nucleic acid construct or vector, such as "dnSHP", "dnTGFβR", "IL7", "CCL19" and "CAR" may be in any order in the construct.

The following detailed description, as it relates to nucleic acid and polypeptide sequences, polypeptide components, vectors, cells methods etc applies equally to the aspects laid out in the above paragraphs as to the aspects of the invention in the claims.

DETAILED DESCRIPTION

The present invention relates to a method for making a cell composition which comprises step of transducing a population of cells with a mixture of at least two viral vectors.

The viral vectors may, for example, be retroviral vectors or lentiviral vectors.

Retroviruses are double stranded RNA enveloped viruses mainly characterized by the ability to "reverse-transcribe" their genome from RNA to DNA. Virions measure 100-120 nm in diameter and contain a dimeric genome of identical positive RNA strands complexed with the nucleocapsid proteins. The genome is enclosed in a proteic capsid that also contains enzymatic proteins, namely the reverse transcriptase, the integrase and proteases, required for viral infection. The matrix proteins form a layer outside the capsid core that interacts with the envelope, a lipid bilayer derived from the host cellular membrane, which surrounds the viral core particle. Anchored on this bilayer, are the viral envelope glycoproteins responsible for recognizing specific receptors on the host cell and initiating the infection process. Envelope proteins are formed by two subunits, the transmembrane (TM) that anchors the protein into the lipid membrane and the surface (SU) which binds to the cellular receptors.

Based on the genome structure, retroviruses are classified into simple retroviruses, such as MLV and murine leukemia virus; or complex retroviruses, such as HIV and EIAV. Retroviruses encode four genes: gag (group specific antigen), pro (protease), pol (polymerase) and env (envelope). The gag sequence encodes the three main structural proteins: the matrix protein, nucleocapsid proteins, and capsid protein. The pro sequence encodes proteases responsible for cleaving Gag and Gag-Pol during particle assembly, budding and maturation. The pol sequence encodes the enzymes reverse transcriptase and integrase, the former catalyzing the reverse transcription of the viral genome from RNA to DNA during the infection process and the latter responsible for integrating the proviral DNA into the host cell genome. The env sequence encodes for both SU and TM subunits of the envelope glycoprotein. Additionally, retroviral genome presents non-coding cis-acting sequences such as: two LTRs (long terminal repeats), which contain elements required to drive gene expression, reverse transcription and integration into the host cell chromosome; a sequence named packaging signal (ψ) required for specific packaging of the viral RNA into newly forming virions; and a polypurine tract (PPT) that functions as the site for initiating the positive strand DNA synthesis during reverse transcription. In addition to gag, pro, pol and env, complex retroviruses, such as lentiviruses, have accessory genes including vif, vpr, vpu, nef, tat and rev that regulate viral gene expression, assembly of infectious particles and modulate viral replication in infected cells.

During the process of infection, a retrovirus initially attaches to a specific cell surface receptor. On entry into the susceptible host cell, the retroviral RNA genome is then copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular proteins. The provirus encodes the proteins and packaging machinery required to make more virus, which can leave the cell by a process known as "budding".

When enveloped viruses, such as retrovirus and lentivirus, bud out of the host cells, they take part of the host cell lipidic membrane. In this way, host-cell derived membrane proteins become part of the retroviral particle. The present invention utilises this process in order to introduce proteins of interest into the envelope of the viral particle.

Viral Vectors

Retroviruses and lentiviruses may be used as a vector or delivery system for the transfer of a nucleic acid sequence, or a plurality of nucleic acid sequences, to a target cell. The transfer can occur in vitro, ex vivo or in vivo. When used in this fashion, the viruses are typically called viral vectors.

Gamma-retroviral vectors, commonly designated retroviral vectors, were the first viral vector employed in gene therapy clinical trials in 1990 and are still one of the most used. More recently, the interest in lentiviral vectors, derived from complex retroviruses such as the human immunodeficiency virus (HIV), has grown due to their ability to transduce non-dividing cells. The most attractive features of retroviral and lentiviral vectors as gene transfer tools include the capacity for large genetic payload (up to 9 kb), minimal patient immune response, high transducing efficiency in vivo and in vitro, and the ability to permanently modify the genetic content of the target cell, sustaining a long-term expression of the delivered gene.

The retroviral vector can be based on any suitable retrovirus which is able to deliver genetic information to eukaryotic cells. For example, the retroviral vector may be an alpharetroviral vector, a gammaretroviral vector, a lentiviral vector or a spumaretroviral vector. Such vectors have been used extensively in gene therapy treatments and other gene delivery applications.

The viral vector of the present invention may be a retroviral vector, such as a gamma-retroviral vector. The viral vector may be based on human immunodeficiency virus.

The viral vector of the present invention may be a lentiviral vector. The vector may be based on a non-primate lentivirus such as equine infectious anemia virus (EIAV).

Nucleic Acid Sequences and Constructs

In the mixture of viral vectors used in the method of the present invention, each vector may comprise one or more nucleic acid sequences. For example, one or more of the vectors in the mixture may comprise a nucleic acid construct comprising a plurality of nucleic acid sequences which are co-expressed. The nucleic acid construct may, for example, be bicistronic or tri-cistronic. The nucleic acid construct may comprise 2, 3, 4 or 5 transgenes.

The nucleic acid sequences in the nucleic acid construct may be separated by a "coexpression" sequence which enables the two or more polypeptides, once translated, to be expressed separately in or on the cell.

The coexpression sequence may encode a cleavage site, such that the nucleic acid construct produces comprises two or more polypeptides joined by a cleavage site(s). The cleavage site may be self-cleaving, such that when the polypeptide is produced, it is immediately cleaved into individual polypeptides without the need for any external cleavage activity.

The cleavage site may be any sequence which enables the two or more polypeptides to become separated.

The term "cleavage" is used herein for convenience, but the cleavage site may cause the polypeptides to separate into individual entities by a mechanism other than classical cleavage. For example, for the Foot-and-Mouth disease virus (FMDV) 2A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode proteins, causes the proteins to be expressed as separate entities.

The cleavage site may be a furin cleavage site.

Furin is an enzyme which belongs to the subtilisin-like proprotein convertase family. The members of this family are proprotein convertases that process latent precursor proteins into their biologically active products. Furin is a calcium-dependent serine endoprotease that can efficiently cleave precursor proteins at their paired basic amino acid processing sites. Examples of furin substrates include proparathyroid hormone, transforming growth factor beta 1 precursor, proalbumin, pro-beta-secretase, membrane type-1 matrix metalloproteinase, beta subunit of pro-nerve growth factor and von Willebrand factor. Furin cleaves proteins just downstream of a basic amino acid target sequence (canonically, Arg-X-(Arg/Lys)-Arg' (SEQ ID No. 58)) and is enriched in the Golgi apparatus.

The cleavage site may be a Tobacco Etch Virus (TEV) cleavage site.

TEV protease is a highly sequence-specific cysteine protease which is chymotrypsin-like proteases. It is very specific for its target cleavage site and is therefore frequently used for the controlled cleavage of fusion proteins both in vitro and in vivo. The consensus TEV cleavage site is ENLYFQ\S (where '\' denotes the cleaved peptide bond) (SEQ ID No. 59). Mammalian cells, such as human cells, do not express TEV protease. Thus in embodiments in which the present nucleic acid construct comprises a TEV cleavage site and is expressed in a mammalian cell—exogenous TEV protease must also expressed in the mammalian cell.

The cleavage site may encode a self-cleaving peptide.

A 'self-cleaving peptide' refers to a peptide which functions such that when the polypeptide comprising the proteins and the self-cleaving peptide is produced, it is immediately "cleaved" or separated into distinct and discrete first and second polypeptides without the need for any external cleavage activity.

The self-cleaving peptide may be a 2A self-cleaving peptide from an aphtho- or a cardiovirus. The primary 2A/2B cleavage of the aptho- and cardioviruses is mediated by 2A "cleaving" at its own C-terminus. In apthoviruses, such as foot-and-mouth disease viruses (FMDV) and equine rhinitis A virus, the 2A region is a short section of about 18 amino acids, which, together with the N-terminal residue of protein 2B (a conserved proline residue) represents an autonomous element capable of mediating "cleavage" at its own C-terminus (Donelly et al (2001) as above).

"2A-like" sequences have been found in picornaviruses other than aptho- or cardioviruses, 'picornavirus-like' insect viruses, type C rotaviruses and repeated sequences within *Trypanosoma* spp and a bacterial sequence (Donnelly et al (2001) as above).

The cleavage site may comprise the 2A-like sequence shown in SEQ ID No. 9.

```
                                              SEQ ID No. 9
           RAEGRGSLLTCGDVEENPGP
```

The present invention provides a nucleic acid construct which comprises a nucleic acid sequence encoding a dominant negative SHP-1 or SHP-2 and a nucleic acid sequence encoding a dominant negative TGFβ receptor.

Dominant negative SHP-1 or SHP-2 and TGFβ receptors are described in more detail below.

The nucleic acid construct may have the structure:
dnSHP-coexpr-dnTGFβR, or
dnTGFβR-coexpr-dnSHP
in which:
dnSHP is a nucleic acid sequence encoding dominant negative SHP-1 or SHP-2
"coexpr" is a nucleic acid sequences enabling coexpression of the two polypeptides as separate entities
dnTGFβR is a dominant negative TGFβ receptor.

The nucleic acid construct may also comprise a nucleic acid sequence encoding a CAR. In which case the nucleic acid construct may have the structure:
CAR-coexpr1-dnSHP-coexpr2-dnTGFβR
CAR-coexpr1-dnTGFβR-coexpr2-dnSHP
dnTGFβR-coexpr1-CAR-coexpr2-dnSHP
dnTGFβR-coexpr1-dnSHP-coexpr2-CAR
dnSHP-coexpr1-dnTGFβR-coexpr2-CAR or
dnSHP-coexpr1-CAR-coexpr2-dnTGFβR
in which:
dnSHP is a nucleic acid sequence encoding dominant negative SHP-2
"coexpr1" and "coexpr2" which may be the same or different, are nucleic acid sequences enabling coexpression of the three polypeptides as separate entities
dnTGFβR is a dominant negative TGFβ receptor; and
CAR is a nucleic acid sequence encoding a chimeric antigen receptor.

Suicide Gene

A nucleic acid construct may also comprise a nucleic acid encoding a suicide gene.

Since T-cells engraft and are autonomous, a means of selectively deleting CAR T-cells in patients is desirable. Suicide genes are genetically encodable mechanisms which result in selective destruction of infused T-cells in the face of unacceptable toxicity. The earliest clinical experience with suicide genes is with the Herpes Virus Thymidine Kinase (HSV-TK) which renders T-cells susceptible to Ganciclovir. HSV-TK is a highly effective suicide gene. However, pre-formed immune responses may restrict its use to clinical settings of considerable immunosuppression such as haploidentical stem cell transplantation. Inducible Caspase 9 (iCasp9) is a suicide gene constructed by replacing the activating domain of Caspase 9 with a modified FKBP12. iCasp9 is activated by an otherwise inert small molecular chemical inducer of dimerization (CID). iCasp9 has been recently tested in the setting of haploidentical HSCT and can abort GvHD. Both iCasp9 and HSV-TK are intracellular proteins, so when used as the sole transgene, they have been co-expressed with a marker gene to allow selection of transduced cells.

WO2016/135470 describes a suicide gene which also comprises Caspase 9 but can be induced to dimerise using rapamycin or a rapamycin analog.

This suicide gene, sometimes termed Rapcasp9 or Rapacasp9, has the amino acid sequence shown as SEQ ID No. 80.

SEQ ID No. 80 (Rapcasp9)

WO2013/153391 describes a marker/suicide gene known as RQR8 which can be detected with the antibody QBEnd10 and expressing cells lysed with the therapeutic antibody Rituximab.

The sort/suicide gene RQR8 has the amino acid sequence shown as SEQ ID No. 79.

```
                                             SEQ ID No. 79
(RQR8)
CPYSNPSLCSGGGGSELPTQGTFSNVSTNVSPAKPTTTACPYSNPSLCSG

GGGSPAPRPPTPAPTIASQPLSLRPEACRPAAGGAVHTRGLDFACDIYIW

APLAGTCGVLLLSLVITLYCNHRNRRRVCKCPRPVV
```

Including a suicide gene in one or more of the vectors in the viral vector composition of the invention enables the selective ablation of a proportion of transduced cells within the subject.

For example, for two vectors A and B, transduced cells will be a mixture of cells transduced with vector A alone, cells transduced with vector B alone, and cells transduced with both vectors A and B. If vector A expresses or co-expresses a suicide gene, activating the suicide gene will cause the deletion of cells transduced with vector A alone, or with vectors A and B, but cells transduced with vector B alone will be spared.

This is particularly useful where one vector in the mixture encodes a potentially dangerous or toxic gene. If a suicide gene is included on the cassette for that vector, then in the event of an unacceptable immunological or toxic event in the patient, cells expressing the gene in question can be selectively deleted by triggering the suicide gene. Cells expressing other vector combinations which do not include the potentially dangerous gene/suicide gene combination are spared and can continue their therapeutic effect.

For example, a suicide gee may be included in a vector which expresses an immunomodulatory cytokine such as IL-12 or a constitutively active cytokine receptor (see below).

Viral Vector Composition

The present invention provides a viral vector composition which comprises a mixture viral vectors. The composition may be made by simply mixing two of more viral vectors. The composition may comprise between 2 and 10 viral vectors, for example, 2, 3, 4, 5 or 6 viral vectors.

The viral vectors in the mixture may each comprise one or more transgenes. Two or more viral vectors in the composition may overlap in one or more transgenes. For example, two viral vectors in the composition may comprise a nucleic acid sequence encoding the same CAR, but may differ in the presence or type of activity modulator(s) encoded by other nucleic acid sequences.

One or more of the viral vector(s) in the composition may comprises a nucleic acid sequence encoding a dominant negative SHP-1 or SHP-2. One or more viral vector(s) in the composition may comprise a nucleic acid sequence encoding a dominant negative TGFβ receptor. One or more viral vectors in the composition may comprise a nucleic acid sequence encoding a chimeric antigen receptor.

The viral vector composition may comprise a vector which comprises a nucleic acid sequence encoding a dominant negative SHP-1 or SHP-2 and a nucleic acid sequence encoding a dominant negative TGFβ receptor.

The viral vector composition may comprise plurality of vectors, each of which encode different activity modulator(s) or activity modulator combinations.

Chimeric Antigen Receptor

In the method of the present invention at least one vector in the mixture of viral vectors may comprise a nucleic acid sequence which encodes a chimeric antigen receptor (CAR).

Chimeric Antigen Receptors (CARS)

Figure 1:
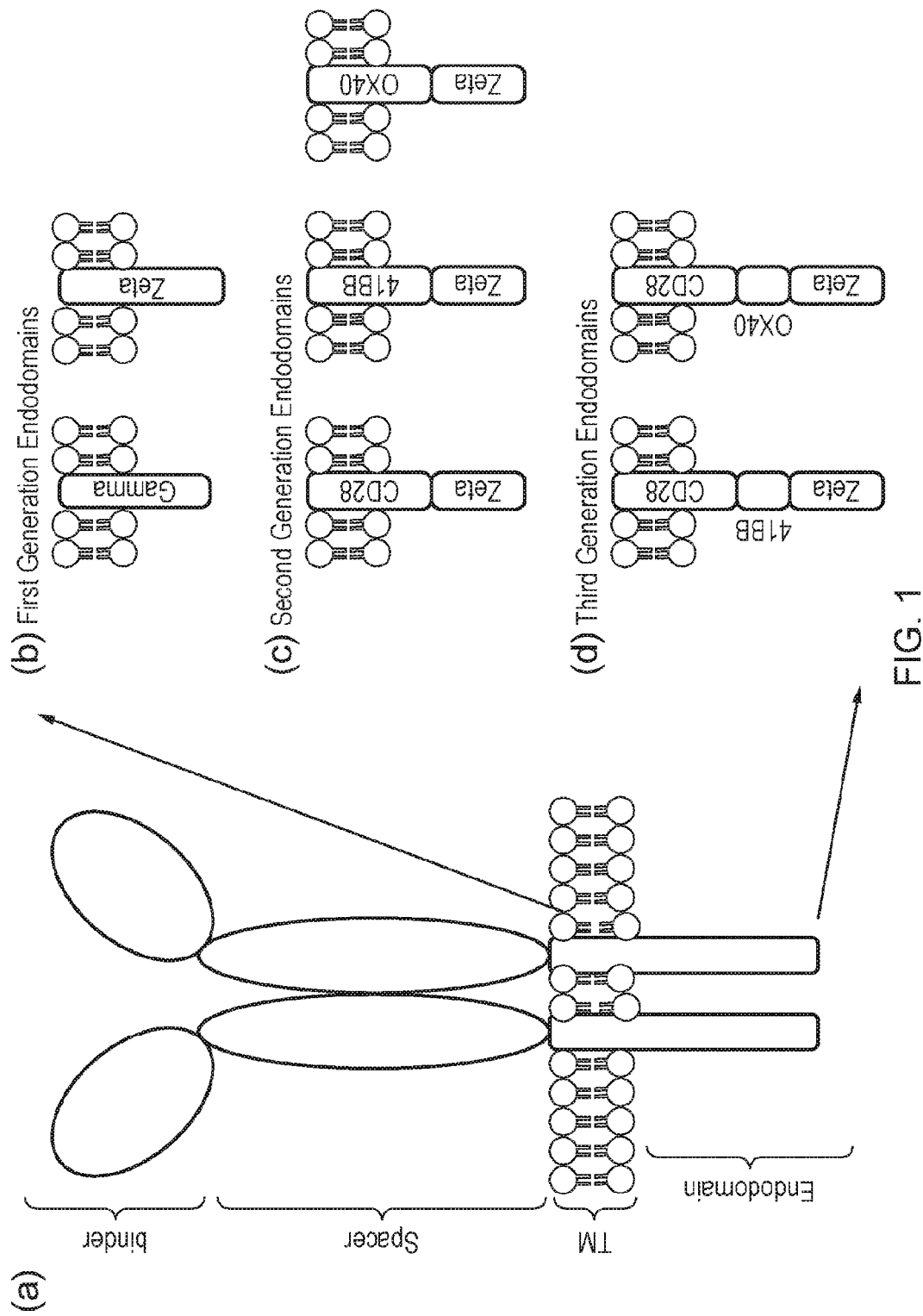
FIG. 1—Schematic diagram showing a classical chimeric antigen receptors (a) Basic schema of a chimeric antigen receptor; (b) First generation receptors; (c) Second generation receptors; (d) Third generation receptors.

CARs, which are shown schematically in FIG. 1, are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like antigen binding site. A spacer domain is usually necessary to isolate the binder from the membrane and to allow it a suitable orientation. A common spacer domain used is the Fc of IgG1. More compact spacers can suffice e.g. the stalk from CD8α and even just the IgG1 hinge alone, depending on the antigen. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41 BB which transmit survival signals. Even more potent third generation CARs have now been described which have endodomains capable of transmitting activation, proliferation and survival signals.

CAR-encoding nucleic acids may be transferred to T cells using, for example, retroviral or lentiviral vectors to generate cancer-specific T cells for adoptive cell transfer. When the CAR binds the target-antigen, this results in the transmission of an activating signal to the T-cell it is expressed on. Thus, the CAR directs the specificity and cytotoxicity of the T cell towards tumour cells expressing the targeted antigen.

Tandem CARs (TanCARs)

Bispecific CARs, known as tandem CARs or TanCARs, have been developed to target two or more cancer specific markers simultaneously. In a TanCAR, the extracellular domain comprises two antigen binding specificities in tandem, joined by a linker. The two binding specificities (scFvs) are thus both linked to a single transmembrane portion: one scFv being juxtaposed to the membrane and the other being in a distal position. When a TanCAR binds either or both of the target antigens, this results in the transmission of an activating signal to the cell it is expressed on.

Grada et al (2013, Mol Ther Nucleic Acids 2:e105) describes a TanCAR which includes a CD19-specific scFv, followed by a Gly-Ser linker and then a HER2-specific scFv. The HER2-scFv was in the juxta-membrane position, and the CD19-scFv in the distal position. The TanCAR was shown to induce distinct T cell reactivity against each of the two tumour restricted antigens. This arrangement was chosen because the respective lengths of HER2 (632 aa/125 Å) and CD19 (280aa, 65 Å) lends itself to that spatial arrangement. It was also known that the HER2 scFv bound the distal-most 4 loops of HER2.

Antigen Binding Domain

The antigen binding domain is the portion of CAR which recognizes antigen. Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain antibody; an artificial single binder such as a Darpin (designed ankyrin repeat protein); or a single-chain derived from a T-cell receptor.

Figure 4:
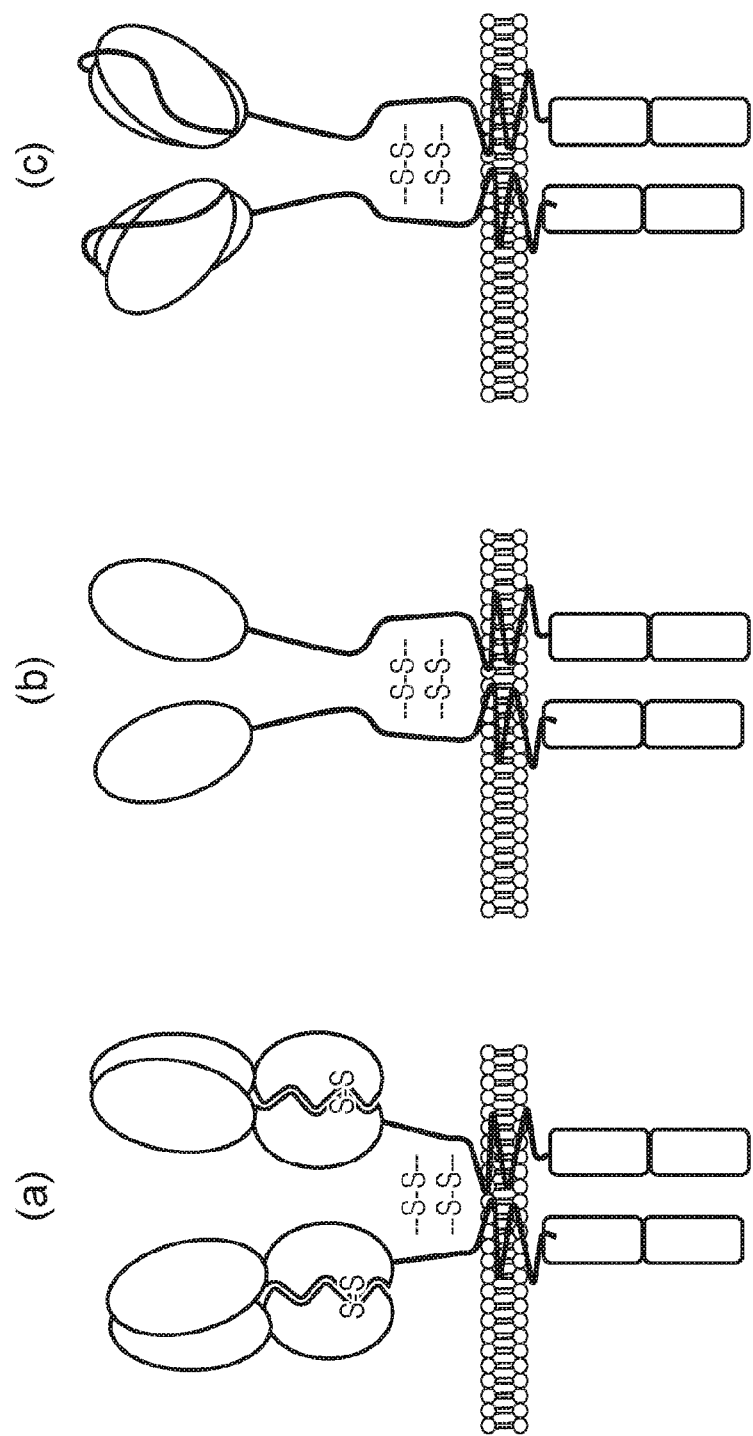
FIG. 4—Different binding domain formats of chimeric antigen receptors
 (a) Fab CAR format; (b) dAb CAR format; (c) scFv CAR format FIG. 5—Schematic diagram illustrating the difference in transduced cell compositions obtained by transduction with a single vector co-expressing two genes (A); and a mixture of two vectors, each expressing a single gene (B). When cells are transduced with a single vector having a bicistronic cassette, every cell which is successfully transduced will express both transgenes at a stoichiometry of approximately 1:1 (A). However, when cells are transduced with multiple vectors, a much more heterogeneous population is obtained: transduced cells may express the first transgene alone, the second transgene alone or both transgenes. In cells expressing both transgenes the relative level of expression of gene A and gene B is completely variable (B).

In a classical CAR, the antigen-binding domain comprises: a single-chain variable fragment (scFv) derived from a monoclonal antibody (see FIG. 4c). CARs have also been produced with domain antibody (dAb) or VHH antigen binding domains (see FIG. 4b) or which comprise a Fab fragment of, for example, a monoclonal antibody (see FIG. 4a). A FabCAR comprises two chains: one having an antibody-like light chain variable region (VL) and constant region (CL); and one having a heavy chain variable region (VH) and constant region (CH). One chain also comprises a transmembrane domain and an intracellular signalling domain. Association between the CL and CH causes assembly of the receptor.

The two chains of a Fab CAR may have the general structure:

VH-CH-spacer-transmembrane domain-intracellular signalling domain; and VL-CL or

VL-CL-spacer-transmembrane domain-intracellular signalling domain; and VH-CH

For Fab-type chimeric receptors, the antigen binding domain is made up of a VH from one polypeptide chain and a VL from another polypeptide chain.

The polypeptide chains may comprise a linker between the VH/VL domain and the CH/CL domains. The linker may be flexible and serve to spatially separate the VH/VL domain from the CH/CL domain.

The antigen-binding domain of the CAR may bind a tumour associated antigen. Various tumour associated antigens (TAA) are known, for example as shown in the following Table 1.

TABLE 1

| Cancer type | TAA |
|---|---|
| Diffuse Large B-cell Lymphoma | CD19, CD20, CD22 |
| Breast cancer | ErbB2, MUC1 |
| AML | CD13, CD33 |
| Neuroblastoma | GD2, NCAM, ALK, GD2 |
| B-CLL | CD19, CD52, CD160 |
| Colorectal cancer | Folate binding protein, CA-125 |
| Chronic Lymphocytic Leukaemia | CD5, CD19 |
| Glioma | EGFR, Vimentin |
| Multiple myeloma | BCMA, CD138 |
| Renal Cell Carcinoma | Carbonic anhydrase IX, G250 |
| Prostate cancer | PSMA |
| Bowel cancer | A33 |

The or each CAR may bind one of the following target antigens: CD19, CD22, BCMA, PSMA, GD2, CD79 or FCRL5.

CD19

An antigen binding domain of a CAR which binds to CD19 may comprise a sequence derived from one of the CD19 binders shown in Table 2.

TABLE 2

| Binder | References |
|---|---|
| HD63 | Pezzutto (Pezzutto, A. et al. J. Immunol. Baltim. Md 1950 138, 2793-2799 (1987) |
| 4g7 | Meeker et al (Meeker, T. C. et al. Hybridoma 3, 305-320 (1984) |
| Fmc63 | Nicholson et al (Nicholson, I. C. et al. Mol. Immunol. 34, 1157-1165 (1997) |
| B43 | Bejcek et al (Bejcek, B. E. et al. Cancer Res. 55, 2346-2351 (1995) |
| SJ25C1 | Bejcek et al (1995, as above) |
| BLY3 | Bejcek et al (1995, as above) |
| B4, or re-surfaced, or humanized B4 | Roguska et al (Roguska, M. A. et al. Protein Eng. 9, 895-904 (1996) |
| HB12b, optimized and humanized | Kansas et al (Kansas, G. S. & Tedder, T. F. J. Immunol. Baltim. Md 1950 147, 4094-4102 (1991); Yazawa et al (Yazawa et al Proc. Natl. Acad. Sci. U.S.A. 102, 15178-15183 (2005); Herbst et al (Herbst, R. et al. J. Pharmacol. Exp. Ther. 335, 213-222 (2010) |

Alternatively a CAR which binds CD19 may have an antigen-binding domain which comprises:
a) a heavy chain variable region (VH) having complementarity determining regions (CDRs) with the following sequences:

```
                                    (SEQ ID No. 1)
CDR1 - GYAFSSS;

(SEQ ID No. 2)
CDR2 - YPGDED (SEQ ID No. 3)
CDR3 - SLLYGDYLDY;
``` and
b) a light chain variable region (VL) having CDRs with the following sequences:

```
                                    (SEQ ID No. 4)
CDR1 - SASSSVSYMH;

(SEQ ID No. 5)
CDR2 - DTSKLAS (SEQ ID No. 6)
CDR3 - QQWNINPLT.
```

The antigen binding domain may comprise a VH domain having the sequence shown as SEQ ID No. 7 and a VL domain having the sequence shown as SEQ ID No 8.

```
                                         SEQ ID No. 7
VH sequence
QVQLQQSGPELVKPGASVKISCKASGYAFSSSWMNWVKQRPGKGLEWIGR

IYPGDEDTNYSGKFKDKATLTADKSSTTAYMQLSSLTSEDSAVYFCARSL

LYGDYLDYWGQGTTLTVSS

SEQ ID No 8
VL sequence
QIVLTQSPAIMSASPGEKVTMTCSASSSVSYMHWYQQKSGTSPKRWIYDT

SKLASGVPDRFSGSGSGTSYFLTINNMEAEDAATYYCQQWNINPLTFGAG

TKLELKR
```

CD22

A CAR which binds to CD22 may have an antigen domain derived from m971, HA22 or BL22 as described by Haso et al. (Blood; 2013; 121 (7)).

Alternatively, a CAR which binds CD22 may have an antigen binding domain as described in United Kingdom application No. 1809773.3, such as one which comprises:
a) a heavy chain variable region (VH) having complementarity determining regions (CDRs) with the following sequences:

```
                                    (SEQ ID No. 10)
CDR1 - NFAMA (SEQ ID No. 11)
CDR2 - SISTGGGNTYYRDSVKG (SEQ ID No. 12)
CDR3 - QRNYYDGSYDYEGYTMDA;
``` and
b) a light chain variable region (VL) having complementarity determining regions (CDRs) with the following sequences:

```
                                    (SEQ ID No. 13)
CDR1 - RSSQDIGNYLT (SEQ ID No. 14)
CDR2 - GAIKLED (SEQ ID No. 15)
CDR3 - LQSIQYP
```

The antigen binding domain of a CD22 CAR may comprise a VH domain having the sequence shown as SEQ ID No. 16; and a VL domain having the sequence shown as SEQ ID No. 17.

```
                                              SEQ ID No. 16
EVQLVESGGGLVQPGRSLKLSCAASGFTFSNFAMAWVRQPPTKGLEWVAS

ISTGGGNTYYRDSVKGRFTISRDDAKNTQYLQMDSLRSEDTATYYCARQR

NYYDGSYDYEGYTMDAWGQGTSVTVSS
                                              SEQ ID No. 17
DIQMTQSPSSLSASLGDRVTITCRSSQDIGNYLTWFQQKVGRSPRRMIYG

AIKLEDGVPSRFSGSRSGSDYSLTISSLESEDVADYQCLQSIQYPFTFGS

GTKLEIK
```

BCMA

A number of BCMA-targeted CARs are in clinical development, including bb2121, LCAR-B38M, MCARH171, JCARH125, P-BCMA-101, FCARH143, bb21217 and CT053.

WO2015/052538 describes a BCMA targeted CAR in which the antigen-binding domain is derived from a proliferation inducing ligand (APRIL) which is a natural ligand for BCMA.

UK Patent application No. 1815775.0 describes the VH and VL domains for 14 BCMA binding domains and their use in CARs.

PSMA

T-cells expressing CARs specific for prostate-specific membrane antigen (PSMA) are currently in clinical trial for the treatment of prostate cancer (Junhans et al (2016) Prostate 76:1257-1270).

GD2

CARs have been developed which bind disialoganglioside (GD2) a sialic acid-containing glycosphinolipid. Such CARs may, for example, be based on the GD2 binder 14g2a, or huK666 as described in WO2015/132604.

A CAR which binds GD2 may have an antigen-binding domain which comprises:

a) a heavy chain variable region (VH) having complementarity determining regions (CDRs) with the following sequences:

```
                               (SEQ ID No. 71)
    CDR1 - SYNIH;

(SEQ ID No. 72)
    CDR2 - VIWAGGSTNYNSALMS (SEQ ID No. 73)
    CDR3- RSDDYSWFAY;
``` and b) a light chain variable region (VL) having CDRs with the following sequences:

```
                               (SEQ ID No. 74)
    CDR1 - RASSSVSSSYLH;

(SEQ ID No. 75)
    CDR2 - STSNLAS (SEQ ID No. 76)
    CDR3 - QQYSGYPIT.
```

The GD2 binding domain may comprise a VH domain having the sequence shown as SEQ ID No. 77; and/or a VL domain having the sequence shown as SEQ ID No 78.

```
                                              SEQ ID No. 77
(Humanised KM666 VH sequence)
QVQLQESGPGLVKPSQTLSITCTVSGFSLASYNIHWVRQPPGKGLEWLGV

IWAGGSTNYNSALMSRLTISKDNSKNQVFLKMSSLTAADTAVYYCAKRSD

DYSWFAYWGQGTLVTVSS

SEQ ID No. 78
(Humanised KM666 VH sequence)
ENQMTQSPSSLSASVGDRVTMTCRASSSVSSSYLHWYQQKSGKAPKVWIY

STSNLASGVPSRFSGSGSGTDYTLTISSLQPEDFATYYCQQYSGYPITFG

QGTKVEIK
```

FCRL5

Commercially available monoclonal antibodies against FcRL5 are known, such as CD307e (ThermoFisher) and REA391 (Miltenyi Biotec).

WO2016090337 describes several scFv-type antigen-binding domains which bind FcRL5.

UK Patent application No. 1815775.0 describes anti-FCRL5 CARs.

CD79

A number of anti-CD79 antibodies have been previously described, such as JCB117, SN8, CB3.1, 2F2 (Polatuzumab).

United Kingdom application No. 1807870.9 describes various CD79 CARs.

Where the composition of viral vectors includes more than one vector comprising a nucleic acid sequence encoding a CAR, the CARs may have different antigen binding domains. The CARs may recognise different antigens, or the CARs may bind the same antigen but have different antigen-binding domains. CARs which bind the same antigen but have different antigen-binding domains may bind to different epitopes of the antigen and/or may have different affinities and/or on or off rates.

The affinity of a CAR for the target antigen and/or its on and off rate, can affect the capacity of a CAR to kill target cells. For example, it is reported in US 2018/0064785 that a CAR derived from an antibody with a fast on-rate and a fast off-rate allows a CAR T-cell to better serially kill target cells. By giving a patient a CAR-T cell composition which comprises a plurality of CARs against the target antigen, the CAR with the antigen-binding domain best suited to kill target cells in the patient or at a particular site in the patient will receive activation/survival/proliferation signals and will prevail. The composition of the invention gives flexibility in this regard and even allows CAR-T cell subpopulations having different CARs to "win out" at different sites within the same patient.

Intracellular T Cell Signaling Domain (Endodomain)

The CAR may comprise or associate with an activating endodomain: the signal-transmission portion of the CAR. After antigen recognition, receptors cluster and a signal is transmitted to the cell. The most commonly used endodomain component is that of CD3-zeta which contains 3 ITAMs. This transmits an activation signal to the T cell after antigen is bound. CD3-zeta may not provide a fully competent activation signal and additional co-stimulatory signaling may be needed. For example, chimeric CD28 and OX40 can be used with CD3-Zeta to transmit a proliferative/survival signal, or all three can be used together.

The endodomain of the CAR may comprise the CD28 endodomain and OX40 and CD3-Zeta endodomain.

The endodomain may comprise:
(i) an ITAM-containing endodomain, such as the endodomain from CD3 zeta; and/or
(ii) a co-stimulatory domain, such as the endodomain from CD28; and/or
(iii) a domain which transmits a survival signal, for example a TNF receptor family endodomain such as OX-40 or 4-1 BB.

An endodomain which contains an ITAM motif can act as an activation endodomain in this invention. Several proteins are known to contain endodomains with one or more ITAM motifs. Examples of such proteins include the CD3 epsilon chain, the CD3 gamma chain and the CD3 delta chain to name a few. The ITAM motif can be easily recognized as a tyrosine separated from a leucine or isoleucine by any two other amino acids, giving the signature YxxL/I (SeQ ID NO. 60). Typically, but not always, two of these motifs are separated by between 6 and 8 amino acids in the tail of the molecule (YxxL/Ix(6-8)YxxL/1). Hence, one skilled in the art can readily find existing proteins which contain one or more ITAM to transmit an activation signal. Further, given the motif is simple and a complex secondary structure is not required, one skilled in the art can design polypeptides containing artificial ITAMs to transmit an activation signal (see WO 2000/063372, which relates to synthetic signalling molecules).

A number of systems have been described in which the antigen recognition portion of the CAR is on a separate molecule from the signal transmission portion, such as those described in WO015/150771; WO2016/124930 and WO2016/030691. One or more of the viral vectors used in the method of the invention may encode such a "split CAR". Alternatively one vector may comprise a nucleic acid sequence encoding the antigen recognition portion and one vector may comprise a nucleic acid sequence encoding the intracellular signalling domain.

Where the composition of viral vectors includes more than one vector comprising a nucleic acid sequence encoding a CAR, the CARs may have different endodomains or different endodomain combinations. For example, one CAR may be a second generation CAR and one CAR may be a third generation CAR. Alternatively, both CARs may be a second generation CAR but may have different co-stimulatory domains. For example, different second generation CAR signalling domains include: 41BB-CD3ζ; OX40-CD3 and CD28-CD3ζ.

Signal Peptide

One or more nucleic acid sequences in the vector composition may encode a signal peptide so that when the CAR or activity modulator is expressed inside a cell, the nascent protein is directed to the endoplasmic reticulum and subsequently to the cell surface, where it is expressed (or secreted).

The core of the signal peptide may contain a long stretch of hydrophobic amino acids that tends to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

A CAR may have the general formula:

Signal peptide-antigen binding domain-spacer domain-transmembrane domain-intracellular T cell signaling domain (endodomain).

Spacer

The CAR may comprise a spacer sequence to connect the antigen binding domain with the transmembrane domain and spatially separate the antigen binding domain from the endodomain. A flexible spacer allows to the antigen binding domain to orient in different directions to enable antigen binding.

The spacer sequence may, for example, comprise an IgG1 Fc region, an IgG1 hinge or a CD8 stalk, or a combination thereof. The spacer may alternatively comprise an alternative sequence which has similar length and/or domain spacing properties as an IgG1 Fc region, an IgG1 hinge or a CD8 stalk.

Where the composition of viral vectors includes more than one vector comprising a nucleic acid sequence encoding a CAR, the CARs may have different spacers.

OR Gates

A cell composition of the present invention may comprise two or more CARs. This may be as a result of transduction with two or more vectors, each comprising a nucleic acid sequence encoding a CAR; or it may be as a result of transduction with a single vector which comprises a nucleic acid construct encoding two or more CARs.

A CAR may be used in a combination with one or more other activatory or inhibitory chimeric antigen receptors. For example, they may be used in combination with one or more other CARs in a "logic-gate", a CAR combination which, when expressed by a cell, such as a T cell, are capable of detecting a particular pattern of expression of at least two target antigens. If the at least two target antigens are arbitrarily denoted as antigen A and antigen B, the three possible options are as follows:

"OR GATE"—T cell triggers when either antigen A or antigen B is present on the target cell "AND GATE"—T cell triggers only when both antigens A and B are present on the target cell "AND NOT GATE"—T cell triggers if antigen A is present alone on the target cell, but not if both antigens A and B are present on the target cell Engineered T cells expressing these CAR combinations can be tailored to be exquisitely specific for cancer cells, based on their particular expression (or lack of expression) of two or more markers.

Such "Logic Gates" are described, for example, in WO2015/075469, WO2015/075470 and WO2015/075470.

An "OR Gate" comprises two or more activatory CARs each directed to a distinct target antigen expressed by a target cell. The advantage of an OR gate is that the effective targetable antigen is increased on the target cell, as it is effectively antigen A+antigen B. This is especially important for antigens expressed at variable or low density on the target cell, as the level of a single antigen may be below the threshold needed for effective targeting by a CAR-T cell. Also, it avoids the phenomenon of antigen escape. For example, some lymphomas and leukemias become CD19 negative after CD19 targeting: using an OR gate which targets CD19 in combination with another antigen provides a "back-up" antigen, should this occur. The "back up" antigen may be CD22, as described in WO2016/102965.

Activity Modulator

In the method of the present invention at least one vector in the mixture of viral vectors may comprise a nucleic acid sequence which encodes an activity modulator. When this is the case, at least a proportion of the transduced cells in the CAR-expressing cell composition of the invention will express one or more activity modulator(s). An activity modulator is a molecule made by the CAR-expressing cell which modulates the activity of the CAR, of a cell expressing the CAR, or of a target cell.

An activity modulator may be an intracellular molecule, expressed at the cell surface, or secreted by the CAR-expressing cell.

Modulating the Activity of the CAR

1. Enhancing ITAM Phosphorylation

During T cell activation in vivo (illustrated schematically in FIG. 2a), antigen recognition by the T-cell receptor (TCR) results in phosphorylation of Immunoreceptor tyrosine-based activation motifs (ITAMs) on CD3ζ. Phosphorylated ITAMs are recognized by the ZAP70 SH2 domains, leading to T cell activation.

T-cell activation uses kinetic segregation to convert antigen recognition by a TCR into downstream activation signals. Briefly: at the ground state, the signalling components on the T-cell membrane are in dynamic homeostasis whereby dephosphorylated ITAMs are favoured over phosphorylated ITAMs. This is due to greater activity of the transmembrane CD45/CD148 phosphatases over membrane-tethered kinases such as lck. When a T-cell engages a target cell through a T-cell receptor (or CAR) recognition of cognate antigen, tight immunological synapses form. This close juxtapositioning of the T-cell and target membranes excludes CD45/CD148 due to their large ectodomains which cannot fit into the synapse. Segregation of a high concentration of T-cell receptor associated ITAMs and kinases in the synapse, in the absence of phosphatases, leads to a state whereby phosphorylated ITAMs are favoured. ZAP70 recognizes a threshold of phosphorylated ITAMs and propagates a T-cell activation signal.

The process is essentially the same during CAR-mediated T-cell activation. An activating CAR comprises one or more ITAM(s) in its intracellular signalling domain, usually because the signalling domain comprises the endodomain of CD3ζ. Antigen recognition by the CAR results in phosphorylation of the ITAM(s) in the CAR signalling domain, causing T-cell activation.

Figure 2:
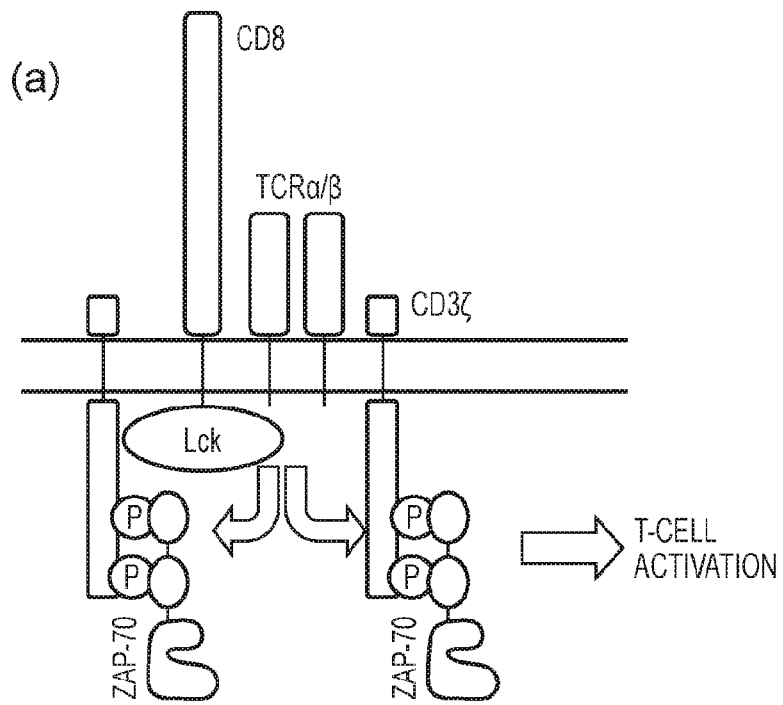
FIG. 2—Schematic diagram illustrating the mechanism of a) T-cell activation and b) T-cell inhibition in vivo FIG. 3—Schematic diagram illustrating the JAK-STAT signaling pathway (activated by α-interferon).
Figure 2:
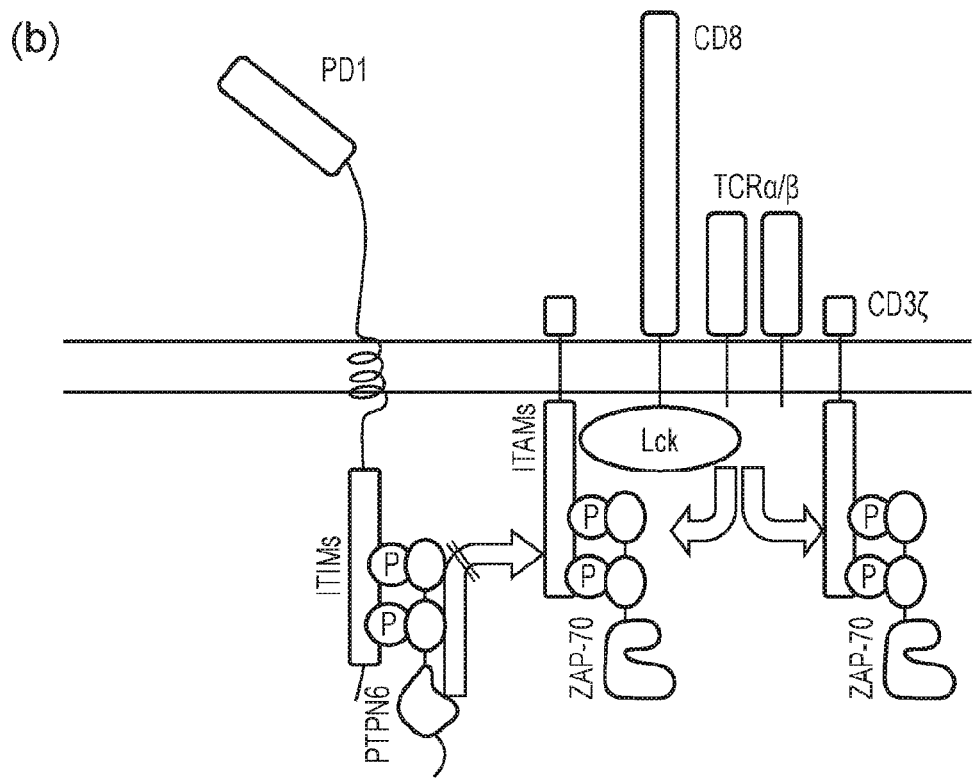

As illustrated schematically in FIG. 2b, inhibitory immune-receptors such as PD1 cause the dephosphorylation of phosphorylated ITAMs. PD1 has ITIMs in its endodomain which are recognized by the SH2 domains of molecules such as PTPN6 (SHP-1) and SHP-2. Upon recognition, PTPN6 is recruited to the juxta-membrane region and its phosphatase domain subsequently de-phosphorylates ITAM domains inhibiting immune activation.

An activity modulator capable of modulating the activity of the CAR may be capable of directly or indirectly phosphorylating the ITAM(s) in the CAR signalling domain.

1.1 Providing or Recruiting Kinase

For example, the activity modulator may be a membrane targeted molecule which either comprises a kinase domain or is capable of recruiting a separate molecule comprising a kinase domain to the vicinity of the CAR. WO2018/193231 describes various molecules having such a "phosphorylation amplifying endodomain".

An activity modulator capable of directly phosphorylating ITAMs may comprise a tyrosine kinase domain, such as a kinase domain of a Src family kinase, examples of which include Fyn, Src, Lck or a derivative thereof such as Lck (Y505F). The tyrosine kinase domains of Fyn, Src, Lck and Lck (Y505) are shown below as SEQ ID Nos. 18-21 respectively.

```
Tyrosine kinase domain Fyn (SEQ ID NO: 18)
LQLIKRLGNGQFGEVWMGTWNGNTKVAIKTLKPGTMSPESFLEEAQIMKK

LKHDKLVQLYAVVSEEPIYIVTEYMNKGSLLDFLKDGEGRALKLPNLVDM

AAQVAAGMAYIERMNYIHRDLRSANILVGNGLICKIADFGLARLIEDNEY

TARQGAKFPIKWTAPERALYGRFTIKSDVWSFGILLTELVTKGRVPYPGM

NNREVLEQVERGYRMPCPQDCPISLHELMIHCWKKDPEERPTFEYLQSFL

EDYF

Tyrosine kinase domain of Src (SEQ ID NO: 19)
LRLEVKLGQGCFGEVWMGTWNGTTRVAIKTLKPGTMSPEAFLQEAQVMKK

LRHEKLVQLYAVVSEEPIYIVTEYMSKGSLLDFLKGETGKYLRLPQLVDM

AAQIASGMAYVERMNYVHRDLRAANILVGENLVCKVADFGLARLIEDNEY

TARQGAKFPIKWTAPEAALYGRFTIKSDVWSFGILLTELTTKGRVPYPGM

VNREVLDQVERGYRMPCPPECPESLHDLMCQCWRKEPEERPTFEYLQAFL

EDYF

Tyrosine kinase domain of Lck (SEQ ID NO: 20):
LKLVERLGAGQFGEVWMGYYNGHTKVAVKSLKQGSMSPDAFLAEANLMKQ

LQHQRLVRLYAVVTQEPIYIITEYMENGSLVDFLKTPSGIKLTINKLLDM

AAQIAEGMAFIEERNYIHRDLRAANILVSDTLSCKIADFGLARLIEDNEY

TAREGAKFPIKWTAPEAINYGTFTIKSDVWSFGILLTEIVTHGRIPYPGM

TNPEVIQNLERGYRMVRPDNCPEELYQLMRLCWKERPEDRPTFDYLRSVL

EDFF

Tyrosine kinase domain of Lck_Y505F (SEQ ID NO:
21)
LKLVERLGAGQFGEVWMGYYNGHTKVAVRSLKQGSMSPDAFLAEANLMKQ

LQHQRLVRLYAVVTQEPIYIITEYMENGSLVDFLKTPSGIKLTINKLLDM

AAQIAEGMAFIEERNYIHRDLRAANILVSDTLSCKIADFGLARLIEDNEY

TAREGAKFPIKWTAPEAINYGTFTIKSDVWSFGILLTEIVTHGRIPYPGM

TNPEVIQNLERGYRMVRPDNCPEELYQLMRLCWKERPEDRPTFDYLRSVL

EDFF
```

An activity modulator capable of indirectly phosphorylating ITAMs may comprise the intracellular domain of CD4 or CD8 coreceptor.

As mentioned above, during T-cell activation, the ITAMs of CD3 (or the CAR) are phosphorylated by a Lck and then bound by ZAP70. After ZAP70 binds to CD3, co-receptors CD4 or CD8 become associated with the TCR/CD3 complex and bind to the major compatibility complex (MHC). CD4/CD8 co-receptor association with the complex stabilises the TCR-MHC peptide (MHCp) interaction and the recruited/free Lck continues the phosphorylation of CD3 elements, ZAP70, as well as many other downstream targets.

An activity modulator comprising the cytoplasmic tail of CD4 and CD8 will amplify the signal generated by the CAR by recruiting Lck, which is essential for activating many molecular components of the signaling cascade of an activated T cell. The sequences of the intracellular domain of human CD4 and CD8 are shown below as SEQ ID No. 22 and 23

```
Cytoplasmic tail of CD4
                                        (SEQ ID NO: 22)
CVRCRHRRRQAERMSQIKRLLSEKKTCQCPHRFQKTCSPI Cytoplasmic tail of CD8
                                        (SEQ ID NO: 23)
LYCNHRNRRRVCKCPRPVVKSGDKPSLSARYV
```

An activity modulator which modulated the activity of the CAR may be membrane-tethered. In this respect, such an activity modulator may comprise a transmembrane domain or a myristoylation sequence.

Modulating the Activity of the CAR-T Cell

1. Checkpoint Inhibition

An activity modulator capable of modulating the activity of the CAR-expressing cell may block or reduce the inhibition of CAR-mediated T-cell activation mediated by inhibitory immunoreceptors such as CTLA4, PD-1, LAG-3, 2B4 or BTLA1 (as mentioned above and illustrated schematically in FIG. 2b).

The activity modulator may be an agent, such as an antibody, which binds to an inhibitory immunoreceptor or binds to a ligand for an inhibitory immunoreceptor. The activity modulator may bind to CTLA4, PD-1, LAG-3, 2B4 or BTLA1, or bind to a ligand for CTLA4, PD-1, LAG-3, 2B4 or BTLA1.

PD-1/PD-L1

In the cancer disease state, the interaction of PD-L1 on the tumour cells with PD-1 on a T-cell reduces T-cell activation, as described above, thus hampering the immune system in its efforts to attack the tumour cells. Use of an inhibitor that blocks the interaction of PD-L1 with the PD-1 receptor can prevent the cancer from evading the immune system in this way. Several PD-1 and PD-L1 inhibitors are being trialled within the clinic for use in advanced melanoma, non-small cell lung cancer, renal cell carcinoma, bladder cancer and Hodgkin lymphoma, amongst other cancer types. Some such inhibitors are now approved, including the PD1 inhibitors Nivolumab and Pembrolizumab and the PD-L1 inhibitors Atezolizumab, Avelumab and Durvalumab.

CTLA4

CTLA4 is a member of the immunoglobulin superfamily that is expressed by activated T cells and transmits an inhibitory signal to T cells. CTLA4 is homologous to the T-cell co-stimulatory protein, CD28, and both molecules bind to CD80 and CD86, also called B7-1 and B7-2 respectively, on antigen-presenting cells. CTLA-4 binds CD80 and CD86 with greater affinity and avidity than CD28 thus enabling it to outcompete CD28 for its ligands. CTLA4 transmits an inhibitory signal to T cells, whereas CD28 transmits a stimulatory signal.

Antagonistic antibodies against CTLA4 include ipilimumab and tremelimumab.

LAG-3

Lymphocyte-activation gene 3, also known as LAG-3 and CD223, is an immune checkpoint receptor with diverse biologic effects on T-cell function.

Antibodies to LAG3 include relatlimab, which currently in phase 1 clinical testing and a number of others in preclinical development. LAG-3 may be a better checkpoint inhibitor target than CTLA-4 or PD-1 since antibodies to these two checkpoints only activate effector T cells, and do not inhibit Treg activity, whereas an antagonist LAG-3 antibody can both activate T effector cells (by downregulating the LAG-3 inhibiting signal into pre-activated LAG-3+ cells) and inhibit induced (i.e. antigen-specific) Treg suppressive activity. Combination therapies are also ongoing involving LAG-3 antibodies and CTLA-4 or PD-1 antibodies.

1.2 Dominant Negative SHP

An activity modulator which blocks or reduces the inhibition mediated by inhibitory immunoreceptors such as CTLA4, PD-1, LAG-3, 2B4 or BTLA1 may tip the balance of phosphorylation:dephosporylation at the T-cell:target cell synapse in favour of phosphorylation of ITAMs, leading to T-cell activation. For example, the activity modulator may block or reduce the phosphorylation of ITIMs in the endodomain of inhibitory receptor(s) or may block or reduce the dephosphorylation of ITAMs in the CAR signalling domain by proteins such as SHP-1 and SHP-2.

WO2016/193696 describes various different types of protein capable of modulating the balance of phosphorylation:dephosporylation at the T-cell:target cell synapse. For example, the activity modulator may comprise a truncated form of SHP-1 or SHP-2 which comprises one or both SH2 domains, but lacks the phosphatase domain. When expressed in a CAR-T cell, these molecules act as dominant negative versions of wild-type SHP-1 and SHP-2 and compete with the endogenous molecule for binding to phosphorylated ITIMs.

The activity modulator may be a truncated protein which comprises an SH2 domain from a protein which binds a phosphorylated immunoreceptor tyrosine-based inhibition motif (ITIM) but lacks a phosphatase domain. The truncated protein may comprise one or both SHP-1 SH2 domain(s) but lack the SHP-1 phosphatase domain. Alternatively the truncated protein may comprise one or both SHP-2 SH2 domain(s) but lack the SHP-2 phosphatase domain.

SHP-1

Src homology region 2 domain-containing phosphatase-1 (SHP-1) is a member of the protein tyrosine phosphatase family. It is also known as PTPN6.

The N-terminal region of SHP-1 contains two tandem SH2 domains which mediate the interaction of SHP-1 and its substrates. The C-terminal region contains a tyrosine-protein phosphatase domain.

SHP-1 is capable of binding to, and propagating signals from, a number of inhibitory immune receptors or ITIM containing receptors. Examples of such receptors include, but are not limited to, PD1, PDCD1, BTLA4, LILRB1, LAIR1, CTLA4, KIR2DL1, KIR2DL4, KIR2DL5, KIR3DL1 and KIR3DL3.

Human SHP-1 protein has the UniProtKB accession number P29350.

An activity modulator may comprise or consist of the SHP-1 tandem SH2 domain which is shown below as SEQ ID NO: 24.

```
SHP-1 SH2 complete domain
                                        (SEQ ID NO: 24)
MVRWFHRDLSGLDAETLLKGRGVHGSFLARPSRKNQGDFSLSVRVGDQ

VTHIRIQNSGDFYDLYGGEKFATLTELVEYYTQQQGVLQDRDGTIIHL

KYPLNCSDPTSERWYHGHMSGGQAETLLQAKGEPWTFLVRESLSQPGD

FVLSVLSDQPKAGPGSPLRVTHIKVMCEGGRYTVGGLETFDSLTDLVE

HFKKTGIEEASGAFVYLRQPYY
```

SHP-1 has two SH2 domains at the N-terminal end of the sequence, at residues 4-100 and 110-213. An activity modulator may comprise one or both of the sequences shown as SEQ ID No. 25 and 26.

SHP-1 SH2 1
(SEQ ID NO: 25)
WFHRDLSGLDAETLLKGRGVHGSFLARPSRKNQGDFSLSVRVGDQVTH

IRIQNSGDFYDLYGGEKFATLTELVEYYTQQQGVLQDRDGTIIHLKYP

L

SHP-2 SH2 2
(SEQ ID No. 26)
WYHGHMSGGQAETLLQAKGEPWTFLVRESLSQPGDFVLSVLSDQPKAG

PGSPLRVTHIKVMCEGGRYTVGGLETFDSLTDLVEHFKKTGIEEASGA

FVYLRQPY

The activity modulator may comprise a variant of SEQ ID NO: 24, 25 or 26 having at least 80, 85, 90, 95, 98 or 99% sequence identity, provided that the variant sequence is a SH2 domain sequence has the required properties. In other words, the variant sequence should be capable of binding to the phosphorylated tyrosine residues in the cytoplasmic tail of at least one of PD1, PDCD1, BTLA4, LILRB1, LAIR1, CTLA4, KIR2DL1, KIR2DL4, KIR2DL5, KIR3DL1 or KIR3DL3 which allow the recruitment of SHP-1.

SHP-2

SHP-2, also known as PTPN11, PTP-1D and PTP-2C is a member of the protein tyrosine phosphatase (PTP) family. Like PTPN6, SHP-2 has a domain structure that consists of two tandem SH2 domains in its N-terminus followed by a protein tyrosine phosphatase (PTP) domain. In the inactive state, the N-terminal SH2 domain binds the PTP domain and blocks access of potential substrates to the active site. Thus, SHP-2 is auto-inhibited. Upon binding to target phosphotyrosyl residues, the N-terminal SH2 domain is released from the PTP domain, catalytically activating the enzyme by relieving the auto-inhibition.

Human SHP-2 has the UniProtKB accession number P35235-1.

An activity modulator may comprise or consist of the SHP-1 tandem SH2 domain which is shown below as SEQ ID NO: 29. SHP-1 has two SH2 domains at the N-terminal end of the sequence, at residues 6-102 and 112-216. An activity modulator may comprise one or both of the sequences shown as SEQ ID No. 27 and 28.

SHP-2 first SH2 domain
(SEQ ID NO: 27)
WFHPNITGVEAENLLLTRGVDGSFLARPSKSNPGDFTLSVRRNGAVTH

IKIQNTGDYYDLYGGEKFATLAELVQYYMEHHGQLKEKNGDVIELKYP

L

SHP-2 second SH2 domain
(SEQ ID No. 28)
WFHGHLSGKEAEKLLTEKGKHGSFLVRESQSHPGDFVLSVRTGDDKGE

SNDGKSKVTHVMIRCQELKYDVGGGERFDSLTDLVEHYKKNPMVETLG

TVLQLKQPL

SHP-2 both SH2 domains
(SEQ ID No. 29)
WFHPNITGVEAENLLLTRGVDGSFLARPSKSNPGDFTLSVRRNGAVTH

IKIQNTGDYYDLYGGEKFATLAELVQYYMEHHGQLKEKNGDVIELKYP

LNCADPTSERWFHGHLSGKEAEKLLTEKGKHGSFLVRESQSHPGDFVL

SVRTGDDKGESNDGKSKVTHVMIRCQELKYDVGGGERFDSLTDLVEHY

KKNPMVETLGTVLQLKQPL

The activity modulator may comprise a variant of SEQ ID NO: 27, 28 or 29 having at least 80, 85, 90, 95, 98 or 99% sequence identity, provided that the variant sequence is a SH2 domain sequence has the required properties. In other words, the variant sequence should be capable of binding to the phosphorylated tyrosine residues in the cytoplasmic tail of at least one of PD1, PDCD1, BTLA4, LILRB1, LAIR1, CTLA4, KIR2DL1, KIR2DL4, KIR2DL5, KIR3DL1 or KIR3DL3 which allow the recruitment of SHP-2.

3. Cytokines and Cytokine Signalling

An activity modulator may be a cytokine or chemokine. A cytokine may modulate the activity of the CAR-expressing cell and/or modulate the tumour microenvironment.

The activity modulator may be a cytokine or chemokine be selected from: 1L12, flexiIL12, GM-CSF, 1L7, 1L15, 1L21, 1L2 and CCL19. In particular, the agent may be IL-7 or IL-12.

IL-7 is a cytokine important for B and T cell development. IL-7 stimulates the differentiation of multipotent (pluripotent) hematopoietic stem cells into lymphoid progenitor cells and stimulates proliferation of all cells in the lymphoid lineage (B cells, T cells and NK cells.

IL-7 and the hepatocyte growth factor (HGF) form a heterodimer that functions as a pre-pro-B cell growth-stimulating factor. This cytokine is found to be a cofactor for V(D)J rearrangement of the T cell receptor beta (TCRβ) during early T cell development. The amino acid sequence of human 11-7 is available from UniProt (Accession No. P13232)

Interleukin 12 (IL-12) is a potent immunomodulatory cytokine of particular interest for modulating the tumour microenvironment redirecting the immune response against cancer. IL-12 is systemically toxic therefore methods for producing IL-12 locally are of interest. PCT/GB2018/052204 describes a construct where production of an immunomodulatory cytokine such as IL-12 is under the control of a promoter which is activated in the presence of an environmental metabolite, such as kynurenine. Selective production of IL-12 in the presence of an metabolite such as kynurenine enables local production of IL-12 by the CAR- or TCR-expressing cell, only when it is present in the tumour microenvironment.

Alternatively, the immunomodulatory cytokine may be placed downstream of a frame-slip motif or a translational readthrough motif. This provides a means of controlling cytokine expression and reducing the level of expression of cytokine relative to the CAR.

A frame-slip motif (FSM) may comprise a repeat of uracil, thymine or guanine bases, such as the sequence UUUUUUU (SEQ ID No. 61).

A frame-slip motif may also comprise a stop codon. For example, a FSM may comprise one of the following sequences:

UUUUUUUGA (SEQ ID NO. 62)

UUUUUUUAG (SEQ ID NO. 63)

UUUUUUUAA. (SEQ ID NO. 64)

A translational readthrough motif (TRM) may comprise the sequence STOP-CUAG or STOP-CAAUUA, in which "STOP" is a stop codon. For example, a translational readthrough motif may comprise one of the following sequences:

UGA-CUAG (SEQ ID No. 65)

UAG-CUAG (SEQ ID No. 66)

UAA-CUAG (SEQ ID No. 67)

UGA-CAAUUA (SEQ ID No. 68)

UAG-CAAUUA (SEQ ID No. 69)

UAA-CAAUUA (SEQ ID No. 70)

IL-12 is a heterodimeric cytokine encoded by two separate genes, IL-12A (p35) and IL-12B (p40). The active heterodimer (referred to as 'p70'), is formed following protein synthesis. The activity modulator may be "flexi-IL12", which is a fusion between the IL-12α and IL-12β subunits, joined by a linker. A suitable flexi-IL-12 sequence is shown below as SEQ ID No. 81.

(a flexi-IL-12 sequence)
SEQ ID No. 81
MWIWELKKDVYVVELDWYPDAPGEMVVLTCDTPEEDGITWTLDQSS

EVLGSGKTLTIQVKEFGDAGQYTCHKGGEVLSHSLLLLHKKEDGIW

STDILKDQKEPKNKTFLRCEAKNYSGRFTCWWLTTISTDLTFSVKS

SRGSSDPQGVTCGAATLSAERVRGDNKEYEYSVECQEDSACPAAEE

SLPIEVMVDAVHKLKYENYTSSFFIRDIIKPDPPKNLQLKPLKNSR

QVEVSWEYPDTWSTPHSYFSLTFCVQVQGKSKREKKDRVFTDKTSA

TVICRKNASISVRAQDRYYSSSWSEWASVPCSGGGGSGGGGSGGGG

SRNLPLATPDPGMFPCLHHSQNLLRAVSNMLQKARQTLEFYPCTSE

EIDHEDITKDKTSTVEACLPLELTKNESCLNSRETSFITNGSCLAS

RKTSFMMALCLSSIYEDSKMYQVEFKTMNAKLLMDPKRQIFLDQNM

LAVIDELMQALNFNSETVPQKSSLEEPDFYKTKIKLCILLHAFRIR

AVTIDRVMSYLNAS

In SEQ ID No. 81, the serine-glycine linker is in bold and underlined.

The activity modulator is the present invention may be a cytokine which is selectively expressed depending the presence of an environmental metabolite in the microenvironment of the cell. The environmental metabolite may activate the aryl hydrocarbon receptor (AHR). The environmental metabolite may be a tryptophan metabolite such as is kynurenine.

Alternatively, the agent may affect the expression or activity of a cytokine or chemokine. For example, the agent may be a dominant negative version of a cytokine or chemokine. A dominant negative version may, for example, be a mutated or truncated version of the cytokine/chemokine which binds to the receptor and competes with the wild-type cytokine/chemokine but does not trigger cytokine/chemokine signalling.

For example, the agent may be a dominant negative version of a cytokine receptor or chemokine receptor. A dominant negative version may, for example, be a mutated or truncated version of the cytokine/chemokine receptor which binds to the cytokine blocking its binding to the wild-type cytokine/chemokine receptor.

Alternatively, the agent may be an antibody or antibody fragment which blocks or otherwise modulates a cytokine or chemokine signalling pathway.

The activity modulator may be a chimeric cytokine receptor which comprises a cytokine receptor endodomain.

The activity modulator may comprise the exodomain from an immunoinhibitory cytokine, such as IL-4, fused to the endodomain from a cytokine such as IL-7 which enhances T-cell proliferation (Leen et al (2014) Mol. Ther. 22:1211-1220).

The activity modulator may be a chemokine such as CCL19. Chemokine (C-C motif) ligand 19 (CCL19) is a small cytokine belonging to the CC chemokine family that is also known as EBI1 ligand chemokine (ELC) and macrophage inflammatory protein-3-beta (MIP-3-beta). CCL19 elicits its effects on its target cells by binding to the chemokine receptor chemokine receptor CCR7. It attracts certain cells of the immune system, including dendritic cells and antigen-engaged B cells and CCR7+ central-memory T-Cells. The amino acid sequence for human CCL19 is available from UniProt (Accession number 099731).

3.1 Chimeric Cytokine Receptors

Alternatively, the activity modulator may comprise a non-cytokine receptor exodomain. WO2017/029512 describes chimeric cytokine receptors (CCR) comprising: an exodomain which binds to a ligand selected from a tumour secreted factor, a chemokine and a cell-surface antigen; and a cytokine receptor endodomain.

The chimeric cytokine receptor may comprise two polypeptides:
 (i) a first polypeptide which comprises:
  (a) a first antigen-binding domain which binds a first epitope of the ligand
  (b) a first chain of the cytokine receptor endodomain; and
 (ii) a second polypeptide which comprises:
  (a) a second antigen-binding domain which binds a second epitope of the ligand (b) a second chain of the cytokine-receptor endodomain.

Alternatively the chimeric cytokine receptor which comprises two polypeptides:
 (i) a first polypeptide which comprises:
  (a) a heavy chain variable domain (VH)
  (b) a first chain of the cytokine receptor endodomain; and
 (ii) a second polypeptide which comprises:
  (a) a light chain variable domain (VL)
  (b) a second chain of the cytokine-receptor endodomain.

For example, the cytokine receptor endodomain may comprise:
  (i) IL-2 receptor β-chain endodomain
  (ii) IL-7 receptor α-chain endodomain;
  (iii) IL-15 receptor α-chain endodomain; or
  (iv) common γ-chain receptor endodomain.

The cytokine receptor endodomain may comprise (i), (ii) or (iii); and (iv).

The cytokine receptor endodomain may comprise the α-chain endodomain and the β-chain endodomain from granulocyte-macrophage colony-stimulating factor receptor (GMCSF-R)

The ligand may be a tumour secreted factor, for example a tumour secreted factor selected from: prostate-specific antigen (PSA), carcinoembryonic antigen (CEA), vascular endothelial growth factor (VEGF) and CA125.

The ligand may be a chemokine, for example a chemokine selected from chemokine selected from: CXCL12, CCL2, CCL4, CCL5 and CCL22.

The ligand may be a cell-surface molecule, such as a transmembrane protein. The ligand may be, for example, CD22.

Constitutively Active Chimeric Cytokine Receptors

The activity modulator may be a constitutively active chimeric cytokine receptor. The activity modulator may comprise two chains which dimerise, either spontaneously or in the presence of an agent (a chemical inducer of dimerization or CID) bringing together two cytokine receptor endodomains.

The activity modulator may therefore comprise a dimerization domain; and a cytokine receptor endodomain.

Dimerisation may occur spontaneously, in which case the chimeric transmembrane protein will be constitutively active. Alternatively, dimerization may occur only in the presence of a chemical inducer of dimerization (CID) in which case the transmembrane protein only causes cytokine-type signalling in the presence of the CID.

Suitable dimerization domains and CIDs are described in WO2015/150771, the contents of which are hereby incorporated by reference.

For example, one dimerization domain may comprise the rapamycin binding domain of FK-binding protein 12 (FKBP12), the other may comprise the FKBP12-Rapamycin Binding (FRB) domain of mTOR; and the CID may be rapamycin or a derivative thereof.

One dimerization domain may comprise the FK506 (Tacrolimus) binding domain of FK-binding protein 12 (FKBP12) and the other dimerization domain may comprise the cyclosporin binding domain of cylcophilin A; and the CID may be an FK506/cyclosporin fusion or a derivative thereof.

One dimerization domain may comprise an oestrogen-binding domain (EBD) and the other dimerization domain may comprise a streptavidin binding domain; and the CID may be an estrone/biotin fusion protein or a derivative thereof.

One dimerization domain may comprise a glucocorticoid-binding domain (GBD) and the other dimerization domain may comprise a dihydrofolate reductase (DHFR) binding domain; and the CID may be a dexamethasone/methotrexate fusion protein or a derivative thereof.

One dimerization domain may comprise an O6-alkylguanine-DNA alkyltransferase (AGT) binding domain and the other dimerization domain may comprise a dihydrofolate reductase (DHFR) binding domain; and the CID may be an O6-benzylguanine derivative/methotrexate fusion protein or a derivative thereof.

One dimerization domain may comprise a retinoic acid receptor domain and the other dimerization domain may comprise an ecodysone receptor domain; and the CID may be RSL1 or a derivative thereof.

Where the dimerization domain spontaneously heterodimerizes, it may be based on the dimerization domain of an antibody. In particular it may comprise the dimerization portion of a heavy chain constant domain (CH) and a light chain constant domain (CL). The "dimerization portion" of a constant domain is the part of the sequence which forms the inter-chain disulphide bond.

The chimeric cytokine receptor may comprise the Fab portion of an antibody as exodomain. In this respect, the chimeric antigen may comprise two polypeptides:
  (i) a first polypeptide which comprises:
    (a) a heavy chain constant domain (CH)
    (b) a first chain of the cytokine receptor endodomain; and
  (ii) a second polypeptide which comprises:
    (a) a light chain constant domain (CL)
    (b) a second chain of the cytokine-receptor endodomain.

The cytokine receptor endodomain may comprise:
  (i) IL-2 receptor β-chain endodomain
  (ii) IL-7 receptor α-chain endodomain; or
  (iii) IL-15 receptor α-chain endodomain; and/or
  (iv) common γ-chain receptor endodomain.

The cytokine receptor endodomain may comprise the α-chain endodomain and the β-chain endodomain from granulocyte-macrophage colony-stimulating factor receptor (GMCSF-R)

A constitutively active CCR having an IL-2, IL-7 or GM-CSF receptor endodomain may have one of the following structures:
  Fab_CCR_IL2: HuLightKappa-IL2RgTM-IL2RgEndo-2A-HuCH1-1L2bTM-IL2RbENDO
  Fab_CCR_IL7: HuLightKappa-IL2RgTM-IL2RgEndo-2A-HuCH1-1L7RaTM-IL7RaENDO
  Fab_CCR GMCSF:
  HuLightKappa-GMCSFRbTM-GMCSFRbEndo-2A-HuCH1-GMCSFRaTM-GMCSFRaENDO In which:
  HuLightKappa is a human light kappa chain
  IL2RgTM is a transmembrane domain from human IL2R common gamma chain
  IL2RgEndo is an endodomain derived from human IL2R common gamma chain
  2A is a sequence enabling the co-expression of the two polypeptides, which may be a self cleaving peptide such as a 2A peptide
  HuCH1 is a human CH1
  IL2bTM is a transmembrane domain from human IL-2R beta
  IL2RbENDO is an endodomain from human IL2R beta
  IL7RaTM is a transmembrane domain from human IL-7R alpha
  IL7RaENDO is an endodomain from human IL-7R alpha
  GMCSFRbTM is a transmembrane domain from Human GM-CSFR common beta chain
  GMCSFRbEndo is an endodomain from GM-CSFR common beta chain
  GMCSFRaTM is a transmembrane domain from Human GF-CSFR alpha
  GMCSFRaENDO is an endodomain Derived from Human GM-CSFR alpha The sequences for the components for making a constitutively active cytokine receptor as shown below as SEQ ID NO. 30 to 43.

```
SEQ ID No. 30 (Human Light Kappa Chain)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC

SEQ ID No. 31 (Human Hinge)
EPKSCDKTHTCPPCPKDPK

SEQ ID No. 32 (Human CH1)
STKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKRV

SEQ ID No. 33 (Transmembrane domain from human
IL2R common gamma chain):
VVISVGSMGLIISLLCVYFWL SEQ ID No. 34 (Transmembrane domain from human
IL-2R beta)
IPWLGHLLVGLSGAFGFIILVYLLI SEQ ID No. 36 (Transmembrane domain from human
IL-7R alpha)
PILLTISILSFFSVALLVILACVLW SEQ ID No. 37 (Transmembrane domain from Human
GF-CSFR alpha)
NLGSVYIYVLLIVGTLVCGIVLGFLF SEQ ID No. 38 (Transmembrane domain from Human
GM-CSFR common beta chain)
VLALIVIFLTIAVLLAL SEQ ID No. 39 (Endodomain from human IL2R common
gamma chain)
ERTMPRIPTLKNLEDLVTEYHGNFSAWSGVSKGLAESLQPDYSERLCLVS

EIPPKGGALGEGPGASPCNQHSPYWAPPCYTLKPET

SEQ ID No. 40 (Endodomain from human IL-2R beta)
NCRNTGPWLKKVLKCNTPDPSKFFSQLSSEHGGDVQKWLSSPFPSSSFSP

GGLAPEISPLEVLERDKVTQLLLQQDKVPEPASLSSNHSLTSCFTNQGYF

FFHLPDALEIEACQVYFTYDPYSEEDPDEGVAGAPTGSSPQPLQPLSGED

DAYCTFPSRDDLLLFSPSLLGGPSPPSTAPGGSGAGEERMPPSLQERVPR

DWDPQPLGPPTPGVPDLVDFQPPPELVLREAGEEVPDAGPREGVSFPWSR

PPGQGEFRALNARLPLNTDAYLSLQELQGQDPTHLV

SEQ ID No. 41 (Endodomain from human IL-7R alpha)
KKRIKPIVWPSLPDHKKTLEHLCKKPRKNLNVSFNPESFLDCQIHRVDDI

QARDEVEGFLQDTFPQQLEESEKQRLGGDVQSPNCPSEDVVITPESFGRD

SSLTCLAGNVSACDAPILSSSRSLDCRESGKNGPHVYQDLLLSLGTTNST

LPPPFSLQSGILTLNPVAQGQPILTSLGSNQEEAYVTMSSFYQNEQ

SEQ ID No. 42 (Endodomain Derived from Human
GM-CSFR alpha)
KRFLRIQRLFPPVPQIKDKLNDNHEVEDEIIWEEFTPEEGKGYREEVLTV

KEIT

SEQ ID No. 43 (Endodomain from GM-CSFR common
beta chain)
RFCGIYGYRLRRKWEEKIPNPSKSHLFQNGSAELWPPGSMSAFTSGSPPH

QGPWGSRFPELEGVFPVGFGDSEVSPLTIEDPKHVCDPPSGPDTTPAASD

LPTEQPPSPQPGPPAASHTPEKQASSFDFNGPYLGPPHSRSLPDILGQPE

PPQEGGSQKSPPPGSLEYLCLPAGGQVQLVPLAQAMGPGQAVEVERRPSQ

GAAGSPSLESGGGPAPPALGPRVGGQDQKDSPVAIPMSSGDTEDPGVASG

YVSSADLVFTPNSGASSVSLVPSLGLPSDQTPSLCPGLASGPPGAPGPVK

SGFEGYVELPPIEGRSPRSPRNNPVPPEAKSPVLNPGERPADVSPTSPQP

EGLLVLQQVGDYCFLPGLGPGPLSLRSKPSSPGPGPEIKNLDQAFQVKKP

PGQAVPQVPVIQLFKALKQQDYLSLPPWEVNKPGEVC
```

The activity modulator may comprise a variant of one or more of SEQ ID NO: 30 to 43 having at least 80, 85, 90, 95, 98 or 99% sequence identity, provided that the variant sequence has the required properties. For example, a variant CH or CL sequence should retain the capacity to dimerise with a CL/CH containing-chain. A variant chain from a cytokine receptor endodomain should retain the capacity to trigger cytokine-mediated signalling when coupled with the reciprocal chain for that cytokine receptor.

3.3 JAK/STAT

Figure 3:
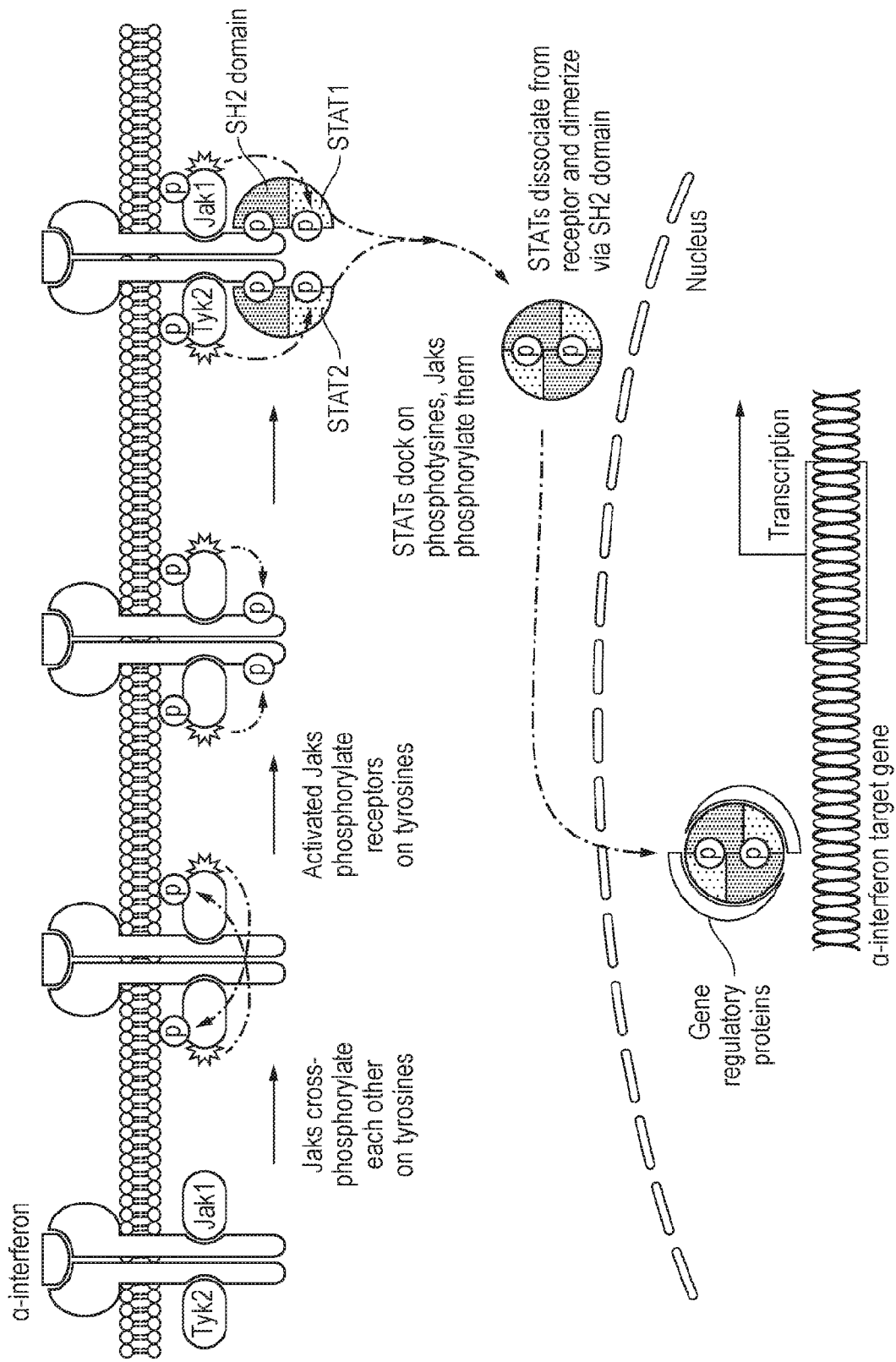

Signal Transducer and Activator of Transcription (STAT) molecules are a family of transcription factors that are involved in cytokine-mediated signal transduction. STAT transcription factors are recruited to the cytoplasmic region of cell surface receptors and are activated via phosphorylation. Once activated, they dimerize to form an activated STAT molecule comprising a first polypeptide and a second polypeptide, and translocate into the cell nucleus where they influence gene expression. They play a role in regulating cell growth processes and cell differentiation. The JAK-STAT signalling pathway consists of three main components: (1) a receptor which penetrates the cell membrane (2) Janus kinase (JAK), which is bound to the receptor and (3) Signal Transducer and Activator of Transcription (STAT), which carries the signal into the nucleus and DNA (see FIG. 3).

It is possible to enhance engraftment and persistence of CAR-expressing cells by including in the cell a constitutively active or inducible active JAK or STAT molecule. International Patent Application No. PCT/GB2018/052583 describes various alternative arrangements for Constitutively active STAT molecules (FIG. 4 of International Patent Application No. PCT/GB2018/052583) and inducible STAT molecules (FIG. 5 of International Patent Application No. PCT/GB2018/052583).

As described in International Patent Application No. PCT/GB2018/052583, a constitutively active JAK molecule may be made by expressing two JAK polypeptides which spontaneously dimerise or are linked by a linker, as described below for constitutively active STAT molecules. Alternatively, constitutively active JAK may be expressed which comprises a gain-of-function mutation.

The activity modulator may be a constitutively active or an inducible Signal Transducer and Activator of Transcription (STAT) molecule.

The STAT molecule of the cell may a first STAT polypeptide comprising a first dimerizing domain (DD) and a second STAT polypeptide comprising a second DD, which binds to the first DD.

The first and second DDs of the STAT molecule of the cell may, for example, comprise leucine zipper domains; or a heavy chain constant region and a light chain constant region.

An inducible STAT molecule of the cell may be inducibly active in the presence of an agent which causes dimerization of the first DD and second DD of the STAT molecule, thereby inducing activation of the STAT molecule. For example, the first DD may comprise FRB, the second DD may comprise FKBP12 and the agent may be rapamycin.

Alternatively, the STAT molecule of the cell may be inducibly inactive in the presence of an agent which causes dissociation of the first DD and second DD of the STAT molecule, thereby inducing non-activation of the STAT molecule. The first DD may comprise TetRB and the second DD may comprise TiP and the agent may be tetracycline, doxycycline or minocycline.

A constitutively active STAT may comprise a Gain of Function (GOF) mutation or may comprise a first STAT polypeptide and a second STAT polypeptide linked by a linker sequence.

The cell may comprise a membrane-tethering molecule comprising a tethering domain and a first binding domain (BD), and a constitutively active STAT molecule which comprises a second BD which binds specifically to the first BD. Binding of the first and second BD may be disrupted by the presence of an agent, such that in the presence of the agent the constitutively active STAT molecule dissociates from the membrane-tethering molecule, so that the constitutively active STAT molecule is free to translocate to the nucleus.

The first and second DD of the STAT molecule of the cell; or the first BD of the membrane-tethering molecule of the cell and second BD of the STAT molecule of the cell may comprise a Tet Repressor Protein (TetR) and a Transcription Inducing Peptide (TiP), respectively; and the agent may be tetracycline, doxycycline or minocycline.

The cell may comprise a) a CAR and a constitutively active STAT molecule joined by a STAT release domain and b) a STAT release molecule which releases the constitutively active STAT molecule from the CAR at the STAT release domain only upon recognition of a target antigen specific to the CAR, such that upon release, the constitutively active STAT molecule is free to translocate to the nucleus.

The STAT release molecule may comprise a CAR targeting domain, for example which binds to a phosphorylated immunoreceptors tyrosine based activation motif (ITAM). For example, the CAR targeting domain may comprise one or more ZAP70 SH2 domains.

The STAT release domain of the cell of the present invention may comprise a protease cleavage site, and the STAT release molecule of the cell may comprise a protease domain, such that upon recognition of a target antigen of the CAR, the protease domain cleaves at the protease cleavage site, releasing the STAT molecule.

4. Adhesion Molecule

Cell adhesion molecules (CAMs) are proteins located on the cell surface involved in binding with other cells or with the extracellular matrix (ECM) in cell adhesion.

These proteins are typically transmembrane receptors and are composed of three domains: an intracellular domain that interacts with the cytoskeleton, a transmembrane domain, and an extracellular domain that interacts either with other CAMs of the same kind (homophilic binding) or with other CAMs or the extracellular matrix (heterophilic binding).

Most CAMs belong to four protein families: Ig (immunoglobulin) superfamily (IgSF CAMs), the integrins, the cadherins, and the selectins.

The activity modulator of the present invention may be or comprise an adhesion molecule which modulates CAR- or TCR-expressing cell activity.

5. Transcription Factor

The agent of the invention may be or comprise a transcription factor which modulates activity of the CAR- or TCR-expressing cell.

A transcription factor is a protein which controls the rate of transcription of genetic information from DNA to messenger RNA, by binding to a specific DNA sequence and regulate the expression of a gene which comprises or is adjacent to that sequence.

Transcription factors work by promoting (as an activator), or blocking (as a repressor) the recruitment of RNA polymerase.

Transcription factors contain at least one DNA-binding domain (DBD), which attaches to either an enhancer or promoter region of DNA. Depending on the transcription factor, the transcription of the adjacent gene is either up- or down-regulated. Transcription factors also contain a trans-activating domain (TAD), which has binding sites for other proteins such as transcription coregulators.

Transcription factors use a variety of mechanisms for the regulation of gene expression, including stabilizing or blocking the binding of RNA polymerase to DNA, or catalyzing the acetylation or deacetylation of histone proteins. The transcription factor may have histone acetyltransferase (HAT) activity, which acetylates histone proteins, weakening the association of DNA with histones and making the DNA more accessible to transcription, thereby up-regulating transcription. Alternatively the transcription factor may have histone deacetylase (HDAC) activity, which deacetylates histone proteins, strengthening the association of DNA with histones and making the DNA less accessible to transcription, thereby down-regulating transcription. Another mechanism by which they may function is by recruiting coactivator or corepressor proteins to the transcription factor DNA complex.

The transcription may be constitutively active or conditionally active, i.e. requiring activation.

The transcription factor may be naturally occurring or artificial.

5.1 Transcriptional Reprogramming

In order for a CAR-T cell to be effective, it is important that it persists and expands in vivo and resists overly rapid differentiation and exhaustion. CAR T-cell persistence and engraftment is related to the proportion of naïve, central memory and T-stem-cell memory T-cells administered.

WO2018/115865 describes a cell which co-expresses a chimeric antigen receptor (CAR) and a transcription factor. Expression of the transcription factor may prevent or reduce differentiation and/or exhaustion of the cell in vitro and/or in vivo. By co-expressing the CAR with a transcription factor in a cell, it is possible to prevent or reduce differentiation and/or exhaustion of the cell. This results in a greater proportion of naïve, central memory and stem-cell memory cells in the cell composition for immunotherapy, and more effective persistence and expansion of the cells in vivo.

The activity modulator of the present invention may be a transcription factor. The transcription factor may prevent or reduce differentiation and/or exhaustion of the cell.

The transcription factor may be an effector memory repressor, such as BLIMP-1

Alternatively, the transcription factor may be a central memory repressor such as BCL6 or Bach2.

The transcription factor may be or comprise Bach2 or a modified version of Bach2 which has reduced or removed capacity to be phosphorylated by ALK. For example, modified Bach2 may comprise a mutation at one or more of the following positions: Ser-535, Ser-509, Ser-520.

The transcription factor may be FOXO1, EOMES, Runx3 or CBF beta.

6. Modulating TGFβ Signalling

Engineered cells face hostile microenvironments which limit adoptive immunotherapy. One of the main inhibitory mechanisms within the tumour microenvironment is transforming growth factor beta (TGFβ). The TGFβ signalling pathway has a pivotal role in the regulatory signalling that controls a variety of cellular processes. TGFβ play also a central role in T cell homeostasis and control of cellular function. Particularly, TGFβ signalling is linked to an immuno-depressed state of the T-cells, with reduced proliferation and activation. TGFβ expression is associated with the immunosuppressive microenvironment of tumour.

A variety of cancerous tumour cells are known to produce TGFβ directly. In addition to the TGFβ production by cancerous cells, TGFβ can be produced by the wide variety of non-cancerous cells present at the tumour site such as tumour-associated T cells, natural killer (NK) cells, macrophages, epithelial cells and stromal cells.

The transforming growth factor beta receptors are a superfamily of serine/threonine kinase receptors. These receptors bind members of the TGFβ superfamily of growth factor and cytokine signalling proteins. There are five type II receptors (which are activatory receptors) and seven type I receptors (which are signalling propagating receptors).

Auxiliary co-receptors (also known as type III receptors) also exist. Each subfamily of the TGFβ superfamily of ligands binds to type I and type II receptors.

The three transforming growth factors have many activities. TGFβ1 and 2 are implicated in cancer, where they may stimulate the cancer stem cell, increase fibrosis/desmoplastic reactions and suppress immune recognition of the tumour.

TGFβ1, 2 and 3 signal via binding to receptors TβRII and then association to TβRI and in the case of TGFβ2 also to TβRIII. This leads to subsequent signalling through SMADs via TβRI.

TGFβ s are typically secreted in the pre-pro-form. The "pre" is the N-terminal signal peptide which is cleaved off upon entry into the endoplasmic reticulum (ER). The "pro" is cleaved in the ER but remains covalently linked and forms a cage around the TGFβ called the Latency Associated Peptide (LAP). The cage opens in response to various proteases including thrombin and metalloproteases amongst others. The C-terminal region becomes the mature TGFβ molecule following its release from the pro-region by proteolytic cleavage. The mature TGFβ protein dimerizes to produce an active homodimer.

The TGFβ homodimer interacts with a LAP derived form the N-terminal region of the TGFβ gene product, forming a complex called Small Latent Complex (SLC). This complex remains in the cell until it is bound by another protein, an extracellular matrix (ECM) protein called Latent TGFβ binding protein (LTBP) which together forms a complex called the large latent complex (LLC). LLC is secreted to the ECM. TGFβ is released from this complex to a biologically active form by several classes of proteases including metalloproteases and thrombin.

The activity modulator of the present invention may modulate TGFβ signalling.

For example, the activity modulator may block or reduce TGFβ binding to TGFβ receptor; it may compete with TGFβ or TGFβR for binding to TGFβR or TGFβ; alternatively it may modulate the downstream TGFβ signalling for example via SMADs.

The activity modulator may be an agent such an antibody which binds TGFβ or TGFβ receptor.

Fresolimumab is a immunomodulatory antibody which blocks TGFβ1-3. Fresolimumab has been tested in metastatic melanoma and high-grade glioma. This showed some effectiveness in the enhancement of a tumour-specific immune response but failed to eradicate the tumour. Other antibodies which bind TGFβ include Lerdelimumab and Metelimumab.

Bedinger et al (2016) describes various human monoclonal antibodies that neutralize multiple TGFβ isoforms (MAbs 8(2): 389-404)

Alternatively the activity modulator may be a recombinant Fc-fusion proteins containing the soluble ectodomain of either TβRII (T(βRII-Fc) or the type III receptor, betaglycan. Soluble TβRII and soluble TβRIII (βglycan) function as decoy receptors preventing binding of TGF-6.

6.1 Dominant Negative TGFβ

The activity modulator may be a secreted factor which is capable of binding a transforming growth factor beta receptor (TβR) and disrupting its interaction with transforming growth factor beta (TGFβ).

The activity modulator may be a dominant negative TGFβ.

"Dominant negative TGFβ" or dnTGFβ as used herein means that the secreted factor TGFβ acts antagonistically to the wild-type TGFβ.

The dominant negative TGFβ inhibits signalling induced by wild-type TGFβ and thus neutralise its biological effects.

The activity modulator may be a mutant TGFβ.

The mature protein of wild-type TGFβ2 is shown below as in SEQ ID NO: 44.

```
                                        (SEQ ID NO: 44)
ALDAAYCFRNVQDNCCLRPLYIDFKRDLGWKWIHEPKGYNANFCAGACPY

LWSSDTQHSRVLSLYNTINPEASASPCCVSQDLEPLTILYYIGKTPKIEQ

LSNMIVKSCKCS.
```

A mutant TGFβ may comprise one or more mutations at amino acid residues W30, W32, L101, L51, Q67 and Y6 when the amino acid number is determined by alignment with SEQ ID NO: 44 and wherein:

amino acid residue 30 is mutated to N, R, K, D, Q, L, S, P, V, I, G, C, T, A or E; and/or amino acid residue 32 is mutated to A; and/or amino acid residue 101 is mutated to A, E; and/or amino acid residue 51 is mutated to Q, W, Y, A; and/or amino acid residue 67 is mutated to H, F, Y, W, Y; and/or amino acid residue 6 is mutated to A or a variant thereof.

Alternatively the activity modulator may comprise a truncated TGFβ polypeptide such as monomeric TGFβ. Kim et al (2017) describe an engineered TGFβ monomer that functions as a dominant negative to block TGFβ signalling (J. Biol. Chem. doi: 10.1074/jbc.M116.768754).

Truncated TGFβ may lack the heel helix α3, a structural motif essential for binding the TGFβ type I receptor (TβRI) but dispensable for binding TβRII.

The amino acid sequence of a TGFβ monomer is set forth in SEQ ID NO: 45. SEQ ID NO: 45 comprises a signal peptide and a latency associated peptide (LAP).

(SEQ ID NO: 45)
MHYCVLSAFLILHLVTVALSLSTCSTLDMDQFMRKRIEAIRGQILSKLKL

TSPPEDYPEPEEVPPEVISIYNSTRDLLQEKASRRAAACERERSDEEYYA

KEVYKIDMPPFFPSENAIPPTFYRPYFRIVRFDVSAMEKNASNLVKAEFR

VFRLQNPKARVPEQRIELYQILKSKDLTSPTQRYIDSKVVKTRAEGEWLS

FDVTDAVHEWLHHKDRNLGFKISLHCPCCTFVPSNNYIIPNKSEELEARF

AGIDGTSTYTSGDQKTIKSTRKKNSGKTPHLLLMLLPSYRLESQQTNRRK

KRALDAAYCFRNVQDNCCLRPLYIDFRKDLGWKWIHEPKGYNANFCAGAC

PYRASKSPSCVSQDLEPLTIVYYVGRKPKVEQLSNMIVKSCKCS.

The activity modulator may have an amino acid sequence set forth in SEQ ID NO: 45 or a variant thereof. The variant TGFβ monomer may have at least 80%, 85%, 90%, 95%, 98% or 99% sequence identity to SEQ ID NO: 45, provided that the polypeptide provides a monomer which is capable of binding a transforming growth factor beta receptor (TβR) and disrupting its interaction with transforming growth factor beta (TGFβ).

6.2 Dominant Negative TGFβ Receptor

The active TGFβ receptor (TβR) is a hetero-tetramer, composed by two TGFβ receptor I (TβRI) and two TGFβ receptor II (TβRII). TGFβ1 is secreted in a latent form and is activated by multiple mechanisms. Once activated it forms a complex with the TβRII TβRI that phosphorylates and activates WI.

The activity modulator may be a dominant negative TGFβ receptor. A dominant negative TGFβ receptor may lack the kinase domain.

For example, the activity modulator may comprise or consist of the sequence shown as SEQ ID No. 46, which is a monomeric version of TGF receptor II (dn TGFβ RII)
SEQ ID No. 46
TIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDLLLVIFQVTGISL

LPPLGVAISVIIIFYCYRVNRQQKLSS

A dominant-negative TGF-81:111 (dnTGF-βRIII) has been reported to enhance PSMA targeted CAR-T cell proliferation, cytokine secretion, resistance to exhaustion, long-term in vivo persistence, and the induction of tumour eradication in aggressive human prostate cancer mouse models (Kloss et al (2018) Mol. Ther. 26:1855-1866).

6.3 SMADs

As mentioned above, the active TGFβ receptor (TβR) is a hetero-tetramer, composed by two TGFβ receptor I (TβRI) and two TGFβ receptor II (TβRII). Signaling is initiated when activated TGF-β binds to transforming growth factor-β receptor-2 (TβRII) with high affinity. This binding requires the participation of the transforming growth factor-8 receptor-3 (TβRIII), also known as βglycan, which causes a conformational change in TβRII that facilitates ligand-receptor binding TGF-β receptor-1/ALK-5 (TβRI), a serine/threonine kinase, is then recruited to the TGF-β/TβRII complex and initiates signaling by phosphorylating SMAD2 and SMAD3, which belong to the receptor-regulated family of SMAD proteins. Phosphorylated SMAD2 and SMAD3 combine to form a heteromeric complex with SMAD4 that translocates to the cell nucleus to interact with various transcriptional factors that ultimately leads to the cellular response SMAD proteins are intracellular transcription factors for conveying extracellular signal from membrane to the nucleus upon the activation of TGFβ. Three types of SMAD have been identified: a receptor-regulated SMAD s (R-SMAD) including SMAD2 and SMAD3 and a common-mediator SMAD (co-SMAD) including SMAD4 only. Finally, an inhibitory SMAD s (I-SMAD) including SMAD6 and SMAD7.

SMAD proteins consist of two globular domains connected by a linker region. The main function of the SMAD N-terminal domain, or "Mad homology 1" (MH1) domain, is to bind DNA. The C-terminal domain, or MH2 domain, mediates protein-protein interaction with numerous regulator and effector proteins, including the TβR receptors, certain cytoplasmic anchor proteins, lineage-specific DNA-binding cofactors, and chromatin modifiers. In the presence of TGFβ, R-SMAD is phosphorylated by TGFβ receptor. This phosphorylation targets two serine residues in the SMAD C terminus sequence, pSer-X-pSer, creating an acidic tail that drives the formation of SMAD transcriptional complexes. Missense mutation of two conserved amino acid in the N terminal portion of the MH2 domain has been identified in patient with colorectal cancer. These two mutations cause the acquisition of a dominant negative behaviour that counteract the activity of the WT SMAD protein.

The activity modulator may be a SMAD signalling inhibitors such as Galunisertib which has been tested as a monotherapy or in combination with alkylating agents, Lomustine or temozolamide for glioblastoma and other combinations.

Alternatively the activity modulator may be a dominant negative version of the signal transduced SMAD2 and SMAD3 and SMAD4 expressing only the MH2 domain. The activity modulator may be: i) MH2, ii) MH2 truncated, missing the last 24 aa and iii) truncated SMAD2_MH2-linker-SMAD3_MH2. These dominant negatives compete with the wild type SMAD protein for the receptor-docking domains and for the binding with partner proteins thus reducing or blocking TGFβ signalling.

A dnSMAD may be selected from one or more of SMAD2, SMAD3 and or SMAD4. The dnSMAD lacks a functional MH1 domain.

The MH1 domain is a conserved MAD homology domain of at the N terminus of a SMAD protein. The MH1 domain is capable of DNA binding and negatively regulates the functions of the MH2 domain.

The MH2 domain is a conserved MAD homology domain of at the C terminus of a SMAD protein. The MH2 domain contain a central β-sandwich with a conserved loop-helix is capable of binding phospho-serine residues. The MH2 domain mediates protein: protein interactions with regulator and effector proteins, including the TβR receptors, cytoplasmic anchor proteins, lineage-specific DNA-binding cofactor and chromatin modifiers.

The activity modulator may comprise or consist essentially of or consists of a wild-type MH2 domain from SMAD2, SMAD3 and SMAD4. The amino acids sequences for these MH2 domains are shown below as SEQ ID Nos 47 to 49.

(SEQ ID NO: 47-MH2 domain of SMAD2)
WCSIAYYELNQRVGETFHASQPSLTVDGFTDPSNSERFCLGLLSNVNRNA

TVEMTRRHIGRGVRLYYIGGEVFAECLSDSAIFVQSPNCNQRYGWHPATV

CKIPPGCNLKIFNNQEFAALLAQSVNQGFEAVYQLTRMCTIRMSFVKGWG

AEYRRQTVTSTPCWIELHLNGPLQWLDKVLTQMGSPSVRCSSMS (SEQ ID NO: 48-MH2 domain of SMAD3)
WCSISYYELNQRVGETFHASQPSMTVDGFTDPSNSERFCLGLLSNVNRNA

AVELTRRHIGRGVRLYYIGGEVFAECLSDSAIFVQSPNCNQRYGWHPATV

CKIPPGCNLKIFNNQEFAALLAQSVNQGFEAVYQLTRMCTIRMSFVKGWG

AEYRRQTVTSTPCWIELHLNGPLQWLDKVLTQMGSPSIRCSSVS (SEQ ID NO: 49-MH2 domain of SMAD4)
WCSIAYFEMDVQVGETFKVPSSCPIVTVDGYVDPSGGDRFCLGQLSNVHR

TEAIERARLHIGKGVQLECKGEGDVWVRCLSDHAVFVQSYYLDREAGRAP

GDAVHKIYPSAYIKVFDLRQCHRQMQQQAATAQAAAAAQAAAVAGNIPGP

GSVGGIAPAISLSAAAGIGVDDLRRLCILRMSFVKGWGPDYPRQSIKETP

CWIEIHLHRALQLLDEVLHTMPIADPQPL

The activity modulator may comprise or consist essentially of a truncated version of one of the MH2 domains outlined above, with a deletion of up to 24 amino acids from the C terminus of the wild type MH2 domain.

The activity modulator may comprises a mutation in the MH2 domain which increases the binding affinity of the dnSMAD for a phosphorylated TGFβ receptor. The activity modulator may consists essentially of or consists of: a MH2 domain of a SMAD4 polypeptide comprising a mutation R497H, K5070 and/or R515G where the amino acid numbering corresponds to the numbering set forth in SEQ ID NO: 49; an MH2 domain of SMAD3 comprising a mutation K378R and/or K314R where the amino acid numbering corresponds to the numbering set forth in SEQ ID NO:48.

The activity modulator may be a chimeric dnSMAD which comprises at least two dnSMAD polypeptides as defined above. The dnSMAD polypeptides of the chimeric dnSMAD may be connected by a linker domain.

The amino acid sequence of a chimeric dnSMAD comprising a dnSMAD2 polypeptide and a dnSMAD3 polypeptide is shown below as SEQ ID No. 50.

(SEQ ID NO: 50)
WCSIAYYELNQRVGETFHASQPSLTVDGFTDPSNSERFCLGLLSNVNRNA

TVEMTRRHIGRGVRLYYIGGEVFAECLSDSAIFVQSPNCNQRYGWHPATV

CKIPPGCNLKIFNNQEFAALLAQSVNQGFEAVYQLTRMCTIRMSFVKGWG

AEYRRQTVTSTPCWIELHLNGPLQWLDKVLTQMLEYSGGGSGGGSLEWCS

ISYYELNQRVGETFHASQPSMTVDGFTDPSNSERFCLGLLSNVNRNAAVE

LTRRHIGRGVRLYYIGGEVFAECLSDSAIFVQSPNCNQRYGWHPATVCKI

PPGCNLKIFNNQEFAALLAQSVNQGFEAVYQLTRMCTIRMSFVKGWGAEY

RRQTVTSTPCWIELHLNGPLQWLDKVLTQM

A dnSMAD or chimeric dnSMAD may comprise a sequence shown as: SEQ ID NO: 47 to 50; or a variant having at least 80% (preferably at least 85%, at least 90%, at least 95%, at least 97%, or at least 99%) sequence identity to SEQ ID NO: 47 to 50 provided that the variant sequence retains the capacity to compete with the wild type SMAD protein for the receptor-docking domains and for the binding with partner proteins and reduces or blocks TGFβ signalling.

7. Metabolic Enzymes

The activity modulator may be a metabolic enzyme such as AMP-activated protein kinase (AMPK) or Isocitrate dehydrogenase (IDH)

AMPK plays a role in cellular energy homeostasis, largely to activate glucose and fatty acid uptake and oxidation when cellular energy is low.

AMPK is a heterotrimeric protein complex formed by α, β, and γ subunits. Each of these three subunits takes on a specific role in both the stability and activity of AMPK. Specifically, the γ subunit includes four particular Cystathionine beta synthase (CBS) domains giving AMPK its ability to sensitively detect shifts in the AMP:ATP ratio. The four CBS domains create two binding sites for AMP commonly referred to as Bateman domains. Binding of one AMP to a Bateman domain cooperatively increases the binding affinity of the second AMP to the other Bateman domain. As AMP binds both Bateman domains the γ subunit undergoes a conformational change which exposes the catalytic domain found on the a subunit. It is in this catalytic domain where AMPK becomes activated when phosphorylation takes place at threonine-172 by an upstream AMPK kinase (AMPKK). The α, β, and γ subunits can also be found in different isoforms: the γ subunit can exist as either the γ1, γ2 or γ3 isoform; the β3 subunit can exist as either the β1 or β2 isoform; and the a subunit can exist as either the α1 or α2 isoform.

The following human genes encode AMPK subunits:
α—PRKAA1, PRKAA2
β—PRKAB1, PRKAB2
γ—PRKAG1, PRKAG2, PRKAG3

The activity modulator may comprise one or more AMPK subunits. The activity modulator may comprise α, β, and γ subunits from AMPK.

IDH catalyzes the oxidative decarboxylation of isocitrate, producing alpha-ketoglutarate (α-ketoglutarate) and $CO_2$. This is a two-step process, which involves oxidation of isocitrate (a secondary alcohol) to oxalosuccinate (a ketone), followed by the decarboxylation of the carboxyl group beta to the ketone, forming alpha-ketoglutarate. In humans, IDH exists in three isoforms: IDH3 catalyzes the third step of the citric acid cycle while converting NAD+ to NADH in the mitochondria. The isoforms IDH1 and IDH2 catalyze the same reaction outside the context of the citric acid cycle and use NADP+ as a cofactor instead of NAD+. They localize to the cytosol as well as the mitochondrion and peroxisome.

The activity modulator may IHD1, IHD2 or IHD3. The amino acid sequences for human IDH1, 2 and 3 are on the NCBI database with the following accession numbers: CAG38738.1 (IDH1); NP_002159.2 (IDH2, isoform 1); NP_001276839.1 (IDH2, isoform 2); NP_001277043.1 (IDH2, isoform 3); NP_689996.4 (IDH3, isoform 1); NP_001274178.1 (IDH3, isoform 2); NP_001339753.1 (IDH3, isoform 3).

8. Co-Stimulatory Signals

The activity modulator of the present invention may provide co-stimulatory signal to the T-cell.

For example, the activity modulatory may be a TNF receptor, a chimeric TNF receptor or a TNF receptor ligand.

TNF-family co-stimulatory molecules provide survival and expansion signals for T-cells during their ontogeny. These TNF receptors (TNFRs) signal via TNF receptor associated factor (TRAF) second messengers.

TNFRSF9 (4-1BB), TNFRSF4 (OX40), TNFRSF5 (CD40) and TNFRSF14 (GITR) transmit survival signals to T-cells. TNFRSF7 (CD27) and TNFRSF14 (HVEM) are expressed by naïve T-cells. The expression of OX40 and 4-1 BB is induced in response to antigen stimulation, these TNFRs have been proposed to be markers of effector T cells. Although CD27 and GITR can be constitutively expressed by conventional T cells, their expression is also strongly upregulated following T-cell activation, possibly in parallel with the upregulation of OX40 and 4-1 BB expression.

The induction or upregulation of OX40, 4-1 BB and GITR expression occurs within 24 hours following the recognition of antigen by and activation of naive T cells, and much more rapidly by memory T cells; the expression of these receptors can last for several hours or even days.

The TNF receptor TNFRSF35/Death receptor 3 (D3R) is activated by TL1A which is upregulated by inflamed tissue transiently and this interaction appears to be important for the late stage of T-cell activity after an established immune response.

CD40 is not expressed by T-cells, but CD40L is and CD40/CD40L is particularly important for B-cell differentiation and expansion.

TNFRSF11A (RANK) is not expressed by T-cells, but the RANK/RANK-L pathway is important to immune development as well as being a key pathway for osteoclast activity and is active during bone metastasis.

TNFRSF12A (Fn14) is not expressed by T-cells, but is expressed along with its ligand TWEAK in damaged or inflamed tissues and most cancers.

8.1 Chimeric TNF Receptors

International Patent Application No. PCT/GB2018/053629 describes chimeric TNF receptors which comprise (a) a binding domain which is capable of binding a TNFR ligand; and (b) a TNFR signalling domain.

The presence of a chimeric TNFR enables the tight temporal and/or spatial control of TNFR signalling to be decoupled in order to provide improved survival signals for engineered cells, for example CAR T cells. The chimeric TNFR may compensate for the lack of a complete physiological immune response in a tumour microenvironment. The chimeric TNFR may be constructed such that the antigen-binding domain is engaged, and thus a required co-stimulatory signal induced, in the tumour microenvironment.

The antigen-binding domain of the chimeric TNFR may comprise the ligand binding domain of a TNFR. For example, the antigen-binding domain may comprise the ligand binding domain of D3R, HVEM, CD27, CD40, RANK or Fn14.

The signalling domain of the chimeric TNFR may be an activating signalling domain, such as one which is capable of signalling via TNFR-associated factors (TRAFs). For example, the activating signalling domain may comprise the signalling portion of the 4-1 BB, OX40, or GITR endodomain.

The activity modulator may be a HVEM-41BB chimera, a CD27-41BB chimera, a RANK-41BB chimera or an Fn14-41BB chimera. Examples of suitable amino acid sequences for these chimeric TNF receptors are shown below as SEQ ID No. 51 to 54, in which the ectodomain is shown in normal text, the transmembrane domain in bold and the 41 BB endodomain in italics.

(HVEM-41BB)
SEQ ID No. 51
MEPPGDWGPPPWRSTPRTDVLRLVLYLTFLGAPCYAPALPSCKEDEYPVG

SECCPKCSPGYRVKEACGELTGTVCEPCPPGTYIAHLNGLSKCLQCQMCD

PAMGLRASRNCSRTENAVCGCSPGHFCIVQDGDHCAACRAYATSSPGQRV

QKGGTESQDTLCQNCPPGTFSPNGTLEECQHQTKCSWLVTKAGAGTSSSH

WVIISFFLALTSTALLFLLFFLTLRFSVVKRGRKKLLYIFKQPFMRPVQT

TQEEDGCSCRFPEEEEGGCEL (CD27-41BB)
SEQ ID No. 52
MARPHPWWLCVLGTLVGLSATPAPKSCPERHYWAQGKLCCQMCEPGTFLV

KDCDQHRKAAQCDPCIPGVSFSPDHHTRPHCESCRHCNSGLLVRNCTITA

NAECACRNGWQCRDKECTECDPLPNPSLTARSSQALSPHPQPTHLPYVSE

MLEARTAGHMQTLADFRQLPARTLSTHWPPQRSLCSSDFIRIISFFLALT

STALLFLLFFLTLRFSVVKRGRKKLLYIFKQPFMRPVQTTQEEDGCSCRF

PEEEEGGCEL (RANK-41BB)
SEQ ID No. 53
MAPRARRRRPLFALLLLCALLARLQVALQIAPPCTSEKHYEHLGRCCNKC

EPGKYMSSKCTTTSDSVCLPCGPDEYLDSWNEEDKCLLHKVCDTGKALVA

VVAGNSTTPRRCACTAGYHWSQDCECCRRNTECAPGLGAQHPLQLNKDTV

CKPCLAGYFSDAFSSTDKCRPWTNCTFLGKRVEHHGTEKSDAVCSSSLPA

RKPPNEPHVYLPIISFFLALTSTALLFLLFFLTLRFSVVKRGRKKLLYIF

KQPFMRPVQTTQEEDGCSCRFPEEEEGGCEL (Fn14-41BB)
SEQ ID No. 54
MARGSLRRLLRLLVLGLWLALLRSVAGEQAPGTAPCSRGSSWSADLDKCM

DCASCRARPHSDFCLGCAAAPPAPFRLLWPIISFFLALTSTALLFLLFFL

TLRFSVVKRGRKKLLYIFKQPFMRPVQTTQEEDGCSCRFPEEEEGGCEL 8.2 TNF Receptor Ligands

The TNF-related cytokines (TNF family ligands) are type II transmembrane proteins (intracellular N-terminus) with a short cytoplasmic tail (15 to 25 residues in length) and a larger extracellular region (~50 amino acids) containing the signature TNF homology domain where the receptor binding sites are located.

A summary of TNFRs and their ligands is provided in Table 3.

TABLE 3

| Protein (member #) | Synonyms | Gene | Ligand(s) |
|---|---|---|---|
| Tumor necrosis factor receptor 1 | CD120a | TNFRSF1A | TNF-alpha (cachectin) |
| Tumor necrosis factor receptor 2 | CD120b | TNFRSF1B | TNF-alpha (cachectin) |
| Lymphotoxin beta receptor | CD18 | LTBR | Lymphotoxin beta (TNF-C) |
| OX40 | CD134 | TNFRSF4 | OX40L |
| CD40 | Bp50 | CD40 | CD154 |
| Fas receptor | Apo-1, CD95 | FAS | FasL |
| Decoy receptor 3 | TR6, M68 | TNFRSF6B | FasL, LIGHT, TL1A |
| CD27 | S152, Tp55 | CD27 | CD70, Siva |
| CD30 | Ki-1 | TNFRSF8 | CD153 |
| 4-1BB | CD137 | TNFRSF9 | 4-1BB ligand |

TABLE 3-continued

| Protein (member #) | Synonyms | Gene | Ligand(s) |
|---|---|---|---|
| Death receptor 4 | TRAILR1, Apo-2, CD261 | TNFRSF10A | TRAIL |
| Death receptor 5 | TRAILR2, CD262 | TNFRSF10B | TRAIL |
| Decoy receptor 1 | TRAILR3, LIT, TRID, CD263 | TNFRSF10C | TRAIL |
| Decoy receptor 2 | TRAILR4, TRUNDD, CD264 | TNFRSF10D | TRAIL |
| RANK | CD265 | TNFRSF11A | RANKL |
| Osteoprotegerin | OCIF, TR1 | TNFRSF11B | |
| TWEAK receptor | Fn14, CD266 | TNFRSF12A | TWEAK |
| TACI | IGAD2, CD267 | TNFRSF13B | APRIL, BAFF, CAMLG |
| BAFF receptor | CD268 | TNFRSF13C | BAFF |
| Herpesvirus entry mediator | ATAR, TR2, CD270 | TNFRSF14 | LIGHT |
| Nerve growth factor receptor | p75NTR, CD271 | NGFR | NGF, BDNF, NT-3, NT-4 |
| B-cell maturation antigen | TNFRSF13A, CD269 | TNFRSF17 | BAFF |
| Glucocorticoid-induced TNFR-related | AITR, CD357 | TNFRSF18 | GITR ligand |
| TROY | TAJ, TRADE | TNFRSF19 | unknown |
| Death receptor 6 | CD358 | TNFRSF21 | |
| Death receptor 3 | Apo-3, TRAMP, LARD, WS-1 | TNFRSF25 | TL1A |
| Ectodysplasin A2 receptor | XEDAR | EDA2R | EDA-A2 |

The activity modulator may be or comprise a TNF receptor ligand such as CD40L (CD154), OX40L (CD134) or 41BBL. The amino acid sequences for these proteins are shown below as SEQ ID No. 55 to 57

```
(CD40L)
                                          SEQ ID No. 55
MIETYNQTSPRSAATGLPISMKIFMYLLTVFLITQMIGSALFAVYLHRRL

DKIEDERNLHEDFVFMKTIQRCNTGERSLSLLNCEEIKSQFEGFVKDIML

NKEETKKENSFEMQKGDQNPQIAAHVISEASSKTTSVLQWAEKGYYTMSN

NLVTLENGKQLTVKRQGLYYIYAQVTFCSNREASSQAPFIASLCLKSPGR

FERILLRAANTHSSAKPCGQQSIHLGGVFELQPGASVFVNVTDPSQVSHG

TGFTSFGLLKL (OX40L)
                                          SEQ ID NO. 56
MERVQPLEENVGNAARPRFERNKLLLVASVIQGLGLLLCFTYICLHFSAL

QVSHRYPRIQSIKVQFTEYKKEKGFILTSQKEDEIMKVQNNSVIINCDGF

YLISLKGYFSQEVNISLHYQKDEEPLFQLKKVRSVNSLMVASLTYKDKVY

LNVTTDNTSLDDFHVNGGELILIHQNPGEFCVL (41BBL)
                                          SEQ ID NO. 57
MEYASDASLDPEAPWPPAPRARACRVLPWALVAGLLLLLLLAAACAVFLA

CPWAVSGARASPGSAASPRLREGPELSPDDPAGLLDLRQGMFAQLVAQNV

LLIDGPLSWYSDPGLAGVSLTGGLSYKEDTKELVVAKAGVYYVFFQLELR

RVVAGEGSGSVSLALHLQPLRSAAGAAALALTVDLPPASSEARNSAFGFQ

GRLLHLSAGQRLGVHLHTEARARHAWQLTQGATVLGLFRVTPEIPAGLPS

PRSE
```

Chimeric RTK

Receptor Protein-Tyrosine Kinase (RPTKs) constitute a family of intracellular signal regulators that mediate embryonic development, cell growth, metabolism, and immune function. RPTKs are often dysregulated in cancer, driving proliferation.

The proliferative capacity of CAR T-cells is inconsistent between different binders and structures, and the characteristics bestowing maximum proliferative incentive are elusive. CAR T-cells are exposed to the hostile tumour microenvironment, and incorporation of RPTK in a dimer format can provide a proliferative advantage to the CAR T-cells. Expression of an RTK which is capable of signalling in the absence of cognate ligand breaks the tumour immune-depriving milieu in order to improve the CAR T-cell survival signal.

RTKs signal through ligand-induced dimerization/oligomerisation, which leads to auto-phosphorylation of tyrosine residues in the kinase domain activation loop of their cytoplasmic tail. Ligand-mediated oligomerisation of the RTK leads to a two-step activation, the increase in catalytic activity and the creation of docking sites for downstream signalling proteins.

Typically RTKs homodimerize in order to signal.

The RTK auto-phosphorylation may occur in cis or in trans. The phosphorylated tyrosine residues constitute docking sites for numerous SH2-containing signalling molecules. Generally, all RTKs signal through common downstream signal protein such as: PI3 kinase, Ras-Raf-MAPK, JNK, and PLCγ. The signalling is mediated by the JAK-STAT pathway.

The activity modulator may be a receptor tyrosine kinase (RTK) which is capable of signalling in the absence of cognate ligand. Such RTK are described in GB patent application No. 1803079.1.

The RTK may be over-expressed and/or comprise a mutation such that it is capable of signaling in the absence of cognate ligand.

The RTK may be a chimeric RTK. The chimeric RTK may comprise an ectodomain or an endodomain which mediates dimerization or oligomerization of the chimeric RTK.

The domain which mediates dimerization or oligomerization of the chimeric RTK may comprise a disulphide bond, for example it may be or comprise a hinge domain.

Alternatively, the domain which mediates dimerization or oligomerization of the chimeric RTK may comprise a chemically operable dimerization or oligomerization domain. Dimerization or oligomerization of the chimeric RTK may inducible by an agent.

A summary of human RTK subfamilies and RTKs is shown in Table 4.

TABLE 4

| RTK Family | RTK | RTK Family | RTK | RTK Family | RTK |
|---|---|---|---|---|---|
| Epidermal growth factor receptor (EGFR) | EGFR | Fibroblast growth factor receptor (FGFR) | FGFR-1 | Related to receptor tyrosine kinase (RYK) | RYK |
| | ERBB2 | | FGFR-2 | Discoidin domain receptor family (DDR) | DDR1 |
| | ERBB3 | | FGFR-3 | | DDR2 |
| | ERBB4 | | FGFR-4 | RET | RET |
| Insulin Receptor | INSR | KLG/CCK | CCK4 | Leukocyte receptor tyrosine kinase (LTK) | LTK |
| | IGF-1R | Erythropoietin-producing human hepatocellular receptors (EPHR) | EPHA1 | | ALK |
| | IRR | | EPHA2 | Muscle-Specific Kinase (MUSK) | MUSK |
| Platelet derived growth factor receptor (PDGFR) | PDGFR-α | | EPHA3 | NGFR | TRKA |
| | PDGFR-β | | EPHA4 | | TRKB |
| | CSF-1R | | EPHA5 | | TRKC |
| | KIT/SCFR | | EPHA6 | Hepatocyte growth factor receptor (HGFR) | MET |
| | KLK2/FLT3 | | EPHA7 | | RON |
| Vascular endothelial growth factor receptor (VEGFR) | VEGFR1 | | EPHA8 | LMR | AATYK |
| | VEGFR2 | | EPHB1 | | AATYK2 |
| | VEGFR3 | | EPHB2 | | AATYK3 |
| TIE | TIE | | EPHB3 | Tyrosine-protein kinase receptor (AXL) | AXL |
| | TEK | | EPHB4 | | MER |
| Receptor tyrosine kinase-like orphan receptors (ROR) | ROR1 | | EPHB5 | | TYRO3 |
| | ROR2 | | EPHB6 | Unknown | RTK106 |
| ROS | ROS | | | | |

Illustrative UniProt Accession Numbers and associated amino acid sequences of the human RTKs shown in Table 2 are provided in Table 5.

TABLE 5

| RTK | UniProt Accession Number |
|---|---|
| EGFR | P00533 |
| ERBB2 | P04626 |
| ERBB3 | P21860 |
| ERBB4 | Q15303 |
| INSR | P06213 |
| IGF-1R | P08069 |
| IRR | P14616 |
| PDGFR-α | P16234 |
| PDGFR-β | P09619 |
| CSF-1R | P07333 |
| KIT/SCFR | P10721 |
| KLK2/FLT3 | P20151 |
| VEGFR1 | P17948 |
| VEGFR2 | P35968 |
| VEGFR3 | P35916 |
| TIE | P35590 |
| TEK | Q02763 |
| ROR1 | Q01973 |
| ROR2 | Q01974 |
| ROS | P08922 |
| FGFR-1 | P11362 |
| FGFR-2 | P21802 |
| FGFR-3 | P22607 |
| FGFR-4 | P22455 |
| CCK4 | Q13308 |
| EPHA1 | P21709 |
| EPHA2 | P29317 |
| EPHA3 | P29320 |
| EPHA4 | P54764 |
| EPHA5 | P54756 |
| EPHA6 | Q9UF33 |
| EPHA7 | Q15375 |
| EPHA8 | P29322 |
| EPHB1 | P54762 |
| EPHB2 | P29323 |
| EPHB3 | P54753 |
| EPHB4 | P54760 |
| EPHB5 | |
| EPHB6 | O15197 |
| RYK | P34925 |
| DDR1 | Q08345 |
| DDR2 | Q16832 |
| RET | P07949 |
| LTK | P29376 |
| ALK | Q9UM73 |
| MUSK | O15146 |
| TRKA | P04629 |
| TRKB | Q16620 |
| TRKC | Q16288 |
| MET | P08581 |
| RON | Q04912 |
| AATYK | Q6ZMQ8 |
| AATYK2 | Q8IWU2 |
| AATYK3 | Q5XJV6 |

TABLE 5-continued

| RTK | UniProt Accession Number |
| --- | --- |
| AXL | P30530 |
| MER | Q12866 |
| TYRO3 | Q06418 |
| RTK106 | |

Modulating Target Cell Activity

The activity modulator may modulate the activity of the target cell, for example, the tumour cell.

For example, the agent may be a toxin, such as a toxin which is toxic to tumour cells. For example, the agent may be diphtheria toxin, *pseudomonas* toxin or *shigella* toxin.

Alternatively the activity modulator may be a pro-drug or a pro-drug activating compound. The activity modulator may be a pro-drug activating enzyme.

Prodrugs are widely used in the targeted delivery of cytotoxic compounds to cancer cells. Prodrugs are inactive or less active derivatives of drug molecules which undergo enzymatic or chemical transformation to regenerate the active forms.

In targeted cancer therapy, conventional chemotherapeutic agents, which lack intrinsic target specificity, are rationally modified to focus and redirect their cytotoxicity to tumor cells. The usefulness of many conventional, nonspecific chemotherapeutic agents, such as doxorubicin, paclitaxel, camptothecan, cisplatin, and their derivatives have been significantly extended by modification into prodrugs, particularly those harboring cell-targeting moieties.

The activity modulator may be an enzyme which activates a specific inactive substrate (prodrug), which is administered separately, to a cytotoxic product. The activity modulator may be or comprise cytosine deaminase (CD) which converts the prodrug 5-fluorocytosine (5-FC) to 5-fluorouracil (5-FU), whose downstream antimetabolites lead to a so-called "thymineless death". Alternatively the activity modulator may be or comprise a cytosine deaminase/uracil phospho-ribosyltransferase fusion (CD/UPRT; encoded by the Fcy::Fur gene) which has also been used to generate the 5-FU-based antimetabolites. Other antimetabolite prodrugs include the nucleoside analogs such as acyclovir and ganciclovir, which are activated to their active triphosphate using recombinant thymidylate kinase, as well as 6-methyl-2'-deoxyriboside and 2-fluoro-2'-deoxyadenosine, which are converted by purine nucleoside phosphorylase to 6'-methylpurine and 2-fluoroadenine, respectively. Human deoxycytidine kinase (DCK) and thymidylate kinase (tmpk) are capable of mono-phosphorylating a range of (non-physiologic) prodrugs such as gemcitabine (dFdC), bromovinyl-deoxyuridine (BVdU), cytarabine (AraC), and 3'-azido-3'-deoxythymidine (AZT) monophosphate. A chimeric fusion of DCK with uridine monophosphate kinase (DCK::UMK) has also been developed to directly activate gemcitabine to its cytotoxic diphosphate metabolite (dFdCDP) in pancreatic carcinoma. There are also "designer" prodrugs in which a chemotherapeutic agent is derivatized to a substrate for a specific activating enzyme. Examples include phenoxyacetamide conjugates of doxorubicin and melphalan that are hydrolyzed by penicillin-V amidase, a dipiperidinyl conjugate of etoposide (VP-16) that is hydrolyzed by a recombinant carboxylesterase, and a cephalosporin conjugate of 5-FU designed for hydrolysis by β-lactamase.

The activity modulator may be an enzyme capable of cleaving a prodrug-conjugate for example, a pro-drug conjugate comprising a toxin. Like prodrug conjugates, many targeted toxins consist of a targeting moiety (e.g., an antibody, in the case of immunotoxins), a cleavable linker, and a drug (cytotoxic enzyme). Moxetumomab pasudotox, consists of a truncated exotoxin A from *Pseudomonas aeruginosa* in which the native receptor-binding domain (located in the N-terminal 250 residues) has been replaced with a single-chain variable fragment targeting the cell-surface CD22 antigen. Cytotoxic activity is conferred entirely by the C-terminal segment (residues 405 to 613, termed PE3). As is, this conjugate is an inactive toxin: cytotoxic activation requires cleavage by the protease furin during endocytosis between residues 279 and 280. Thus, moxetumomab pasudotox is functionally a targeted prodrug conjugate in which residues 251 to 364 from exotoxin A (domain II) serves as a linker whose cleavage releases the cytotoxic PE3.

1. Biosynthetic CAR T Cell

The activity modulator may be an enzyme which is capable of synthesising a small molecule when expressed or expressed in combination in a cell.

International patent application No. PCT/GB2018/053262 describes engineered cells which encode a transgenic synthetic biology pathway that enables the engineered cell to produce a small molecule, in particular a therapeutic small molecule. The engineered cell may comprises; (i) a chimeric antigen receptor (CAR) or a transgenic T-cell receptor (TCR); and (ii) one or more engineered polynucleotides which encode one or more enzymes which are capable of synthesising a therapeutic small molecule when expressed in combination in the cell.

There may be, for example one, two, three four or five enzymes. The one or more enzymes may be encoded in one or more open reading frames. The one or more enzymes may be encoded in a single open reading frame. Suitably, each enzyme may be separated by a cleavage site. The cleavage site may be a self-cleavage site, such as a sequence encoding a FMD-2A like peptide.

The therapeutic small molecule may, for example be a cytotoxic molecule; a cytostatic molecule; an agent which is capable of inducing differentiation of the tumour; or a proinflammatory molecule. In particular, the small molecule may be violacein or a derivative thereof, or geraniol.

Target Cell Microenvironment Modulating Agent

The activity modulator may be an agent which modulates the environment of the target cell, for example, the tumour cell.

For example, the agent may be a cytokine such as IL-7 or IL-12 or a chemokine such as CCL19 as discussed above. Alternatively, the agent may affect the expression or activity of a cytokine or chemokine as discussed above.

1. CAR-T Cell Secreting Enzymes

The immune microenvironment contains small molecule metabolites and nutrients which can alter the balance between the tumour survival and/or progression and an immune response. Modulation of the microenvironment may alter the balance in favour of the immune response and/or can improve the activity or efficacy of adaptive immune therapy, such as the efficacy of engineered cells expressing a CAR or transgenic TCR.

An activity modulatory in connection with the present invention may modulate the level of one or more metabolites or nutrients in the tumour microenvironment, skewing the balance in favour of immune cells such as T-cells involved in an immune response and/or away from tumour cells.

For example, the activity modulator be one or more enzymes which, when secreted or expressed at the cell surface, causes depletion of a molecule extracellular to the engineered cell which is:
 (i) required by a tumour cell for survival, proliferation, metastasis or chemoresistance, and/or
 (ii) detrimental to the survival, proliferation or activity of the engineered cell.

United Kingdom application No. 1820443.8 describes engineered cells which secrete such enzymes or express them at the cell surface.

The enzyme(s) may cause the depletion of an amino acid or amino acid metabolite, a nucleobase (such as a nucleoside or nucleotide) or a lipid.

Where the activity modulator causes the depletion of a nutrient or metabolite which is needed for tumour cell growth or survival, the immune cell (e.g. CAR-T cell) may be engineered to survive in the absence of the molecule in the extracellular environment. For example, the cell may be engineered to synthesise the molecule or a precursor thereof intracellularly.

Cell Composition

The present invention also provides a cell composition made by the method of the present invention.

The invention provides cell composition made by transduction of cells with a plurality of viral vectors such that the composition comprises a mixture of untransduced cells, singly transduced cells and combinatorially transduced cells.

At least one vector in the mixture of viral vectors used in the method of the present invention comprises a nucleic acid sequence encoding a CAR. The cell composition may therefore comprise a mixture of singly and combinatorially transduced CAR-expressing cells.

"Combinatorially transduced" means that the cell is transduced with at least two viral vectors. For example, if cells are transduced with two vectors, one comprising transgene A and one comprising transgene B, the transduced cells will be a mixture of cells expressing A alone; B alone; and cell expressing both A and B. In this situation, cells expressing A and B are combinatorially transduced.

For cells transduced with three vectors each comprising a transgene, the resulting transduced cells will be a mixture of: A alone; B alone; C alone; A and B; A and C; B and C; and cells expressing A, B and C. In this situation, the three sub-populations, expressing A and B; A and C; B and C; and cells expressing A, B and C are combinatorially transduced.

The cell composition comprises a plurality of sub-populations derived by transduction with different vector combinations in the mixture of viral vectors.

The cell composition may comprise cytolytic immune cells such as a T cells and/or or NK cells.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

Natural Killer cells (or NK cells) form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The cells of the invention may be any of the cell types mentioned above.

The cells to be transduced with a method of the invention may be derived from a blood sample, for example from a leukapheresate. The cells may be or comprise peripheral blood mononuclear cells (PBMCs).

Cells may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, cells may be derived from ex vivo differentiation of inducible progenitor cells or embryonic progenitor cells to, for example, T or NK cells. Alternatively, an immortalized T-cell line which retains its lytic function and could act as a therapeutic may be used.

The cells may be activated and/or expanded prior to being transduced with nucleic acid encoding the molecules providing the chimeric polypeptide according to the first aspect of the invention, for example by treatment with an anti-CD3 monoclonal antibody.

After transduction, the cells may then by purified, for example, selected on the basis of expression of the CAR. It may be desirable to select cells on the basis of CAR expression when there may be a sub-population of cells post-transduction which express an activity modulator in the absence of a CAR. Where each of the vectors in the mixture of viral vectors comprises a nucleic acid sequence encoding a CAR, it may not be necessary to purify or sort cells on the basis of CAR-expression, as it should not be possible for any cells to express an activity modulator in the absence of a CAR.

Pharmaceutical Composition

The cell composition of the present invention, comprising a mixture of singly and combinatorially transduced CAR-expressing cells, may be administered to a patient as a pharmaceutical composition.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating a disease which comprises the step of administering the a cell composition of the present invention (for example in a pharmaceutical composition as described above) to a subject.

A method for treating a disease relates to the therapeutic use of the cell composition of the present invention. The cell composition may be administered to a subject having an existing disease or condition in order to lessen, reduce or improve at least one symptom associated with the disease and/or to slow down, reduce or block the progression of the disease.

The method for preventing a disease relates to the prophylactic use of the cell composition of the present invention. The cell composition may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a cell-containing sample;
(ii) transducing the such cells with a mixture of at least two viral vectors;
(iii) administering the cells from (ii) to a subject.

The present invention also provides a cell composition of the present invention for use in treating and/or preventing a disease.

The invention also relates to the use of a cell composition of the present invention in the manufacture of a medicament for the treatment of a disease.

The disease to be treated by the methods of the present invention may be a cancerous disease, such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

The disease may be Multiple Myeloma (MM), B-cell Acute Lymphoblastic Leukaemia (B-ALL), Chronic Lymphocytic Leukaemia (CLL), Neuroblastoma, T-cell acute Lymphoblastic Leukaemia (T-ALL) or diffuse large B-cell lymphoma (DLBCL).

The disease may be a plasma cell disorder such as plasmacytoma, plasma cell leukemia, multiple myeloma, macroglobulinemia, amyloidosis, Waldenstrom's macroglobulinemia, solitary bone plasmacytoma, extramedullary plasmacytoma, osteosclerotic myeloma, heavy chain diseases, monoclonal gammopathy of undetermined significance or smoldering multiple myeloma.

The cells of the composition of the present invention may be capable of killing target cells, such as cancer cells. The target cell may be characterised by the presence of a tumour secreted ligand or chemokine ligand in the vicinity of the target cell. The target cell may be characterised by the presence of a soluble ligand together with the expression of a tumour-associated antigen (TAA) at the target cell surface.

Different subpopulations of cells within the composition of the invention may have different levels of ability to kill target cells, both between different patients having the same disease and within a patient at different disease sites (e.g. tumour sites).

Results-Based Engineering of CAR-Expressing Cells

The present invention also provides a method for determining the optimal combination of components for a CAR-expressing cell to treat a disease.

As explained above, the cell composition of the invention comprises a mixture of CAR-expressing cells, some of which are single transduced and some of which are combinatorially transduced. The number of different subpopulations will depend on the number of viral vectors in the mixture used for transduction. For three vectors A, B and C, there should be seven populations of transduced cells: those transduced with: A alone; B alone; C alone; A and B; A and C; B and C; and A, B and C. For four vectors, A, B, C and D, there should be 15 different subpopulations: A alone; B alone; C alone; D alone; A and B; A and C; A and D; B and C; B and D; C and D; A, B and C; A, B and D; A, C and D; B, C and D; and A, B, C and D.

If each vector in the composition comprises a nucleic acid encoding a CAR and/or a nucleic acid encoding an activity modulator, then the cell composition will be a mixture subpopulations of transduced cells each expressing a different combination of CAR(s) and activity modulator(s).

For example, the mixture of viral vectors may express one or more CAR(s) and a plurality of different activity modulators. CAR-expressing cells made by transduction of cells with the mixture of vectors will express a plurality of different combinations of activity modulator(s) which may give the CAR-expressing cell different properties in terms of target cell killing, survival, engraftment, resistance to checkpoint inhibition and/or resistance to the hostile tumour microenvironment. In vivo, one subpopulation of cells expressing a particular combination of CAR(s) and activity modulators will be best suited to the particular conditions within the patient or within a particular site in the patient. That subpopulation will receive the most effective activation, survival and/or proliferation signal and will "win out" from other subpopulations in the cell composition.

By analysing CAR-expressing cells in a patient following administration, it is possible to work out which subpopulation is best survive, engraft and kill target cells. By analysing the phenotype or genotype of this subpopulation, it is then possible to work out which combination of vectors the subpopulation were successfully transduced with during the making of the cell composition.

This information may be used to design a homogenous CAR-expressing cell composition, in which every transduced cells expresses the most successful combination of CAR(s) and activity modulator(s).

The method may comprise the following steps:
(i) administering a cell composition to a subject having the disease;
(ii) monitoring the patient or sample(s) from the patient to determine which sub-population of cells in the cell composition show the greatest level of survival, engraftment, proliferation activation and/or target cell killing; and
(iii) analysing the phenotype/genotype of the cells in the sub-population to ascertain the CAR(s) and/or activity modulator(s) expressed by those cells.

There is also provided a method for producing a CAR-expressing cell composition for use in the treatment of a disease which comprises the step of determining the optimal combination of components for a CAR-expressing cell to treat a disease by a method described above, then transducing cells with a single vector expressing the identified combination of components. The resulting cell composition will be homogeneous in the sense that all CAR-expressing cells will express the same combination of components.

It is also possible to transducing cells with two or more vectors expressing the identified combination of components, then sort for cells which express all identified components in order to arrive at a homogeneous CAR-expressing cell composition.

The present invention also provides a cell composition made by such a method.

The invention will now be further described by way of Examples, which are meant to serve to assist one of ordinary skill in the art in carrying out the invention and are not intended in any way to limit the scope of the invention.

EXAMPLES

Example 1—Generation of a CAR-T Cell Composition Transduced with Multiple Vectors Lentiviral vectors were generated expressing either a) the second-generation anti-CD19 CAR described in WO2016/139487 which comprises an anti-CD19 antigen binding domain, a CD8 stalk spacer and transmembrane domain, and a compound 4-1BB-CD3ζ endodomain under the control of a PGK promoter (pCCL.PGK.aCD19cat-CD8STK-41BBZ); or b) an anti-CD22 CAR having CDRs shown as SEQ ID No. 10-15 above, a CD8 stalk spacer and a second generation endodomain comprising CD3ζ and a 4-1BB costimulatory domain, under the control of an EF1α promoter (pCCL.EF1a.aCD22_9A8-1-64_LH_scFv-CD8STK-41BBz).

Figure 6:
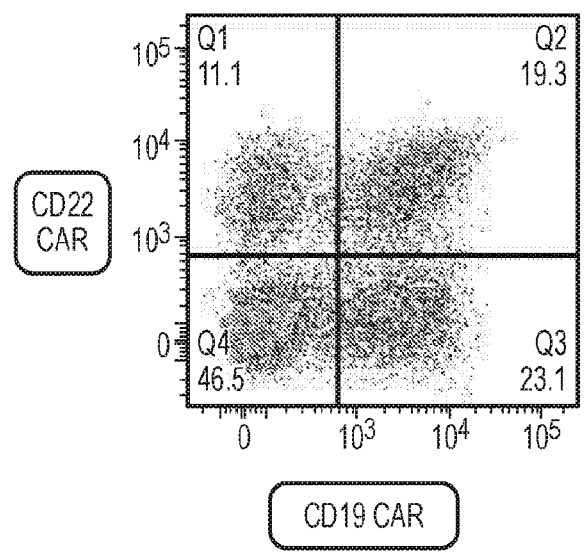
FIG. 6—Scatter plot showing that when T cells are transduced with a mixture of vectors (A and B), a proportion of cells are left untransduced; a proportion of cells are transduced with vector A alone; a proportion of cells are transduced with vector B alone; and a proportion of cells are transduced with vectors A and B. In this study, cells are transduced with a mixture of vectors, one of which expresses an anti-CD19 CAR and one of which expresses a CD22 CAR.

Two separate lentiviral supernatants were produced and mixed 1:1 at an MOI of 2.5+2.5. The pattern of expression of the two CARs was investigated by flow cytometry using an anti-idiotype antibody to stain for expression of the anti-CD19 CAR and soluble CD22 to stain for expression of the CD22 CAR. The results are shown in FIG. 6. Post-transduction with the lentiviral composition, the cells are a mixture of untransduced cells (46.5%); cells expressing the anti-CD19 CAR alone (23.1%); cells expressing the anti-CD22 CAR alone (11.1%) and cells expressing both the CD19 and CD22 CARs (19.3%).

Example 2—Expression of CAR(s) in Combination with Enhancement Module(s) in a Combinatorial Fashion by Transduction with Multiple Vectors Vectors are constructed which contain a second generation anti-CD19 CAR (Fmc63-41 BBz) in combination with a marker gene and one of the following enhancement modules, which are predicted to display activity under specific conditions:

dnSHP2—A truncated version of SHP2 which has the SH2 domains but lacks the phosphatase domain. The sequence is shown above as SEQ ID No. 29. The truncated protein acts as a dominant negative and competes with the wild-type proteins for binding to phosphorylated ITIM on inhibitory immunoreceptors such as PD1.

dnTGFBRII—A dominant negative TGFβ receptor which lacks the kinase domain. The sequence is shown above as SEQ ID No. 46. The dnTGFBRII competes with wild-type TGF-β receptor for binding to TGF-β, downregulating TGFβ-mediated signalling.

CCR—A constitutively active chimeric cytokine receptor having an IL-2, IL-7 or GM-CSF receptor endodomain, as described above. The sequences for components of for such constitutively active CCRs are given above as SEQ ID No. 30-43. The present of such a receptor causes constitutive cytokine signalling (i.e. in the absence of the relevant cytokine).

Retroviral vectors are constructed containing the following cassettes, in which GFP, mKate and RQR8 are marker genes:
Vector A—CAR+dnSHP+GFP
Vector B—CAR+dnTBRI I+mKate
Vector C—CAR+CCR+RQR8

T cells are transduced with a mix of two retroviruses encoding two of the above vectors in a 1:1 mixture at an MOI of 2.5:2.5. The resulting mixed population contains T cells expressing the first vector OR the second vector OR both vectors together. Transduction is detected and measured by flow cytometry measuring the expression of the marker genes. For example, for cells transduced with a mixture of vectors A and B, transduction is detected and measured using the marker genes GFP and m Kate.

The transduced T cell population is labelled with the dye Cell Trace Violet (CTV), a fluorescent dye which is hydrolysed and retained within the cell. It is excited by the 405 nm (violet) laser and fluorescence can be detected in the pacific blue channel. The T-cells are resuspended at $2\times10^6$ cells per ml in PBS, and 1 ul/ml of 5 mM CTV is added. The T-cells are incubated with the CTV for 20 minutes at 37° C. Subsequently, the cells are quenched by adding 5V of complete media. After a 5 minutes incubation, the T-cells are washed and resuspended in 2 ml of complete media. An additional 10 minute incubation at room temperature allows the occurrence of acetate hydrolysis and retention of the dye.

Labelled T-cells are co-cultured with CD-19 expressing target cells for four or seven days. In order to investigate the function of the dnSHP2 enhancement module in vector mixtures comprising Vector A, target cells are used which co-express the target antigen and PDL1. In order to investigate the function of the dnTBRII enhancement module in vector mixtures comprising vector B, T-cells are co-cultured with target cells in the presence of soluble TGF-β.

The assay is carried out in a 96-well plate in 0.2 ml total volume using $5\times10^4$ transduced T-cells per well and an equal number of target cells (ratio 1:1). At the day four or day 7 time point, the T-cells are analysed by flow cytometry to measure the dilution of the CTV which occurs as the T-cells divide. The number of T-cells present at the end of the co-culture is calculated, and expressed as a fold of proliferation compared to the input number of T cells.

Preferential expansion in the module corresponding to the immunosuppression exerted by the target cells is assessed by a decrease in cell trace violet dye in that population and by an increase in the marker corresponding to that population.

Example 3—Generation of an Anti-GD2-CAR T-Cell Product with Enhancement Modules by Dual Transduction with Two Separate Retroviral Vectors Background: Neuroblastoma is the most common extracranial solid cancer in children with poor long-term survival in those with high-risk disease.

A currently ongoing phase I clinical study of GD2-targeted CART for refractory/relapsed neuroblastoma (NCT02761915) shows activity against disseminated disease without inducing on target/off tumor toxicity. However, CART persistence was limited and clinical activity transient and incomplete.

Building on the GD2 CAR used in this study, we have developed a next generation T-cell product candidate termed AUTO6NG. The AUTO6NG product consists of 3 distinct populations of GD2-targeted CAR T-cells, produced by dual transduction of T-cells with two separate retroviral vectors. The first vector directs the expression of a GD2-targeting CAR, co-expressed with a constitutively signalling IL7 cytokine receptor (IL7R_CCR) or a constitutively signalling IL2 cytokine receptor (IL2R_CCR) (product A), while the second vector is a tri-cistronic retroviral vector encoding the same GD2 CAR, co-expressed with dominant negative TGFbRII (dnTGFbRII) and truncated SHP2 (dSHP2) (product B). dSHP2 confers resistance to inhibitory signals such as those from PD1.

Figure 7:
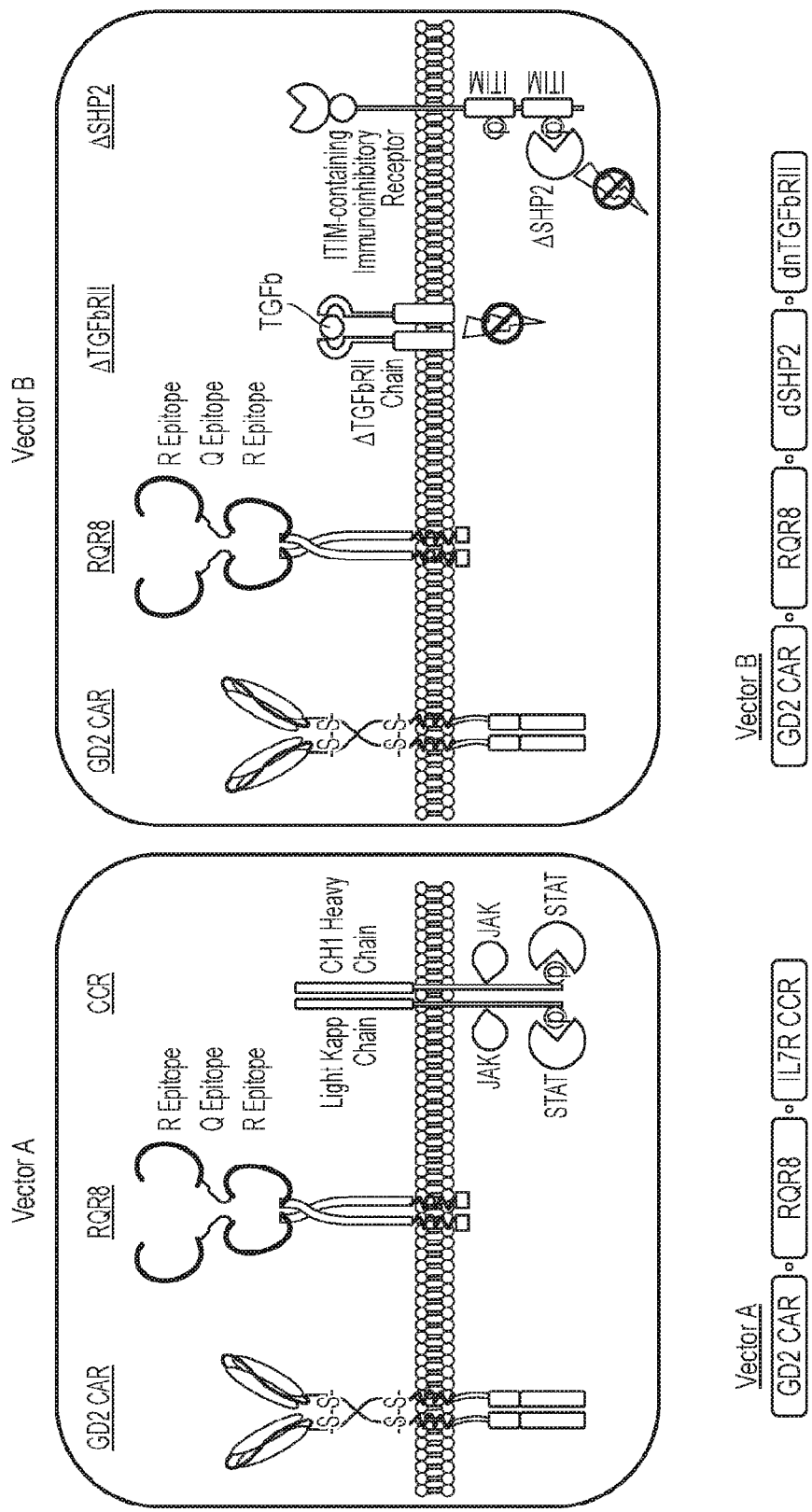
FIG. 7—Schematic diagram illustrating the molecules expressed by the vectors used in the dual vector composition described in Example 3. Vector 1 expresses a CAR with an antigen-binding domain which binds GD2 (GD2 CAR), a constitutively active cytokine receptor (CCR) and a sort/suicide gene (RQR8). Vector 2 expresses the same GD2 CAR, a dominant negative SHP-2 (ΔSHP2); a dominant negative transforming growth factor (TGF)βII receptor (ΔTGFbRII) and the same sort/suicide gene (RQR8).

The vector design is illustrated schematically in FIG. 7.

The GD2 CAR is as described in WO2015/132604, with an antigen-binding domain with a VH domain having the sequence shown as SEQ ID No. 77 and a VL domain having the sequence shown as SEQ ID No. 78.

The constitutively signalling IL2 and IL7 cytokine receptors are as described in WO2017/029512, The IL2 CCR comprises a comprising a first polypeptide having an IL-2 receptor β-chain endodomain (SEQ ID No. 40) and a second polypeptide comprising a common γ-chain receptor endodomain (SEQ ID No. 39); whereas the IL7 CCR comprises a first polypeptide having an IL-7 receptor α-chain endodomain (SEQ ID No. 41) and a second polypeptide comprising a common γ-chain receptor endodomain (SEQ ID No. 39).

The sort/suicide gene RQR8 is as described in WO2013/153391 and has the sequence shown as SEQ ID No. 79.

The dominant negative TGFbRII (dnTGFbRII) has the sequence shown above as SEQ ID No. 46.

The truncated SHP2 (dSHP2) has the sequence shown above as SEQ ID No. 29.

Example 4—Investigating the Cytotoxic Capacity of Single and Dual Transduced Cells and the Function of Various Vector-Expressed Elements In Vitro Human T-cells were either dual transduced with both vectors yielding a mix of product A/B/A+B (AUTO6NG) or single transduced with each vector individually giving raise to product A or B. Controls included non-transduced cells (NT) and cells expressing GD2 CAR alone.

i) Cytotoxicity Assay

Figure 8:
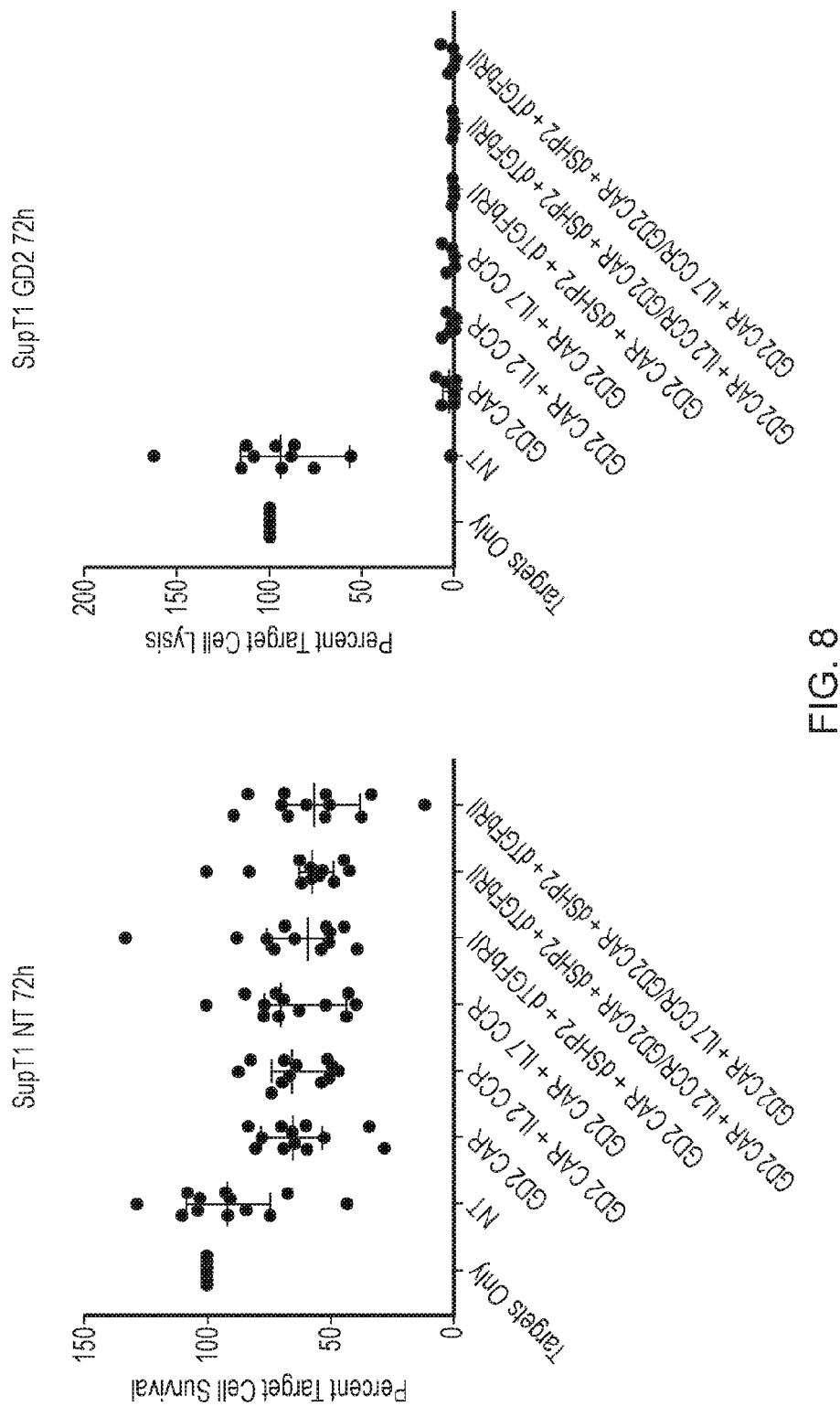
FIG. 8—Investigating the capacity of single and dual transduced T cell populations to kill GD2-expressing (SupT1 GD2) and non-expressing (SupT1 NT) target cells.

The various effector cell types were co-cultured with GD2-expressing SupT1 target cells (SupT1 GD2) or control, non-transduced target cells (SupT1 NT) for 72 hours and the percentage of target cell lysis was analysed by flow cytometry. The results are shown in FIG. 8. All CAR-expressing effector cells were capable of killing GD2-expressing target cells. T-cells transduced with the dual vector composition (product A/B/A+B) were highly potent in cytotoxicity assays against GD2 positive tumour cell lines with no differences observed compared with single transduced CAR T-cells (product A or B).

ii) Validation of the CCR

Figure 9:
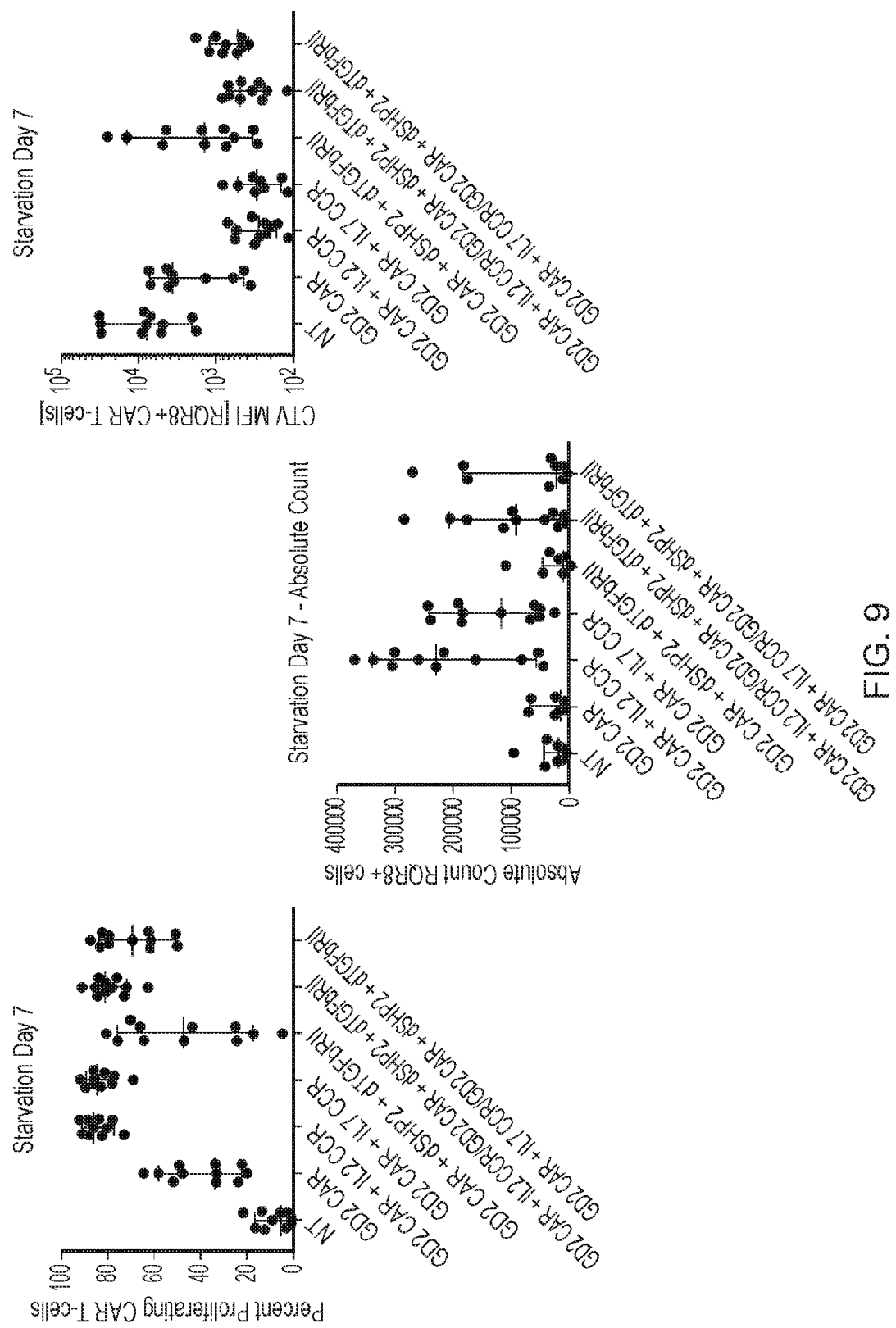
FIG. 9—Investigating the proliferation of single and dual transduced T cell populations following culture in cytokine-free complete cell culture media for 7 days without further antigen stimulus.

The various transduced CAR T-cells described above and control NT T-cells were labelled with Cell Trace Violet (CTV) and cultured in cytokine-free complete cell culture media for 7 days without further antigen stimulus. In vitro persistence was quantified as percent proliferating cells which have diluted the CTV dye and absolute CAR T-cell count after 7 days. The results are shown in FIG. 9. T cells transduced with product A, expressing either the constitutively signalling 1L7 cytokine receptor (IL7R_CCR) or the constitutively signalling IL2 cytokine receptor (IL2R_CCR); or transduced with product A+B showed increased proliferation compared with untransduced cells (NT), cells transduced with a vector expressing GD2 CAR alone, or cells transduced with the vector expressing product B alone (GD2 CAR+dSHP2+dTGFbRII). Expression of either the 1L2 or IL7R_CCR conferred exogenous-cytokine-independent viability and homeostatic proliferation of modified T-cells, without causing autonomous T-cell growth.

iii) Validation of the dTGFbRII

Figure 10:
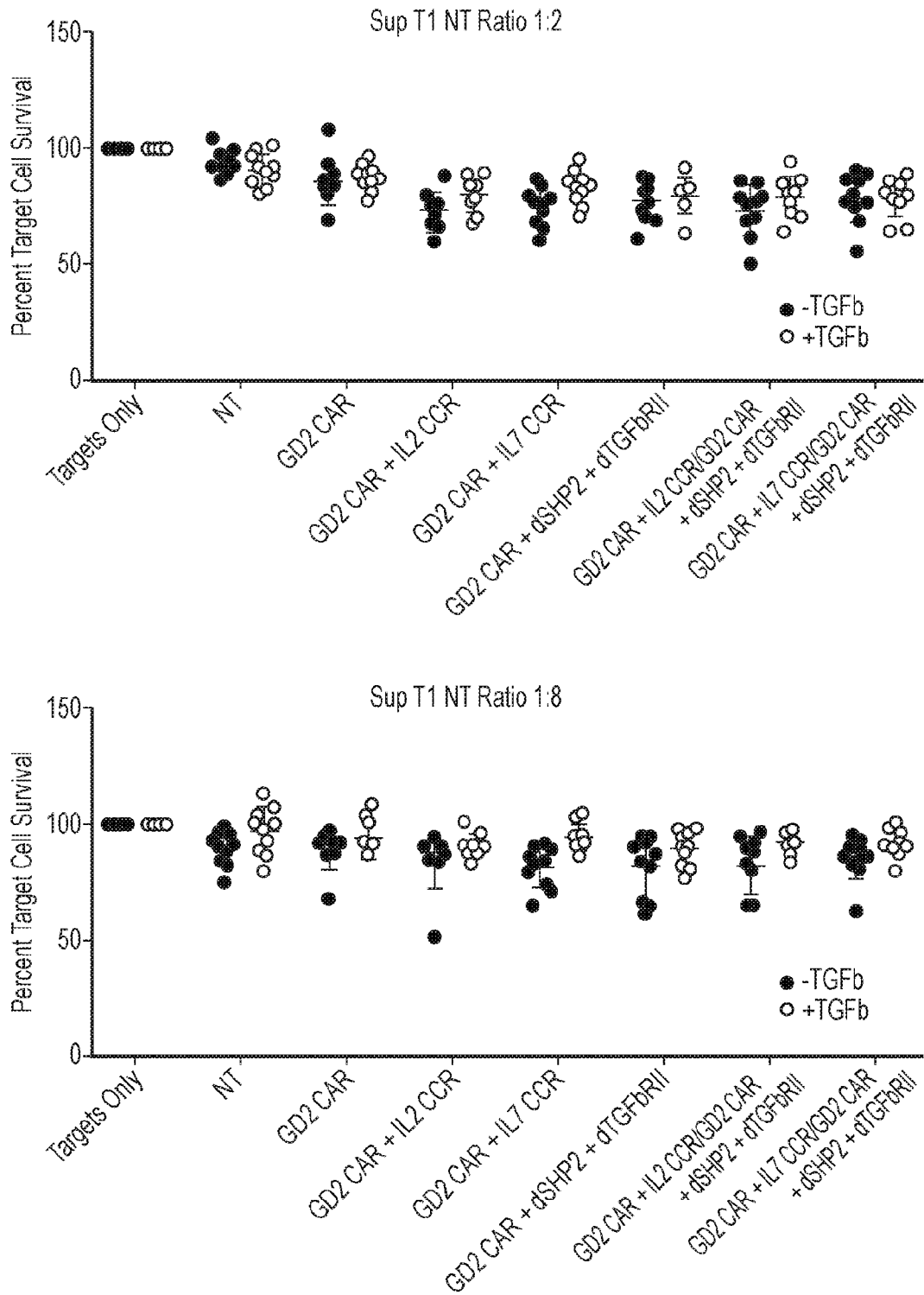
FIG. 10—Investigating the capacity of single and dual transduced T cell populations to kill GD2-expressing (SupT1 GD2) and non-expressing (SupT1 NT) target cells in the presence or absence of TGFβ.
Figure 10:
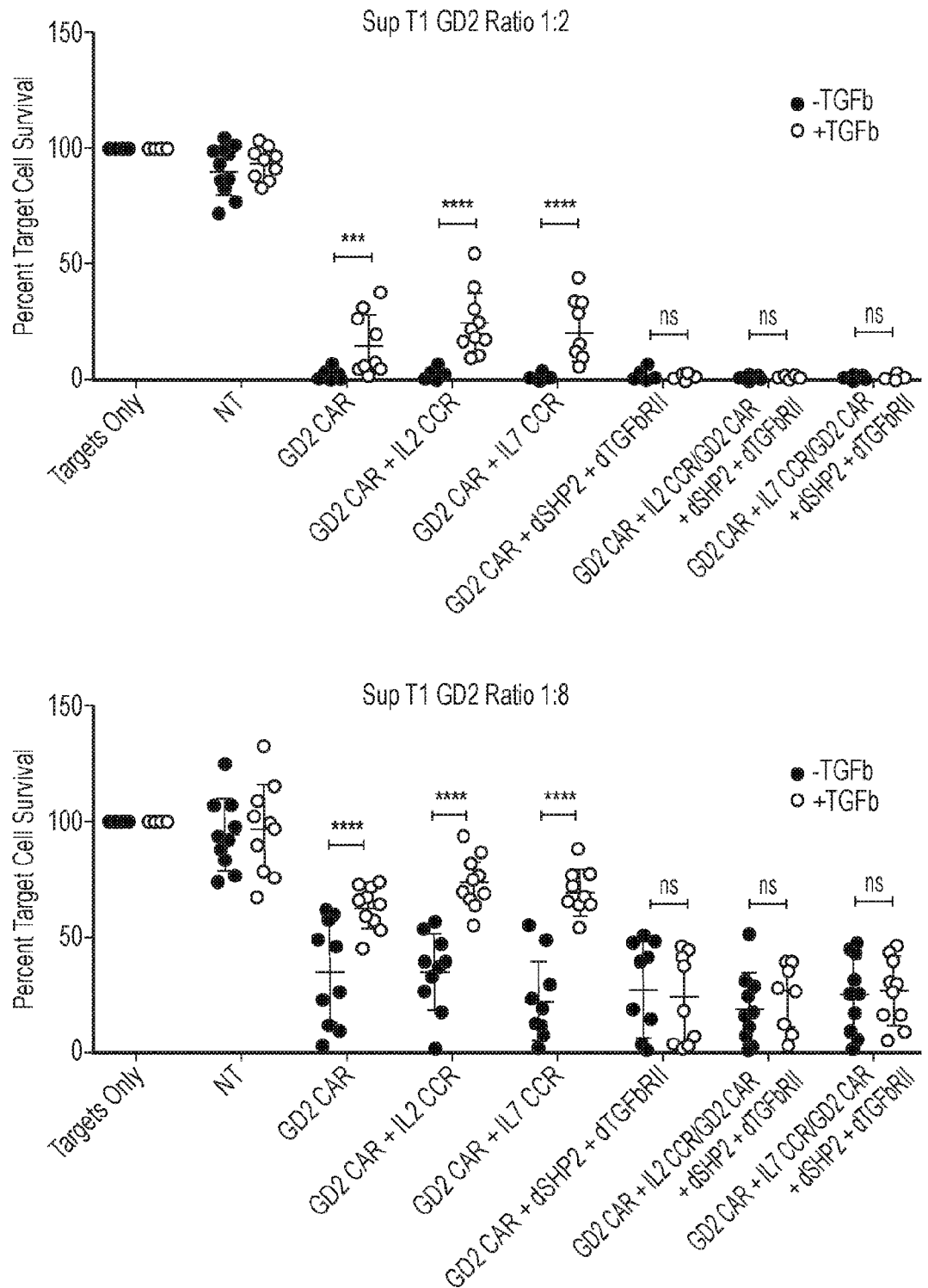
Figure 11:
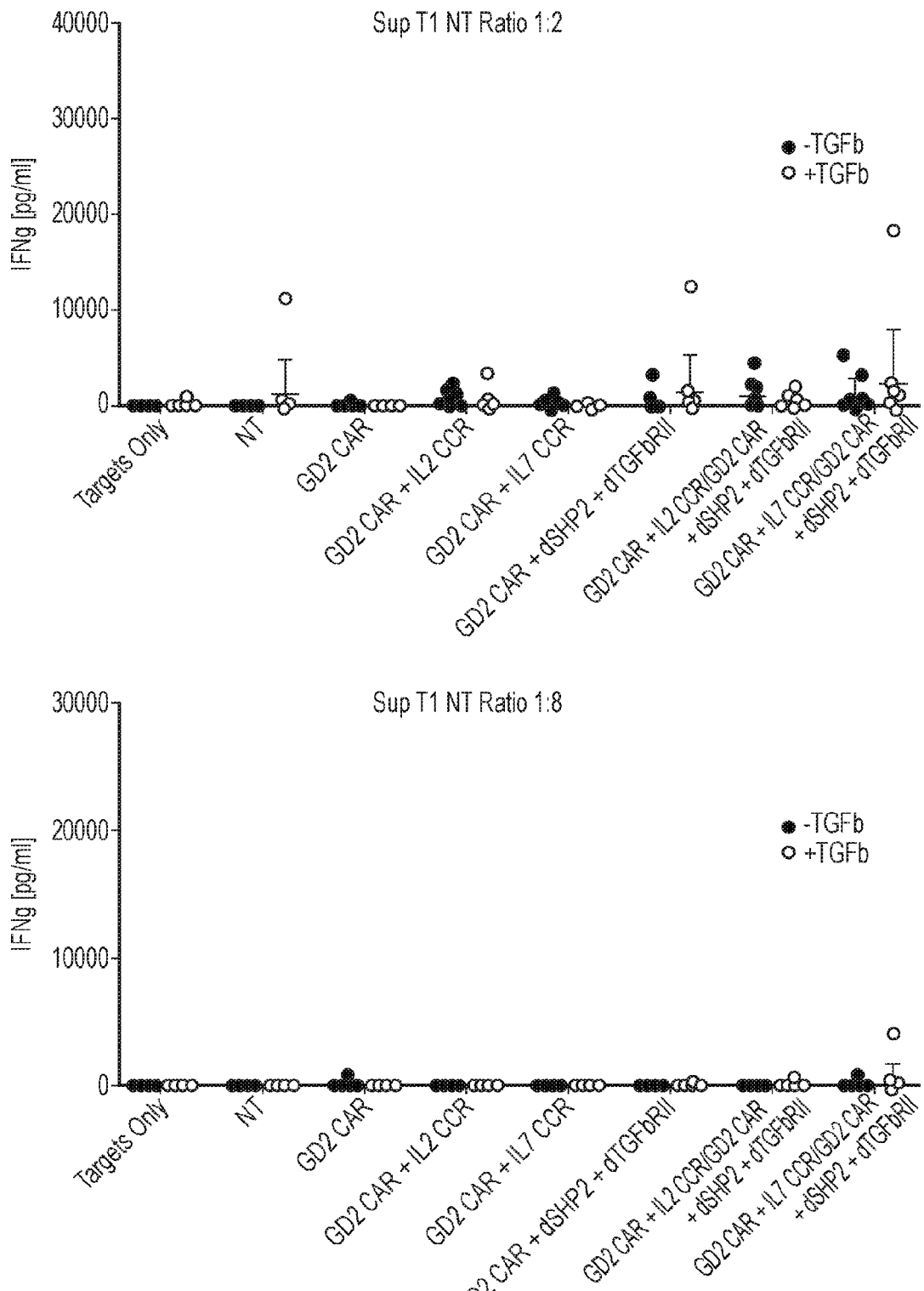
FIG. 11—Investigating cytokine production (IFNγ) from single and dual transduced T cell populations following co-culture with GD2-expressing (SupT1 GD2) and non-expressing (SupT1 NT) target cells in the presence or absence of TGFβ.
Figure 11:
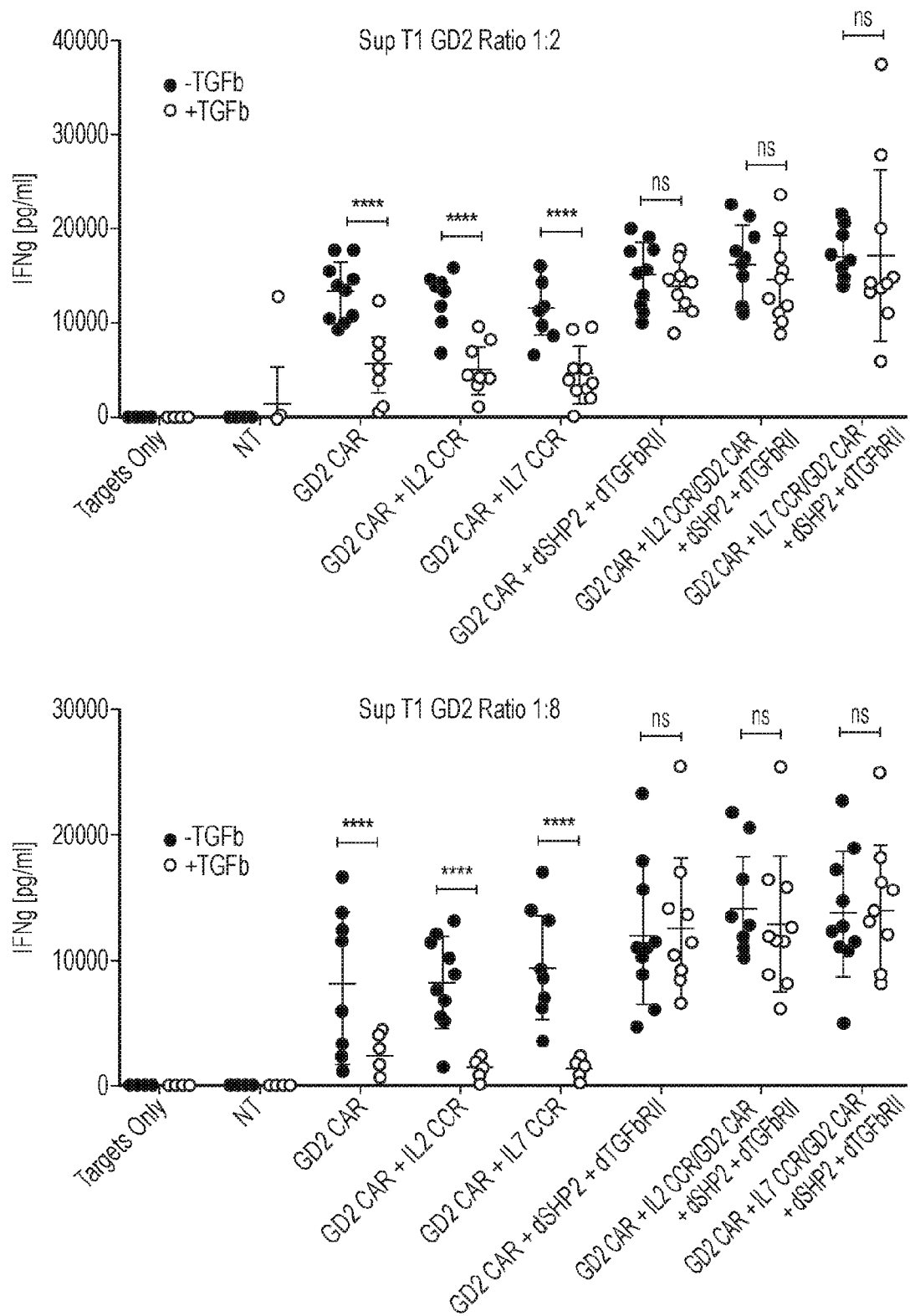
Figure 12A:
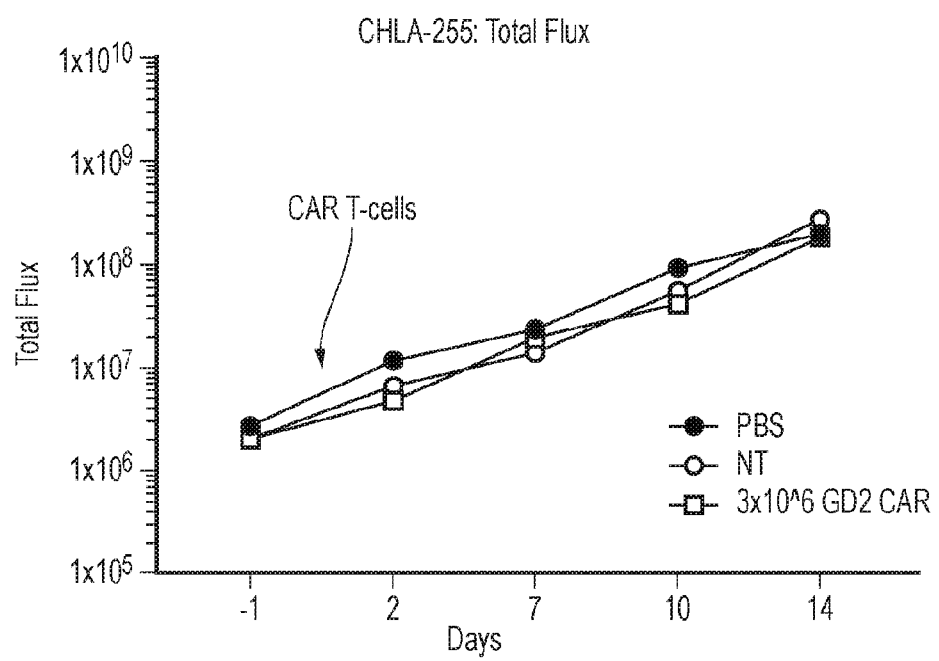
FIGS. 12A-12D—Results of an in vivo assay investigating the anti-tumour activity of T cells transduced with the dual vector composition by intravenous administration in an established neuroblastoma xenograft model in NSG mice. 1×10⁶ CHLA-255 Fluc cells were injected i.v. into female NSG mice. Xenografts were left to establish for 15 days until stable engraftment was detectable by BLI. CAR-T cells were made either by transducing cells with a single vector expressing a GD2 CAR (GD2 CAR) or by transducing cells with the dual vector composition described in Example 3 and Illustrated in FIG. 7 (GD2 CAR+IL7 CCR/GD2 CAR+dSHP2+dTGFbRII). CAR T-cells were administered i.v. at a dose of 3×10⁶ CAR T-cells/mouse. Quantitated bioluminescent signal of CHLA-255 Fluc was plotted over time as total flux (photons/s) FIG. 12A. Graph showing fluorescent signal over time for mice receiving CAR-T cells expressing GD2 CAR alone (GD2 CAR); untransduced T cells (NT) or buffer alone (PBS).
Figure 12B:
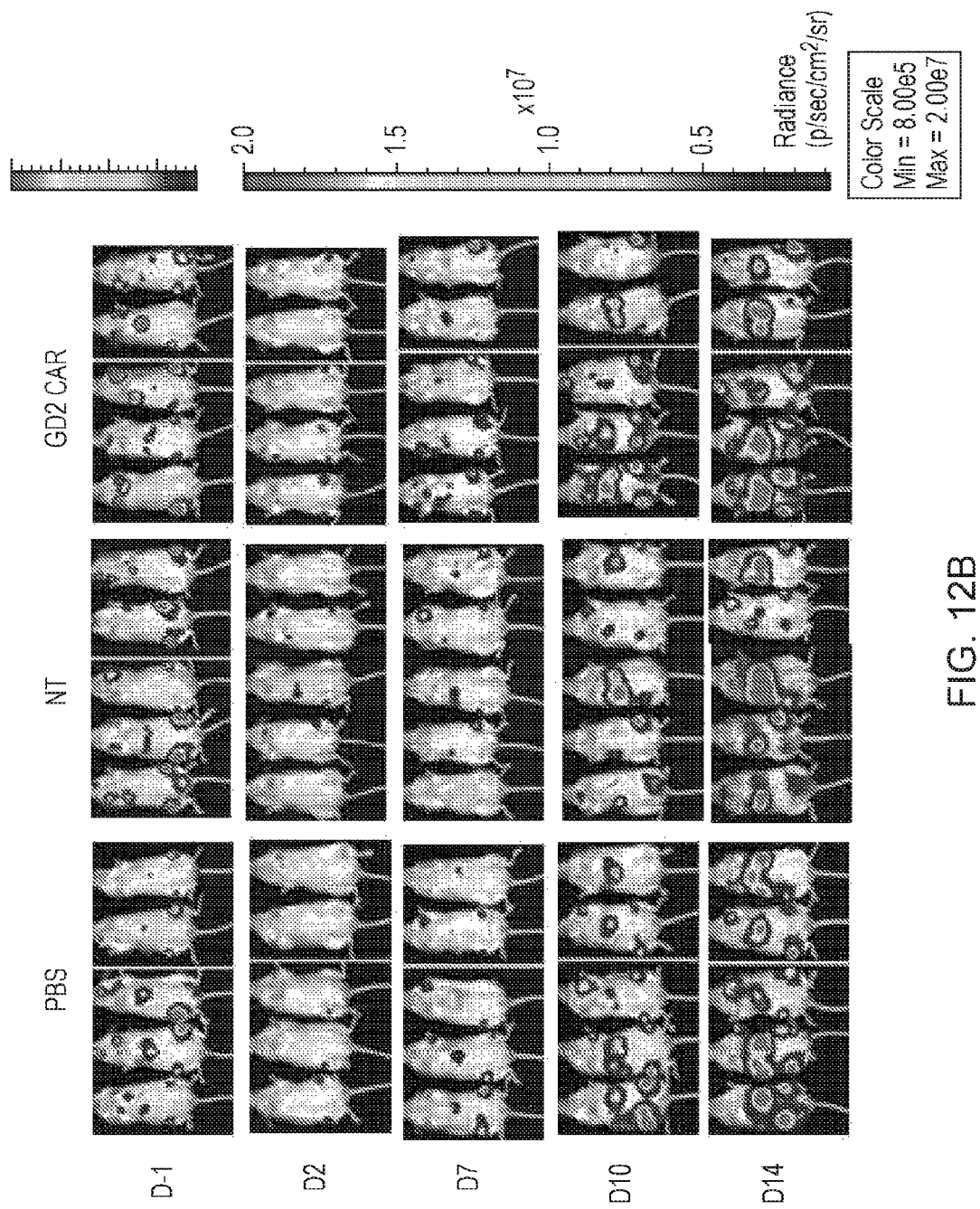
Figure 12C:
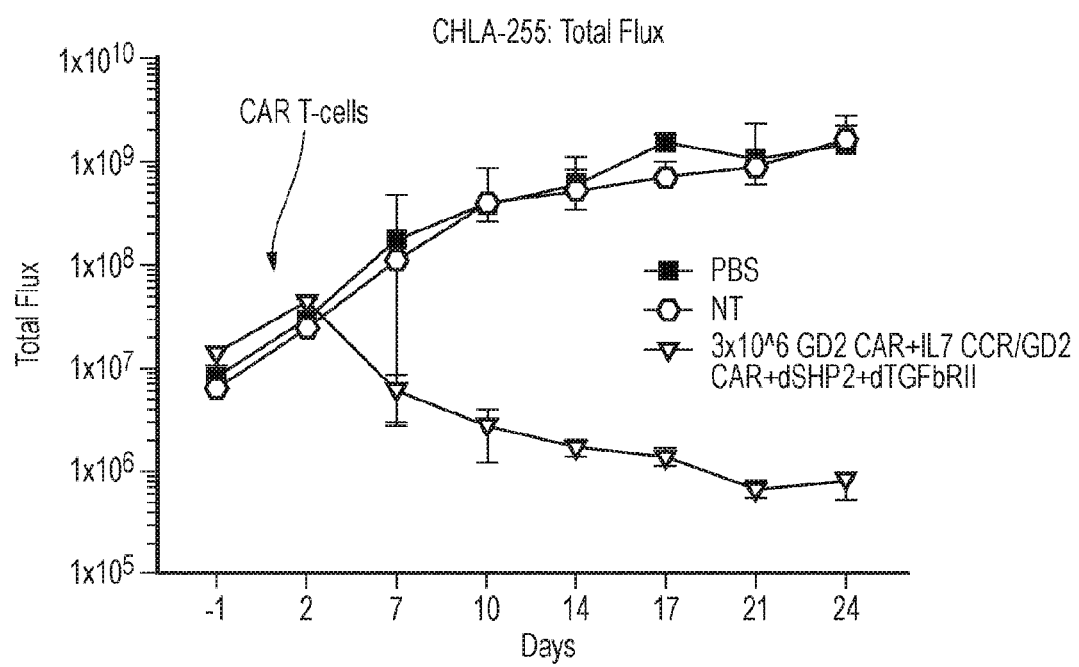
Figure 12D:
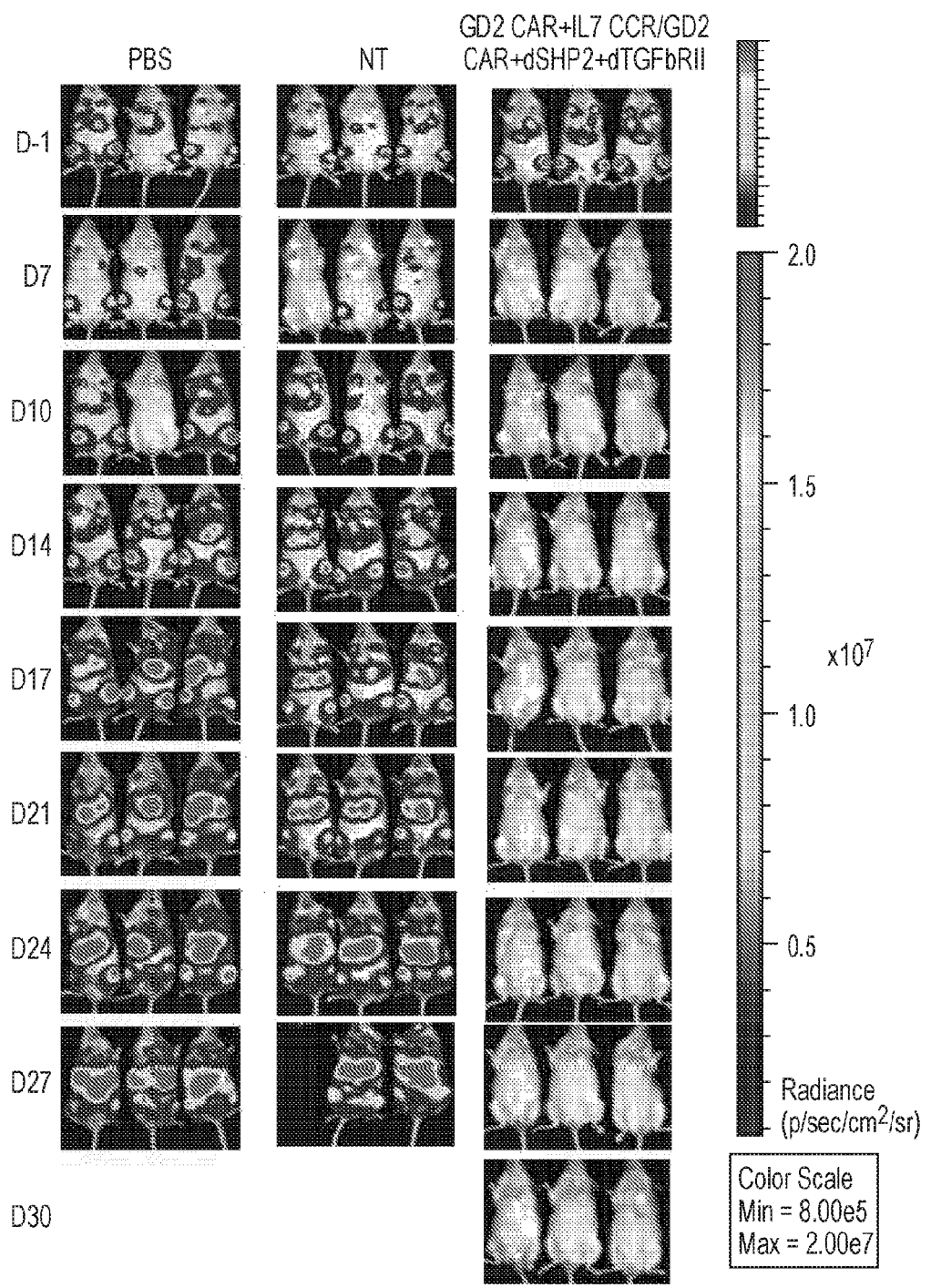

The various transduced CAR T-cells described above and control NT T-cells were co-cultured with GD2-expressing SupT1 target cells (SupT1 GD2) or control, non-transduced target cells (SupT1 NT) at a 1:2 or 1:8 E:T ratio, for 7 days, in the presence or absence of 10 ng/ml TGFβ. Killing of target cells was analysed by flow cytometry and secretion of IFNγ was analysed by ELISA. The results are shown in FIGS. 10 and 11 respectively. CAR T cells transduced with product B, expressing dnTGFbRII; or transduced with product A+B, showed resistance to TGFβ-mediated inhibition of target cell killing compared with CAR-T cells expressing GD2 CAR alone, or cells transduced with the vector expressing either product A alone (GD2 CAR+1L2 CCR or GD2 CAR+1L7 CCR). CAR T cells transduced with product B or product A+B, showed restoration of IFNγ secretion in the presence of TGFβ to a level comparable to that observed in the absence of TGFβ. By contrast, IFNγ secretion by CAR-T cells expressing GD2 CAR alone, or cells transduced with the vector expressing either product A alone, was significantly inhibited by the presence of TGFβ. T-cells expressing dnTGFbRII therefore proved resistant to TGFβ-mediated immunosuppression in vitro.

Example 5—Investigating Anti-Tumour Activity of Dual-Transduced CAR-T Cell Product In Vivo in an Xenograft Model of Neuroblastoma An in vivo assay was used to investigate the anti-tumour activity of T cells transduced with a dual vector composition by intravenous administration in an established neuroblastoma xenograft model in NSG mice. Ten- to 14-week-old female NSG mice were intravenously injected with 1 million Firefly luciferase expressing CHLA-255 cells (CHLA-255

FFluc). Xenografts were left to establish for 15 days until stable engraftment was detectable by BLI. CAR-T cells were made either by transducing cells with a single vector expressing a GD2 CAR (GD2 CAR) or by transducing cells with the dual vector composition described in Example 3 and Illustrated in FIG. 7 (GD2 CAR+IL7 CCR/GD2 CAR+dSHP2+dTGFbRII). Mice were injected intravenously with $10 \times 10^6$ CAR T-cells (50% transduction efficiency), $3 \times 10^6$ CAR T-cells (50% transduction efficiency), $20 \times 10^6$ NT T-cells (total T-cells equivalent to $10 \times 10^6$ CAR T-cell dose) or PBS. Fourteen days later, tumour growth was assessed by bi-weekly bioluminescent imaging.

The results are shown in FIG. 12. Intravenous delivery of CAR T cells expressing a simple GD2 CAR alone had no significant effect on tumour growth (FIGS. 12A and B). By contrast, intravenous delivery of CAR T cells transduced with the dual vector composition at both the $3 \times 10^6$ and $10 \times 10^6$ doses exhibited potent anti-tumour activity and extended survival in NSG mice with established tumour burden (FIGS. 12C and D).

Example 6—Generation of an Anti-PSMA CAR T-Cell Product with Enhancement Modules by Triple Transduction with Three Separate Retroviral Vectors The present inventors developed a combinatorial/multimodular CAR T therapeutic for the treatment of prostate cancer ("AUTO7") which consists of several functional modules: 1) an anti-PSMA CAR having a second generation CD28-CD3z compound endodomain, (7A12-28z); 2) a safety switch, RapaCasp9 which is described in WO2016/135470 and has the sequence shown as SEQ ID No. 80 above; 3) dominant negative TGFβRII to induce TGFβ1 resistance (dnTBRII) having the sequence shown as SEQ ID No. 46 above; 4) truncated SHP2 (dnSHP2) for PD1/PD-L1 pathway inhibition having the sequence shown as SEQ ID No. 29 above; 5) a constitutively active IL7 receptor (CCR_IL7) to induce proliferation as described above; 6) a sort-suicide gene RQR8 having the sequence shown as SEQ ID No. 79; and 7) an ultra-low-secreting IL-12 (flexiIL-12) for lymphocyte recruitment/activation which is positioned downstream of a stop-skip sequence (SS) which has the sequence shown as SEQ ID No. 81. The vector design is shown in FIG. 13A.

The first vector (A) encodes dnSHP2, the suicide gene RQR8, the CAR and dnTBRII; the second vector (B) encodes the constitutively active IL7 receptor; the third vector (C) encodes a second suicide gene: Rapcasp9; and flexi-IL12.

Having different suicide genes on vector A and vector C provides flexibility. If a CAR-related toxicity is observed in the patient, then it is possible to selectively remove cells expressing the CAR in the usual way treating the patient with Rituximab, which triggers apoptosis of these cells via the RQR8 sort/suicide gene. If, however, a toxicity is observed which is thought to be related to IL-12 secretion, then cells can be selectively destroyed which are transduced with vector C by adding rapamycin or a rapamycin analogue to trigger apoptosis via the RapaCasp9 suicide gene. As the therapeutic product comprises cells transduced with a mixture of three vectors, it will be a combinatorial product, with distinct subpopulations of cells transduced with all the various combinations of one, two or all three vectors. This means that some CAR-expressing cells should survive triggering of the RapaCasp9 suicide gene. For example, cell transduced with vector A alone or the combination of vectors A and B will not express RapaCasp9 and should be unaffected by treatment with rapamycin. This means that it is possible to "modify" the therapeutic product in vivo and selectively delete the IL-12 expressing cells, while leaving a proportion of CAR-expressing cells to maintain the CAR-mediated anti-tumour effect.

AUTO7 was investigated as product of a single transduction using the vector A. ("AUTO7/A"), or double transduction using vectors A and B ("AUTO7/AB"), or triple transduction using vectors A, B and C ("AUTO7/ABC"). AUTO7 was tested against a second generation CAR developed using the same anti-PSMA binder 7A12 ("Parental").

Example 7—Investigating the Cytotoxic Capacity of Single, Dual and Triple Transduced Cells and the Function of Various Vector-Expressed Elements In Vitro The capacity of the T-cells transduced with the single, dual and triple vector combinations described above to kill target cells was investigated using a FACS-based killing assay. SupT1 cells engineered to express human PSMA antigen at different levels (SupT1-PSMAhigh, SupT1-PSMAlow) were used as target cells. Non-engineered SupT1 cells (SupT1-NT) were used as a negative control. CAR T-cells were co-cultured with target cells at 1:2 effector to target ratios. FBK was assayed after 24 h of incubation by cytofluorimetry analysis and the results are shown in FIG. 14A. Secretion of IL-2 and IFNγ by CAR T-cells was measured by collecting supernatant at 24 hr from the co-cultures described and detected by ELISA and the results are shown in FIGS. 14B and C respectively.

It was found that cell compositions produced by single transduction using the vector A. ("AUTO7/A"), double transduction using vectors A and B ("AUTO7/AB"), or triple transduction using vectors A, B and C ("AUTO7/ABC") were all highly potent in cytotoxicity assays against PSMA positive tumour cell lines. Cytotoxicity and cytokine release were comparable to those observed with a second generation CAR developed using the same anti PSMA binder 7A12 ("Parental") which was used as a CAR alone control.

In order to investigate the capacity of the single, dual and triple transduced AUTO7 T cells to kill target cells following culture in the absence of IL-2, transduced T-cells were cultured in starvation conditions with media without the supplement of 1L2 for 7 days. After 7 days CAR T-cells were counted and plated together with SupT1-PSMAhigh and SupT1-PSMAlow targets cells (or SupT1-NT cells as negative control). CAR T-cells were co-cultured with target cells at 1:2 and 1:8 effector to target ratios. FBK was assayed after 24 h of incubation by cytofluorimetry analysis (FIG. 15A). Secretion of IL-2 and IFNγ by CAR T-cells was measured by collecting supernatant at 24 hr from the co-cultures described and detected by ELISA (FIG. 15B).

It was found that, although cells expressing the control CAR and cells transduced with vector A alone showed in inhibition in cytotoxicity and cytokine release following culture under starvation conditions, this effect was less pronounced with cells transduced with the dual or triple vector combination (vectors A+B or A, B+C). Vector B comprises a gene expressing a constitutively active cytokine receptor: the IL7R_CCR module. Expression of this module confers cytokine independent viability and proliferation, without interfering with the cytotoxicity; since after starvation, cells transduced with the AUTO7/AB or AUTO7/ABC were shown to be still efficient at killing PSMA expressing target cells.

In order to investigate the capacity of the single, dual and triple transduced AUTO7 T cells to kill target cells in the presence of TGFβ, transduced T-cells were co-cultured with SupT1-PSMAhigh and SupT1-PSMAlow targets for 7 days at ratio 1:2 and 1:8 (E:T) either in the presence or absence of 10 ng/ml TGFβ1 (SupT1-NT were used as control). Target cell killing was quantified by FACS and normalised to targets alone. The results are shown in FIG. 16.

At a 1:8 E:T ratio, killing of target cells by T cells expressing the CAR alone control was inhibited by the addition of TGFβ1 to the culture medium. This inhibitory effect was reduced for cells transduced with any of the vector combinations A; A+B; or A, B+C. Vector A encodes the dnTGFβRII element which has been previously shown to block TGFβ-mediated inhibition of T-cell signalling.

In order to investigate the capacity of the single, dual and triple transduced AUTO7 T cells to kill target cells following repeated exposure to target antigen, transduced cells were co-cultured with SupT1-PSMAhigh or SupT1-PSMAlow target cells at 1:1 ratio (E:T) and every 7 days CAR T-cells were re-stimulated with $5 \times 10^4$ SupT1 cells.

Target cell killing was quantified by FACS before each new re-stimulation. The results are shown in FIG. 17.

After two restimulation events (week 2) cells transduced with the vector combination A+B or A+B+C showed much better killing of target cells than CAR-alone or Vector A-transduced cells. After three restimulation events (week 3) cells transduced with the vector combination A+B+C showed the best killing of target cells.

Example 8—Investigating the Cytotoxic Capacity of Single, Dual and Triple Transduced Cells and the Function of Various Vector-Expressed Elements In Vivo An in vivo assay was used to investigate the anti-tumour activity of T cells transduced with a single, dual or triple vector composition by intravenous administration in an established xenograft model in NSG mice.

Female NSG mice were injected with $5 \times 10^6$ PSMA positive PC3 human cell lines in the flank. Xenografts were left to establish for 3 weeks until stable engraftment was detectable by palpation and caliper measurement. CAR T-cells were administered i.v. at a dose of $1 \times 10^6$ CAR T-cells/mouse. Caliper measurement was taken 2/3 times a week. The results are shown in FIG. 18.

Mice treated with T-cells expressing the CAR alone (Parenteral) showed slowed tumour growth than those receiving non-transduced cells, but the tumour growth was not controlled. Mice receiving T cells transduced with vector A, which encodes CAR, dnSHP2 and dnTGFβRII, showed an initial growth in tumour (September 9) followed by a reduction in tumour size (September 23). At the end of the study, some resumption of tumour growth was observed (October 7).

Mice receiving T cells transduced with vector A+B showed an initial growth in tumour (September 9-16), but then the tumour size reduced and this effect continued for the duration of the study. Triple transduced AUTO7 CAR T cells completely eradicated tumour with no signs of toxicity. The vector combinations, especially A+B and A+B+C show a significant improvement over CAR alone in reducing tumour growth and promoting survival of mice in a xenograft model.

The results demonstrate the feasibility and efficacy of the multi-modular AUTO7 product. Addition of IL7R_CCR, ss_fIL12, dnTGFβRII and dSHP2 modules to the anti-PSMA CAR product enhanced T cell functions by extending persistence, proliferation, activation and resistance to TGFβ1 and PD1/PDL1 driven immune inhibition.

Methodology

Binder Generation

PSMA-binder was generated by CDR grafting of an anti-PSMA antibody derived from genetically vaccinated rats.

Cell Lines

PC3 cells, SupT1 cell lines (NT and PSMA+) were cultured in RPMI-1640 Medium supplemented with 10% fetal bovine serum (FBS) and 1% GlutaMAX. T-cells were isolated from peripheral blood mononuclear cells (PBMCs) and maintained in RPMI-1640 Medium supplemented with 10% FBS, 1% GlutaMAX and 100 U/mL IL-2.

Transduction

Retrovirus was generated by transiently transfecting HEK293T cells using GeneJuice with RDF plasmid (RD114 envelope), gag/pol plasmid and CAR plasmid. Retroviral viral supernatant was harvested at 48 and 72 hours. T cells were stimulated using 0.5 µg/mL of anti-CD3 and anti-CD28 antibodies in T175 TC-treated flasks and maintained in 100 U/mL IL-2. Non-TC treated six-well plates were coated with Retronectin and incubated at 4° C. for 24 hours prior to T cell transduction. A total of 3 ml of viral supernatant/supernatants was plated prior to the addition of 1 ml of activated T cells at a concentration of $1 \times 10^6$ cells/ml, 100 U/mL of IL-2 was then added and centrifuged at 1000×g for 40 minutes at room temperature and incubated at 37° C. and 5% CO2 for 2-3 days.

Human T-cells were:
triple transduced with vector A., B. and C. yielding a mix of product (AUTO7/ABC)
dual transduced with vector A. and B. yielding a mix of product (AUTO7/AB)
single transduced with vector A. yielding a single product (AUTO7/A)

Cytotoxicity Assay

CAR T-cells were co-cultured with SupT1-NT and SupT1-PSMA at an effector to target ratio (E:T ratio) of 1:2 or 1:8 a TC-treated 96-well plate. Readouts were taken 24 hours post co-culture by staining with anti-CD3-PeCy7 and Qben10-APC to differentiate effector T-cells and target cells, SYTOX Blue7-AAD dead cell stain was used to exclude dead cells. Cytotoxicity readouts were accessed by flow cytometry.

Cytotoxicity Assay in Presence of TGF

CAR T-cells were co-cultured with SupT1-NT and SupT1-PSMAhigh and SupT1-PSMAlow at an effector to target ratio (E:T ratio) of 1:2 or 1:8 a TC-treated 96-well plate. TGFβ1 was added at a concentration of 10 ng/ml on day 0, and cytotoxicity readouts were accessed by flow cytometry on day 7.

In Vitro Re-Stimulation Assay

CAR T-cells were co-cultured with SupT1-PSMAhigh or SupT1-PSMAlow target cells at 1:1 ratio (E:T). Every 7 days CAR T-cells were re-stimulated with $5 \times 10^4$ SupT1 cells. Cytotoxicity was assessed by FBK assay as describe above, and target:effectors ratio after re-stimulation was ascended by cytofluorimetric analysis. Supernatants were collected to assess cytokine release.

Cytokine ELISA

Human IL-2 ELISA MAX™ Deluxe and Human IFN-γ ELISA MAX™ Deluxe kits were used to access the levels of cytokine secreted into co-culture supernatants taken from Cytotoxicity Assay.

In Vivo Experiment

5×10⁶ PSMA positive PC3 human cell lines were injected in the flank of female NSG mice. Xenografts were left to establish for 3 weeks until stable engraftment was detectable by palpation and caliper measurement. Human PBMC were created by single, double or triple transduction. CAR T-cells were administered i.v. at a dose of 1×10⁶ CAR T-cells/mouse. Caliper measurement was taken 2/3 times a week and followed up for until the end of the animal protocol.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A cytolytic immune cell expressing:
   a) a chimeric antigen receptor (CAR) comprising an antigen-binding domain which binds disialoganglioside (GD2), wherein the CAR comprises a heavy chain variable region according to SEQ ID NO: 77 and a light chain variable region according to SEQ ID NO: 78;
   b) a chimeric cytokine receptor (CCR) which binds IL-7, wherein the CCR comprises a first polypeptide comprising a heavy chain constant region according to SEQ ID NO: 32 and an IL-7 receptor α-chain endodomain according to SEQ ID NO: 41, and a second polypeptide comprising a human light kappa chain according to SEQ ID NO: 30 and a γ-chain receptor endodomain according to SEQ ID NO: 39;
   c) a dominant negative SHP-2 (dnSH2) according to SEQ ID NO: 29; and
   d) a monomeric dominant negative transforming growth factor β receptor II (dnTGFBRII) according to SEQ ID NO: 46.

2. A method for making the cell according to claim 1, which comprises the step of introducing a nucleic acid or nucleic acids which encode a)-d) of claim 1 into a cytolytic immune cell ex vivo.

3. A pharmaceutical composition which comprises a plurality of cells according to claim 1, together with a pharmaceutically acceptable carrier, diluent or excipient.

4. A method for treating cancer which comprises the step of administering the pharmaceutical composition according to claim 3 to a subject.

5. The method of claim 4 wherein the cancer is neuroblastoma.

* * * * *

UNITED STATES PATENT AND TRADEMARK OFFICE
CERTIFICATE OF CORRECTION

PATENT NO. : 12,269,860 B2
APPLICATION NO. : 17/746664
DATED : April 8, 2025
INVENTOR(S) : Martin Pulé et al.

Page 1 of 1

It is certified that error appears in the above-identified patent and that said Letters Patent is hereby corrected as shown below:

In the Claims

At Column 133, Line 16, "(dnSH2)" should be -- (dnSHP2) --.

At Column 133, Line 19, "(dnTGFBRII)" should be -- (dnTGFβRII) --.

At Column 133, Line 31, "cancer is" should be -- cancer is a --.

Signed and Sealed this
Twelfth Day of August, 2025

Coke Morgan Stewart
*Acting Director of the United States Patent and Trademark Office*